United States Patent
Joo et al.

(10) Patent No.: US 11,155,543 B2
(45) Date of Patent: Oct. 26, 2021

(54) ORGANIC COMPOUND, AND ORGANIC LIGHT EMITTING DIODE AND ORGANIC LIGHT EMITTING DISPLAY DEVICE INCLUDING THE SAME

(71) Applicant: LG Display Co., Ltd., Seoul (KR)

(72) Inventors: Sung-Hoon Joo, Paju-si (KR); Seon-Keun Yoo, Gunpo-si (KR); Seung-Hee Yoon, Seoul (KR); Ji-Cheol Shin, Seoul (KR)

(73) Assignee: LG DISPLAY CO., LTD., Seoul (KR)

(*) Notice: Subject to any disclaimer, the term of this patent is extended or adjusted under 35 U.S.C. 154(b) by 224 days.

(21) Appl. No.: 15/799,421

(22) Filed: Oct. 31, 2017

(65) Prior Publication Data
US 2018/0118742 A1    May 3, 2018

(30) Foreign Application Priority Data

Oct. 31, 2016    (KR) .................. 10-2016-0143283

(51) Int. Cl.
*H01L 51/50*    (2006.01)
*C07D 471/04*    (2006.01)
(Continued)

(52) U.S. Cl.
CPC ........ *C07D 471/04* (2013.01); *H01L 51/0052* (2013.01); *H01L 51/0072* (2013.01);
(Continued)

(58) Field of Classification Search
None
See application file for complete search history.

(56) References Cited

U.S. PATENT DOCUMENTS

2006/0124924 A1* 6/2006 Suh .................. H01L 51/002
257/40
2009/0096357 A1* 4/2009 Lee .................. H01L 51/5092
313/504
(Continued)

FOREIGN PATENT DOCUMENTS

CN    103187531 A        7/2013
CN    103374040     *  1/2016  ........... H01L 51/005
(Continued)

OTHER PUBLICATIONS

Tan et al., "Promising Operational Stability of Potentially High Power Efficiency Organic Light-Emitting Diodes Utilizing a Simple and Versatile Electron-Transport/Hole-Blocking Layer," Adv. Electron. Mater. 2016, 2, 1600101, pp. 1-8.
(Continued)

*Primary Examiner* — Gregory D Clark
(74) *Attorney, Agent, or Firm* — Birch, Stewart, Kolasch & Birch, LLP

(57) ABSTRACT

An embodiment of the present invention provides an organic compound represented by:

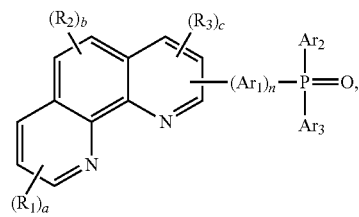

and an organic light emitting diode and an organic light emitting display device using the organic compound. The organic compound of the present invention includes a (Continued)

phenanthroline core, which has a nitrogen atom of a relatively electron rich $sp^2$ hybrid orbital, and a phosphine oxide moiety, which has an excellent electron transporting property and an excellent thermal stability. The electron transporting property of the organic compound of the present invention is improved based on the chemical structure of the organic compound. Accordingly, when the organic compound is used for the organic light emitting diode and the organic light emitting display device, the driving voltage is reduced, and the lifetime and the emitting efficiency are improved.

13 Claims, 5 Drawing Sheets

(51) Int. Cl.
*H01L 51/00* (2006.01)
*H01L 51/52* (2006.01)

(52) U.S. Cl.
CPC ........ *H01L 51/508* (2013.01); *H01L 51/5084* (2013.01); *H01L 51/5278* (2013.01)

(56) References Cited

U.S. PATENT DOCUMENTS

| | | | | |
|---|---|---|---|---|
| 2016/0005979 A1* | 1/2016 | Kim | ................... | H01L 51/0061 257/40 |
| 2016/0005980 A1* | 1/2016 | Ito | ....................... | H01L 51/0072 257/40 |
| 2016/0013427 A1 | 1/2016 | Kim et al. | | |
| 2016/0020405 A1* | 1/2016 | Ito | ....................... | H01L 51/0067 257/40 |

FOREIGN PATENT DOCUMENTS

| | | | | |
|---|---|---|---|---|
| CN | 105321984 A | 2/2016 | | |
| CN | 105609648 A | 5/2016 | | |
| CN | 105693773 A | 6/2016 | | |
| ER | 2983227 A1 | 2/2016 | | |
| JP | 2004-204140 A | 7/2004 | | |
| JP | 2006-73581 A | 3/2006 | | |
| JP | 2008-71993 A | 3/2008 | | |
| KR | 10-2016-0005196 A | 1/2016 | | |
| KR | 10-2016-0007984 A | 1/2016 | | |
| KR | 10-2016-0053048 A | 5/2016 | | |
| KR | 2016053048 | * | 5/2016 | ............. C09K 11/06 |
| WO | WO 2016/140549 A2 | 9/2016 | | |

OTHER PUBLICATIONS

RN: 122768-52-9, Registry Database, Sep. 22, 1989, http://www.cas.org, 1 page total.

* cited by examiner

ORGANIC COMPOUND, AND ORGANIC LIGHT EMITTING DIODE AND ORGANIC LIGHT EMITTING DISPLAY DEVICE INCLUDING THE SAME

The present application claims the priority benefit of Korean Patent Application No. 10-2016-0143283 filed in Republic of Korea on Oct. 31, 2016, which is hereby incorporated by reference into the present application.

BACKGROUND OF THE INVENTION

Field of the Invention

The present invention relates to an organic compound and more particularly to an organic compound being capable of reducing a driving voltage of an organic light emitting diode and improving an emitting efficiency and a lifetime of the organic light emitting diode and the organic light emitting display device including the organic compound.

Discussion of the Related Art

As requests for a flat panel display device having a small occupied area have been increased, an organic light emitting display (OLED) device including an organic light emitting diode has been the subject of recent research and development.

The organic light emitting diode emits light by injecting electrons from a cathode as an electron injection electrode and holes from an anode as a hole injection electrode into an emitting material layer (EML), combining the electrons with the holes, generating an exciton, and transforming the exciton from an excited state to a ground state. A flexible substrate, for example, a plastic substrate, can be used as a base substrate where elements are formed. Since the OLED device does not require a backlight assembly, the OLED device has low weight and low power consumption. Moreover, the OLED device can be operated at a voltage (e.g., 10V or below) lower than a voltage required to operate other display devices.

To efficiently inject the electron from the cathode into the EML, an organic light emitting diode for the OLED device may further include an electron injection layer (EIL) and an electron transporting layer (ETL) between the cathode and the EML. For example, the ETL may include tris-8-hydroxy-quinoline aluminum (Alq3), 2-biphenyl-4-yl-5-(4-t-butylphenyl)-1,3,4-oxadiazole (PBD) or lithium quinolate (Liq). In addition, to increase the electron transfer from the EIL into the ETL, the ETL may further include an alkali metal or an alkali earth metal as a dopant.

When the organic light emitting diode is driven, the alkali metal or the alkali earth metal may be transferred into an interface of the EML with the electron. Accordingly, an amount of the alkali metal or the alkali earth metal in the interface of the EML is increased, and an amount of the alkali metal or the alkali earth metal in the interface of the ETL is decreased. As a result, the electron injected to the EML is decreased such that the driving voltage of the organic light emitting diode is increased and the emitting efficiency of the organic light emitting diode is decreased. In addition, the lifetime of the organic light emitting diode is decreased.

SUMMARY OF THE INVENTION

Accordingly, the present invention is directed to an organic compound and an organic light emitting diode and an organic light emitting display (OLED) device including the same that substantially obviate one or more of the problems due to limitations and disadvantages of the related art.

An object of the present invention is to provide an organic compound being capable of preventing the decrease of an electron transporting/injection property and the lifetime.

An object of the present invention is to provide an organic light emitting diode and an OLED device having improved electron transporting/injection property and lifetime.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described herein, an organic compound is represented by following Formula:

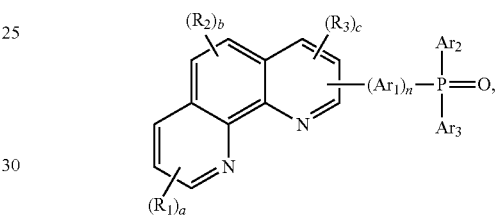

wherein each of $R_1$ to $R_3$ is independently selected from the group consisting of hydrogen, deuterium, tritium, substituted or non-substituted $C_1$-$C_{20}$ alkyl, substituted or non-substituted $C_1$-$C_{20}$ alkoxy, substituted or non-substituted $C_5$-$C_{30}$ cycloalkyl, substituted or non-substituted $C_4$-$C_{30}$ heterocycloalkyl, substituted or non-substituted $C_5$-$C_{30}$ aryl, substituted or non-substituted $C_4$-$C_{30}$ heteroaryl, substituted or non-substituted $C_5$-$C_{30}$ oxyaryl and substituted or non-substituted $C_4$-$C_{30}$ hetero-oxyaryl, wherein "a" is 2 or 3, "b" is 1 or 2, "c" is 2 or 3, and the summation of "a", "b" and "c" is 7, wherein $Ar_1$ is selected from the group consisting of substituted or non-substituted $C_1$-$C_{20}$ alkylene, substituted or non-substituted $C_5$-$C_{30}$ cycloalkylene, substituted or non-substituted $C_4$-$C_{30}$ heterocycloakylene, substituted or non-substituted $C_5$-$C_{30}$ arylene and substituted or non-substituted $C_4$-$C_{30}$ heteroarylene, and each of $Ar_2$ and $Ar_3$ is independently selected from the group consisting of hydrogen, deuterium, tritium, halogen, nitrile, substituted or non-substituted $C_5$-$C_{30}$ aryl, substituted or non-substituted $C_4$-$C_{30}$ heteroaryl, substituted or non-substituted $C_5$-$C_{30}$ oxyaryl and substituted or non-substituted $C_4$-$C_{30}$ hetero-oxyaryl, and wherein "n" is 0, 1 or 2.

In another aspect, an organic light emitting diode comprises first and second electrodes facing each other; an emitting material layer between the first and second electrodes; and an electron transporting layer between the emitting material layer and the second electrode and including the organic compound.

In another aspect, an organic light emitting diode comprises first and second electrodes facing each other; a first emitting part between the first and second electrodes and including a first emitting material layer and a first electron transporting layer; a second emitting part between the first emitting part and the second electrode and including a second emitting material layer and a second electron transporting layer; and a first charge generation layer between the first and second emitting parts, wherein at least one of the first electron transporting layer, the second electron transporting layer and the first charge generation layer includes the above-mentioned organic compound represented by Formula:

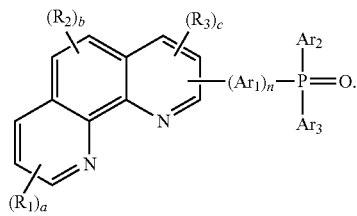

In another aspect, an organic light emitting display device comprises a substrate; the organic light emitting diode: and a thin film transistor between the substrate and the organic light emitting diode and connected to the organic light emitting diode.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

DETAILED DESCRIPTION OF THE PREFERRED EMBODIMENTS

Figure 1:
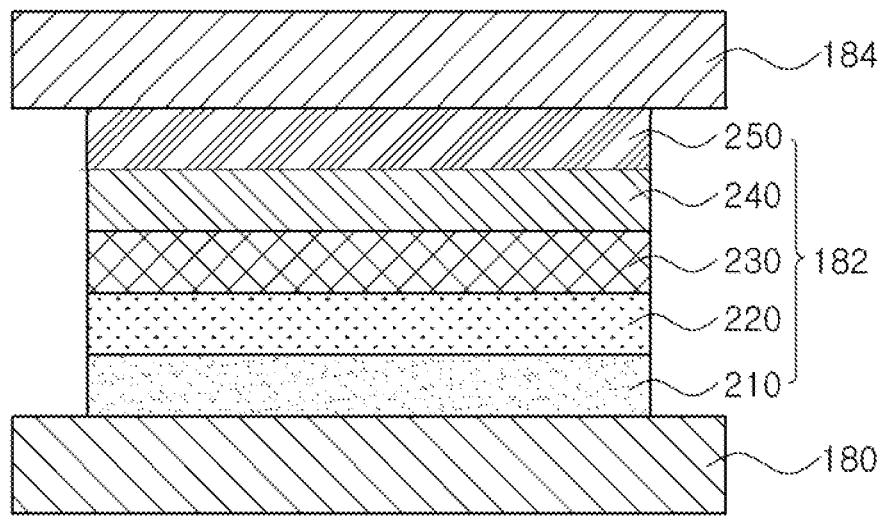
FIG. 1 is a schematic cross-sectional view of an organic light emitting diode according to a first embodiment of the present invention.

Reference will now be made in detail to the preferred embodiments, examples of which are illustrated in the accompanying drawings.

An organic compound of the present invention includes a phenanthroline core and a phosphine oxide moiety directly or indirectly connected (or linked) to the phenanthroline core. The organic compound is represented in Formula 1.

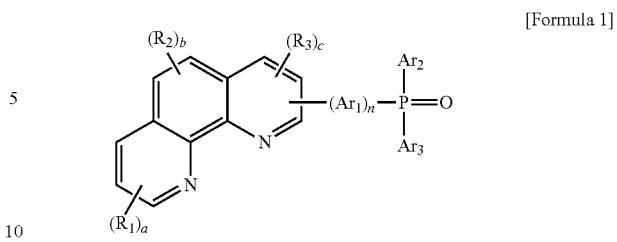

[Formula 1]

In Formula 1, each of $R_1$ to $R_3$ is independently selected from the group consisting of hydrogen, deuterium, tritium, substituted or non-substituted $C_1$-$C_{20}$ alkyl, substituted or non-substituted $C_1$-$C_{20}$ alkoxy, substituted or non-substituted $C_5$-$C_{30}$ cycloalkyl, substituted or non-substituted $C_4$-$C_{30}$ heterocycloalkyl, substituted or non-substituted $C_5$-$C_{30}$ aryl, substituted or non-substituted $C_4$-$C_{30}$ heteroaryl, substituted or non-substituted $C_5$-$C_{30}$ oxyaryl and substituted or non-substituted $C_4$-$C_{30}$ hetero-oxyaryl. In Formula 1, "a" is 2 or 3, "b" is 1 or 2, "c" is 2 or 3, and the summation of "a", "b" and "c" is 7. (a+b+c=7) $Ar_1$ is selected from the group consisting of substituted or non-substituted $C_1$-$C_{20}$ alkylene, substituted or non-substituted $C_5$-$C_{30}$ cycloalkylene, substituted or non-substituted $C_4$-$C_{30}$ heterocycloalkylene, substituted or non-substituted $C_5$-$C_{30}$ arylene and substituted or non-substituted $C_4$-$C_{30}$ heteroarylene. In Formula 1, "n" is 0, 1 or 2, and each of $Ar_2$ and $Ar_3$ is independently selected from the group consisting of hydrogen, deuterium, tritium, halogen, nitrile, substituted or non-substituted $C_5$-$C_{30}$ aryl, substituted or non-substituted $C_4$-$C_{30}$ heteroaryl, substituted or non-substituted $C_5$-$C_{30}$ oxyaryl and substituted or non-substituted $C_4$-$C_{30}$ hetero-oxyaryl.

When $R_1$ to $R_3$ and $Ar_1$ to $Ar_3$ are substituted, the substituent may be one of non-substituted or halogen-substituted $C_1$-$C_{20}$ alkyl, non-substituted or halogen-substituted $C_1$-$C_{20}$ alkoxy, halogen, cyano, carboxyl, carbonyl, amine, $C_1$-$C_{20}$ alkyl amine, nitro, hydrazyl, sulfone, $C_1$-$C_{20}$ alkyl silyl, $C_1$-$C_{20}$ alkoxy silyl, $C_3$-$C_{30}$ cycloalkyl silyl, $C_5$-$C_{30}$ aryl silyl, substituted or non-substituted $C_5$-$C_{30}$ aryl and $C_4$-$C_{30}$ heteroaryl, but it is not limited thereto.

The term of "hetero", which is used in heteroaryl, heteroarylene, and so on, means that at least one carbon atom in the aromatic ring or alicyclic ring is substituted by a heteroatom being selected from the group consisting of nitrogen atom (N), oxygen atom (O) and sulfur atom (S).

For example, each of $R_1$ to $R_3$ may be substituted or non-substituted $C_5$-$C_{30}$ aryl or substituted or non-substituted $C_4$-$C_{30}$ heteroaryl. Each of $R_1$ to $R_3$ may be fused or non-fused homo-aromatic ring, such as phenyl, biphenyl, terphenyl, tetraphenyl, naphtyl, anthracenyl, indenyl, phenanthrenyl, azulenyl, pyrenyl, fluorenyl, tetracenyl, indacenyl or spiro-fluorenyl, or fused or non-fused heteroaromatic ring, such as pyrrolyl, pyridyl (or pyridinyl), pyrimidyl (pyrimidinyl), pyrazinyl, pyridazinyl, triazinyl, tetrazinyl, imidazolyl, pyrazolyl, indolyl, carbazolyl, benzocarbazolyl, dibenzocarbazolyl, carbolinyl, indolocarbazolyl, indenocarbazolyl, quinolinyl, iso-quinolinyl, phthalazinyl, quinoxalinyl, cinnolinyl, quinazolinyl, benzoquinolinyl, benzo iso-quinolinyl, benzoqhinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thio-pyranyl, thiazinyl, thiophenyl or N-substituted spiro-fluorenyl.

For example, each of $R_1$ to $R_3$ may be independently selected from the group consisting of phenyl, alkylphenyl, biphenyl, alkylbiphenyl, halophenyl, alkoxyphenyl, haloalkoxyphenyl, cyanophenyl, silylphenyl, naphthyl, alkylnaphthyl, halonaphthyl, cyanonaphthyl, silylnaphthyl, phenylnaphthyl, pyridyl, alkylpyridyl, halopyridyl, cyano-pyridyl, alkoxypyridyl, silylpyridyl, phenylpyridyl, pyrimidyl, halopyrimidyl, cyanopyrimidyl, alkoxypyrimidyl, phenylpyrimidyl, quinolinyl, isoquinolinyl, phenylquinolinyl, quinoxalinyl, pyrazinyl, quinazolinyl, naphthyridinyl, benzothiophenyl, benzofuranyl, dibenzothiophenyl, arylthiazolyl, dibenzofuranyl, fluorenyl, carbazoyl, imidazolyl, carbolinyl, phenanthrenyl, terphenyl, terpyridyl, phenylterpyridyl, triphenylenyl, fluoranthenyl and diazafluorenyl. In the organic compound of the exemplary embodiment of the present invention, each of $R_1$ to $R_3$ may be independently selected from substituted or non-substituted phenyl or substituted or non-substituted naphthyl, but it is not limited thereto.

The carrier mobility of the organic compound may be controlled by $Ar_1$ as a linker (or connection moiety). $Ar_1$ may be selected from $C_1$-$C_{20}$ alkylene, such as methylene, ethylene or butylene, substituted or non-substituted $C_5$-$C_{30}$ arylene and substituted or non-substituted $C_4$-$C_{30}$ heteroarylene.

When $Ar_1$ is substituted or non-substituted $C_5$-$C_{30}$ arylene or substituted or non-substituted $C_4$-$C_{30}$ heteroarylene, $Ar_1$ may be selected from the group consisting of phenylene, biphenylene, terphenylene, triphenylene, tetraphenylene, indenylene, naphthylene, azulenylene, indacenylene, acenaphthylene, fluorenylene, dibenzofluorenylene, spiro-fluorenylene, phenalenylene, phenanthrenylene, anthracenylene, fluoranthrenylene, triphenylenylene, pyrenylene, chrysenylene, naphthacenylene, picenylene, perylenylene, pentaphenylene, hexacenylene, pyrrolylene, imidazolylene, benzimidazolylene, pyrazolylene, pyridinylene, terpyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzoquinolinylene, benzo iso-quinolinylene, benzoquinazolinylene, benzoquinoxalinylene, cinnolinylene, phenanthridinylene, carbolinylene, acridinylene, phenanthrolinylene, phenazinylene, benzoxazolylene, benzimidazolylene, furanylene, benzofuranylene, thiophenylene, benzothiophenylene, dibenzothiophenylene, thiazolylene, isothiazolylene, benzothiazolylene, isoxazolylene, oxazolylene, triazolylene, tetrazolylene, oxadiazolylene, triazinylene, dibenzofuranylene, dibenzothiophenylene, carbazolylene, benzocarbazolylene, dibenzocarbazolylene, indolocarbazolylene, indenocarbazolylene, imidazopyrimidinylene and imidazopyridinylene.

For example, $Ar_1$ may be selected from the group consisting of phenylene, biphenylene, terphenylene, naphthylene, anthracenylene, phenanthrenylene, triphenylene, pyrenylene, fluorenylene, pyridinylene, pyrimidinylene, pyridazinylene, pyrazinylene, benzothiophenylene, dibenzothiophenylene, benzofuranylene and dibenzofuranylene, which may be substituted by $C_1$-$C_{20}$ alkyl, cyano, $C_5$-$C_{30}$ aryl or $C_4$-$C_{30}$ heteroaryl.

When the number of rings of $Ar_1$ is increased, the conjugation length of the organic compound is increased such that the energy band gap of the organic compound is decreased. Accordingly, the number of rings of $Ar_1$ may be 1 to 4. To improve the electron transporting property of the organic compound, $Ar_1$ may be a 5-numbered atom ring to a 7-numbered atom ring, and beneficially a 6-numbered atom ring.

In the organic compound of the exemplary embodiment of the present invention, each of $Ar_2$ and $Ar_3$ may be independently selected from substituted or non-substituted $C_5$-$C_{30}$ aryl and substituted or non-substituted $C_4$-$C_{30}$ heteroaryl. For example, each of $Ar_2$ and $Ar_3$ may be fused or non-fused homo-aromatic ring, such as phenyl, biphenyl, terphenyl, tetraphenyl, naphtyl, anthracenyl, indenyl, phenanthrenyl, azulenyl, pyrenyl, fluorenyl, tetracenyl, indacenyl or spirofluorenyl, or fused or non-fused hetero-aromatic ring, such as pyrrolyl, pyridyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, carbolinyl, indolocarbazolyl, indenocarbazolyl, quinolinyl, iso-quinolinyl, phthalazinyl, quinoxalinyl, cinnolinyl, quinazolinyl, benzoquinolinyl, benzo iso-quinolinyl, benzoqhinazolinyl, benzoquinoxalinyl, acrydinyl, phenanthrolinyl, furanyl, pyranyl, oxazinyl, oxazolyl, oxadiazolyl, triazolyl, dioxynyl, benzofuranyl, dibenzofuranyl, thio-pyranyl, thiazinyl, thiophenyl or N-substituted spiro-fluorenyl, and beneficially phenyl, biphenyl, anthracenyl, pyridyl, pyrimidyl, pyrazinyl, pyridazinyl or carbazolyl.

Since the organic compound of the present invention includes the phenanthroline core, which has the nitrogen atom of a relatively electron rich $sp^2$ hybrid orbital, and the phosphine oxide moiety, which has an excellent electron transporting property and an excellent thermal stability, the electron transporting property of the organic compound of the present invention is improved. Accordingly, when the organic compound is used for the ETL of the organic light emitting diode and the OLED device, the driving voltage is reduced, and the lifetime and the emitting efficiency are improved.

In addition, since the nitrogen atom of the phenanthroline core in the organic compound is combined or bonded with the alkali metal or the alkali earth metal as a dopant in the ETL or an N-type charge generation layer (CGL) to form a gap state, the electron transporting property of the ETL or the N-type CGL is further improved. Moreover, since the organic compound is combined with the alkali metal or the alkali earth metal in the ETL or the N-type CGL, the diffusion of the alkali metal or the alkali earth metal into the EML or the P-type CGL is prevented. Accordingly, when the organic compound is used for the N-type CGL in a tandem structure light emitting diode or OLED device, the electron is efficiently transferred from the N-type CGL into the ETL, the driving voltage is reduced, and the lifetime and the emitting efficiency are improved.

The organic compound in the Formula 1 may be one of materials in Formula 2.

[Formula 2]

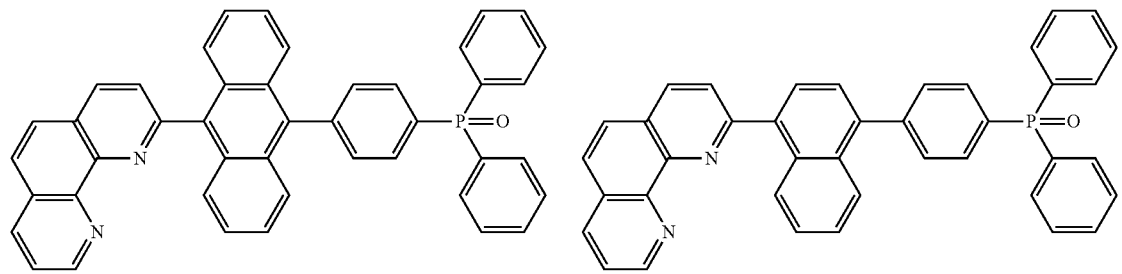

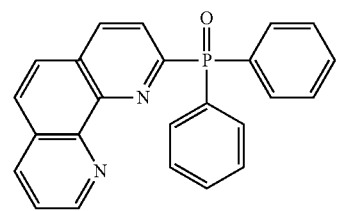
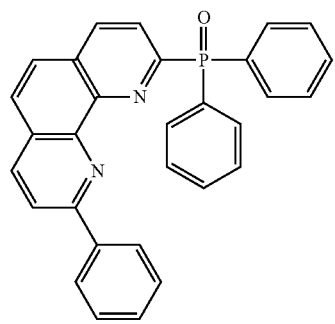
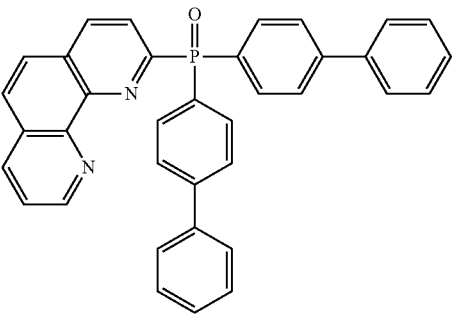
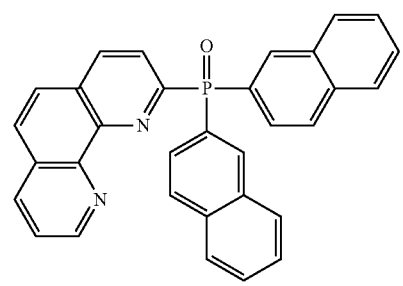
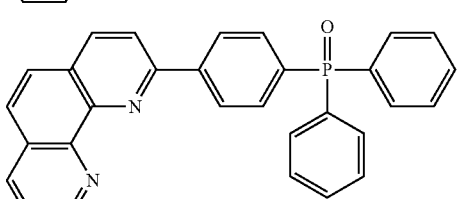
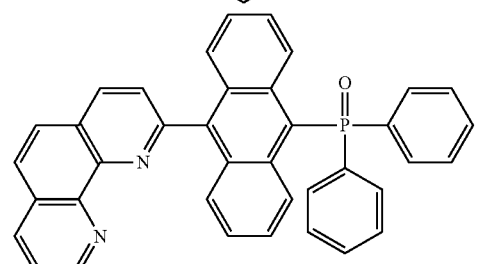
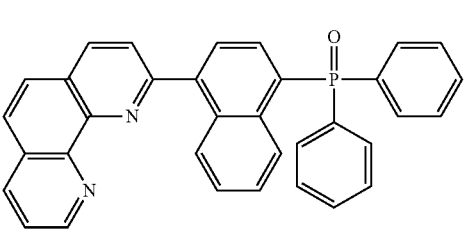
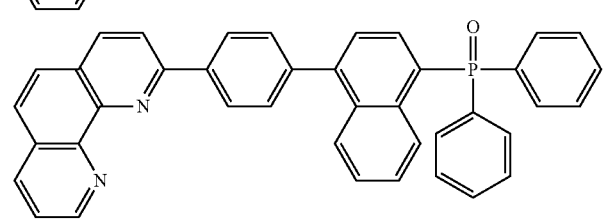
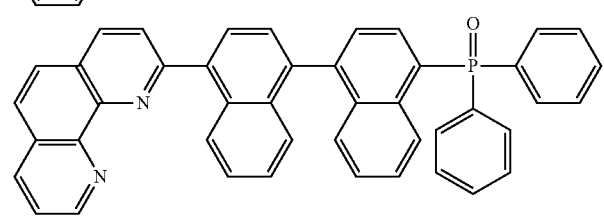
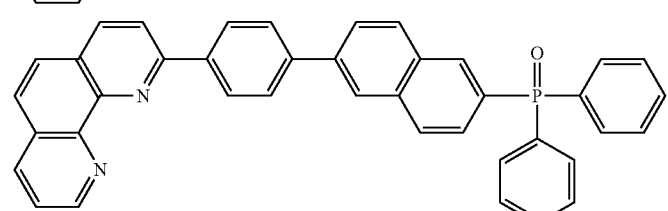
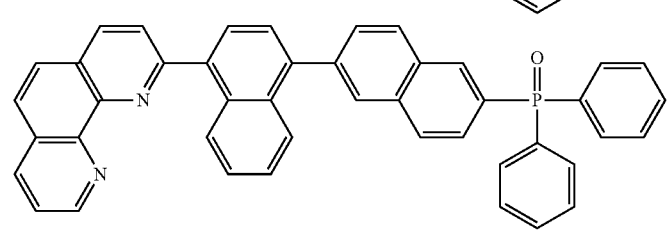

-continued
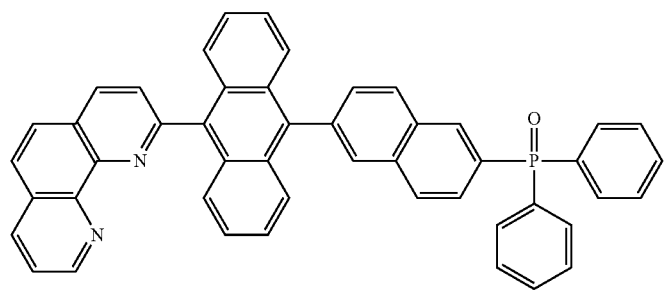
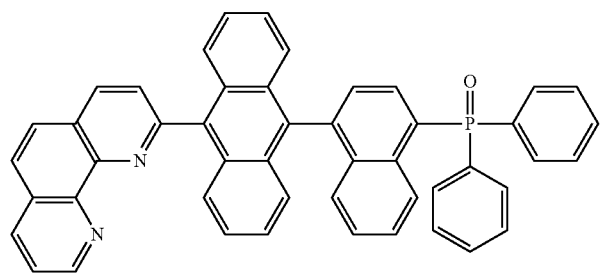
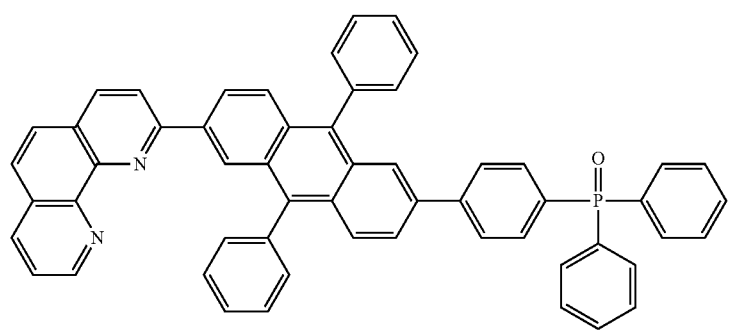
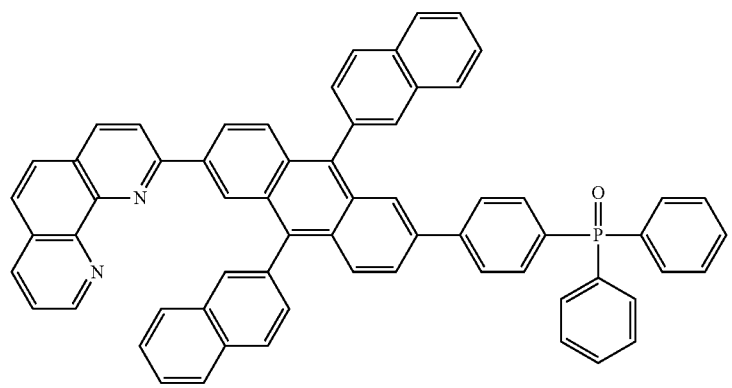
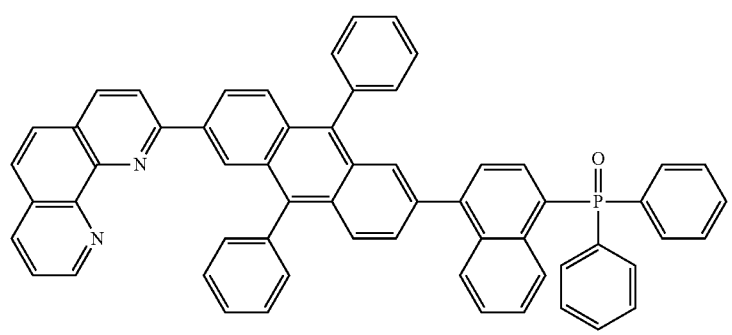

-continued
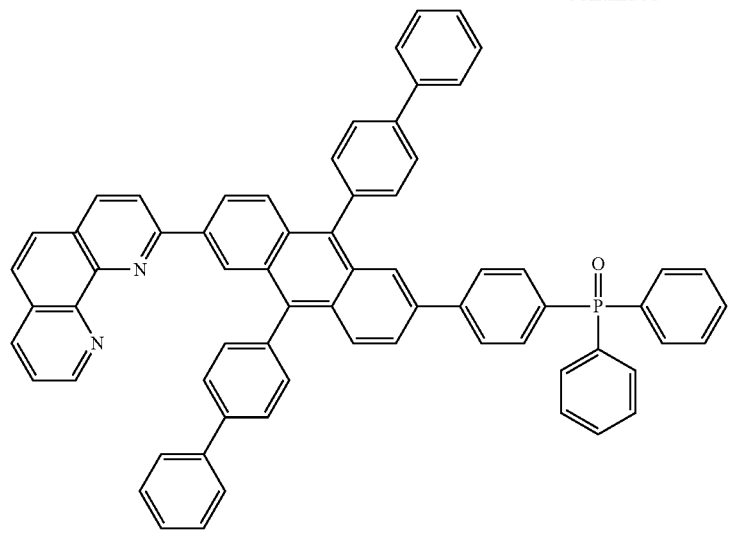
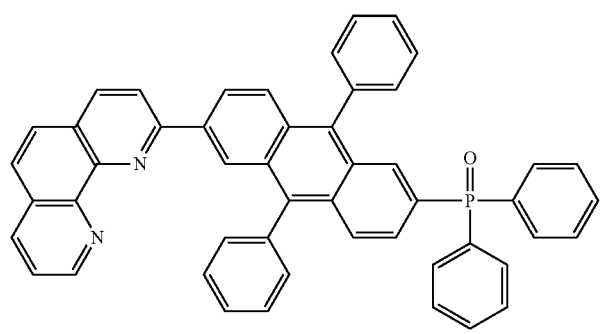
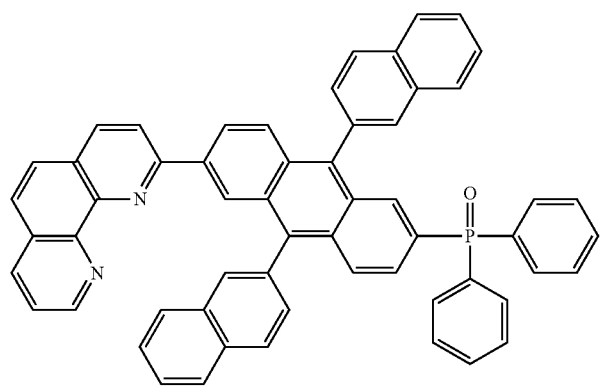
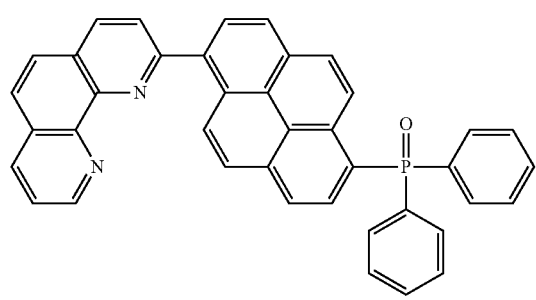

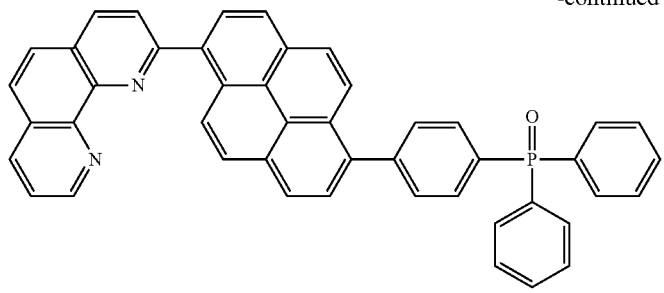
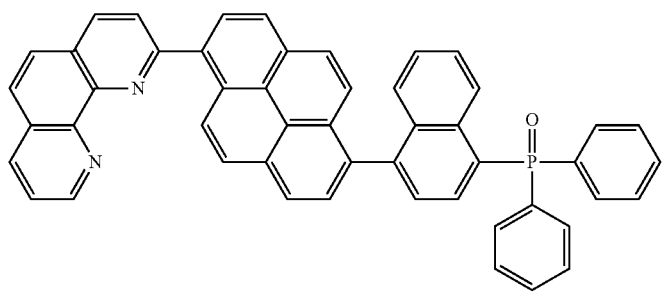
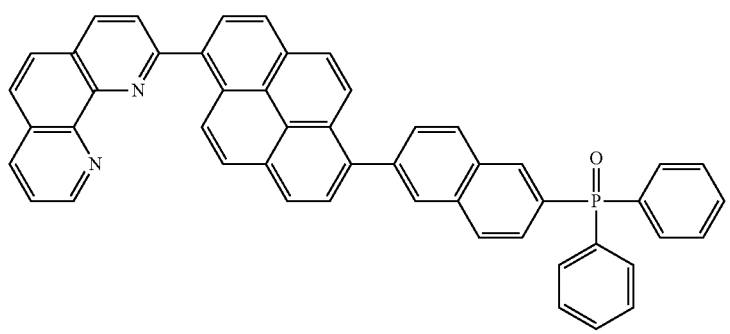
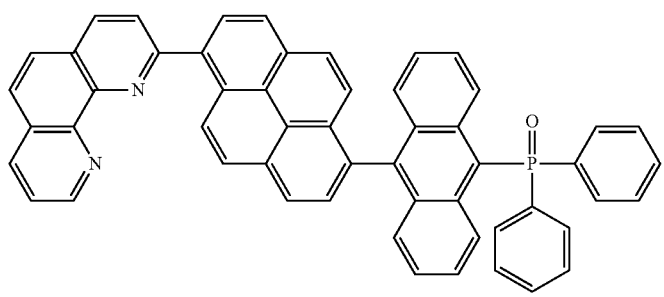
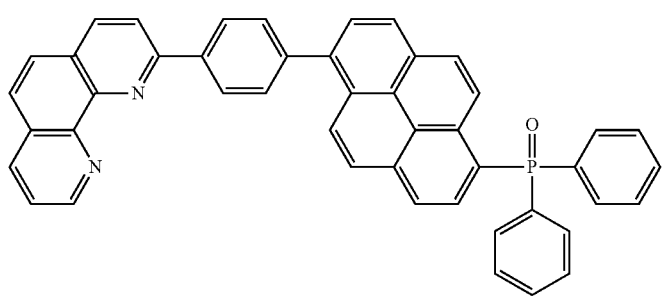

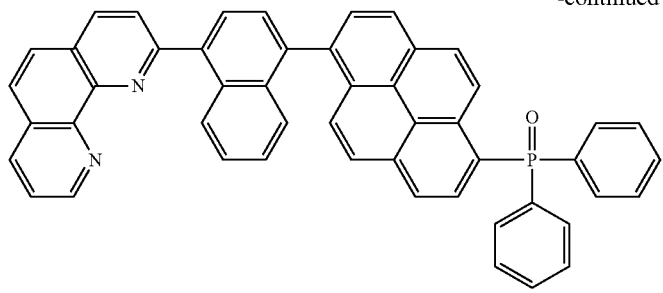
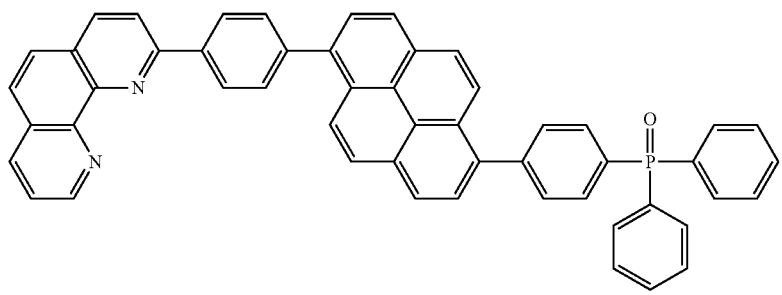
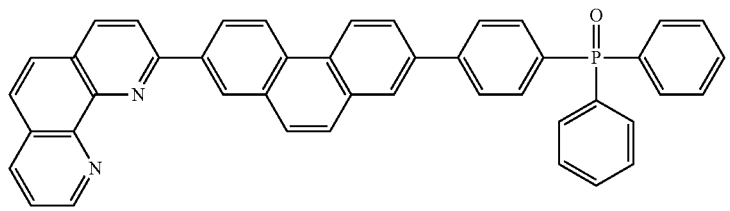
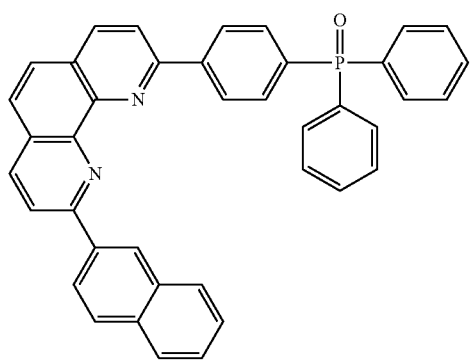
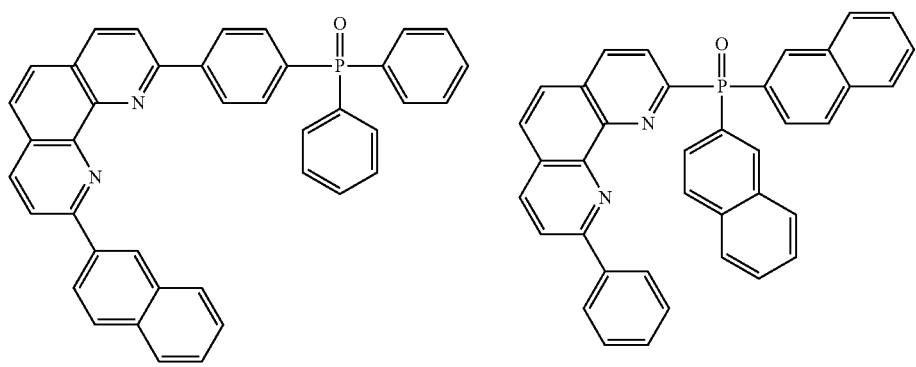

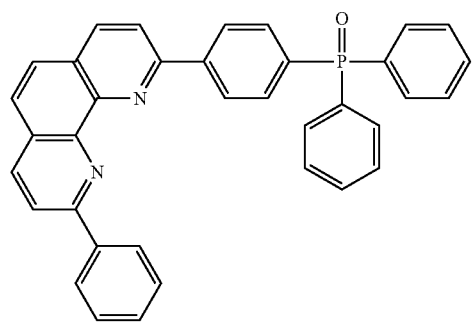
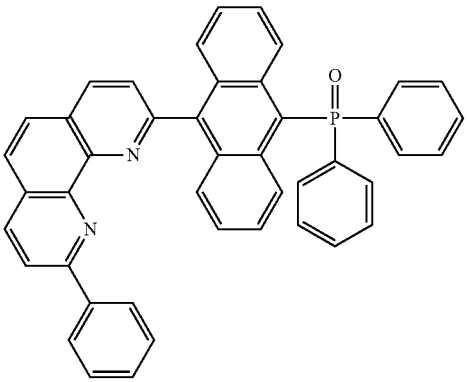
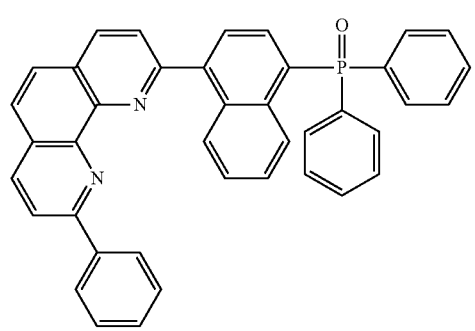
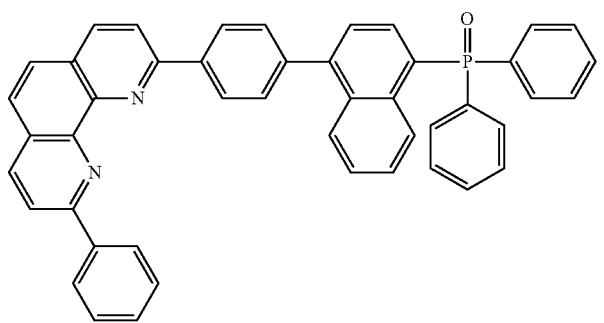
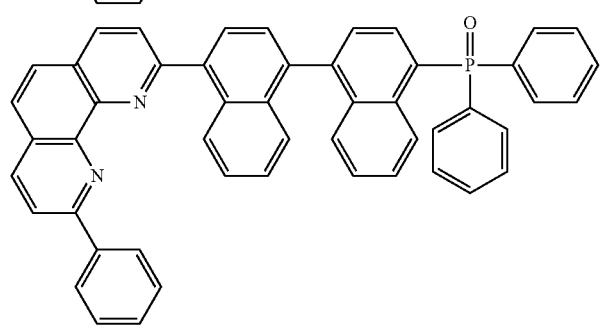
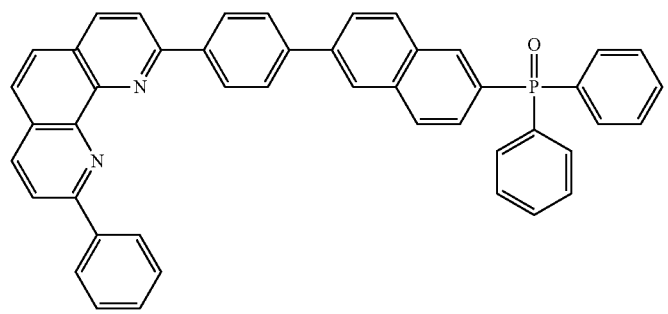
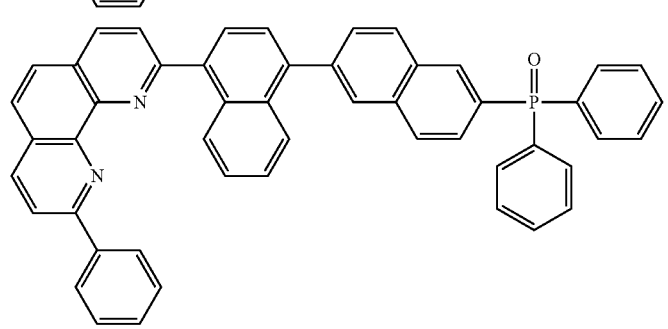

-continued
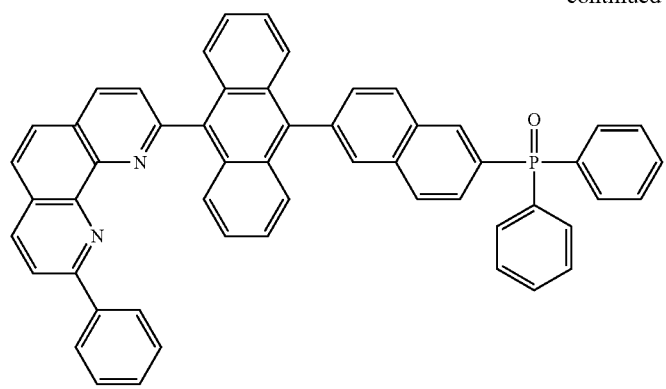
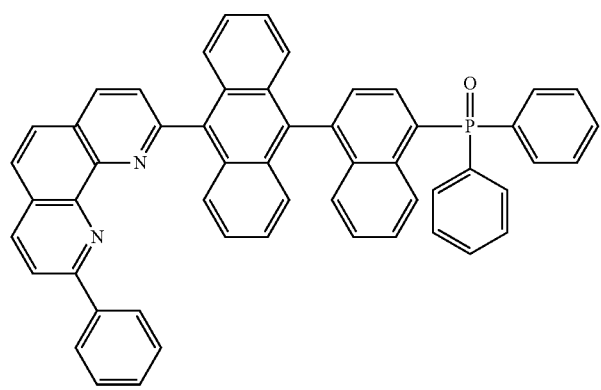
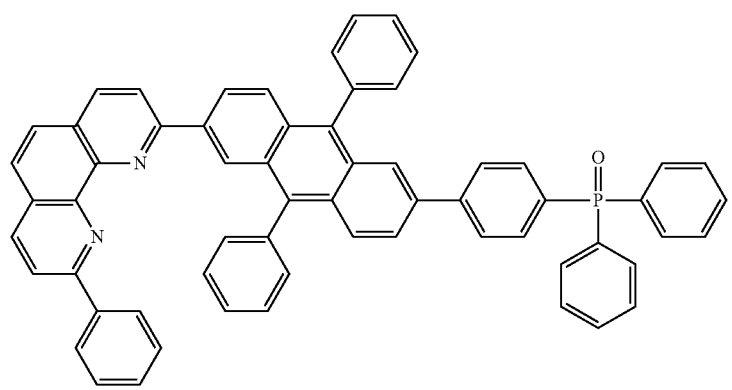
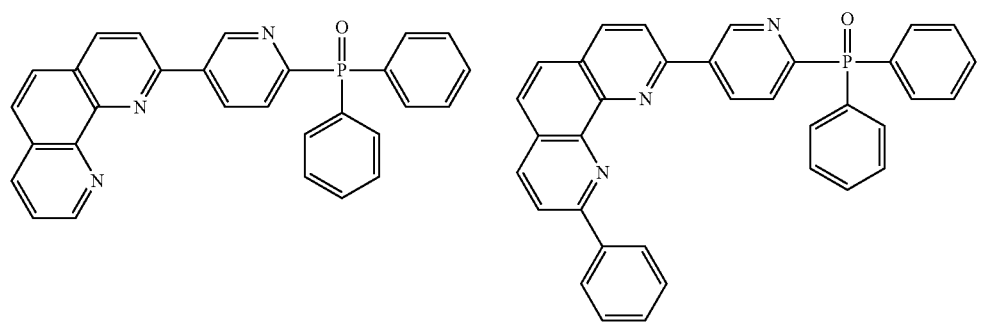

-continued
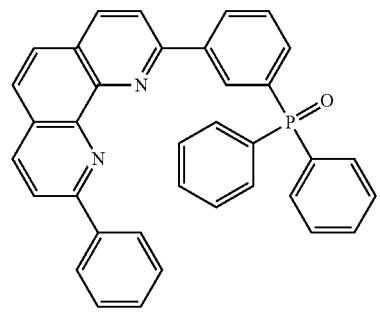
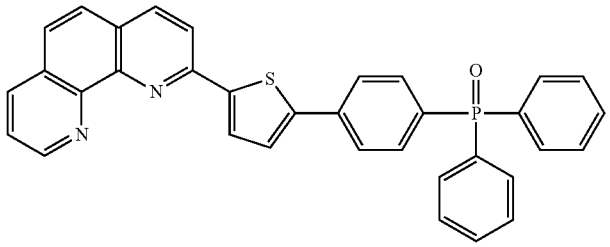
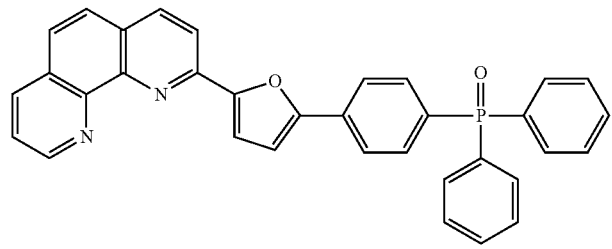
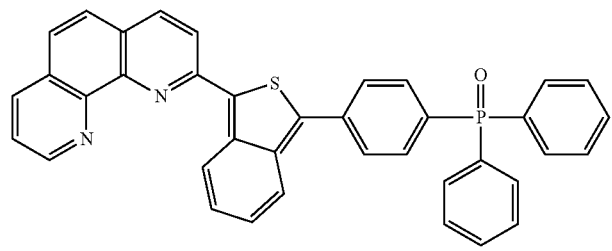
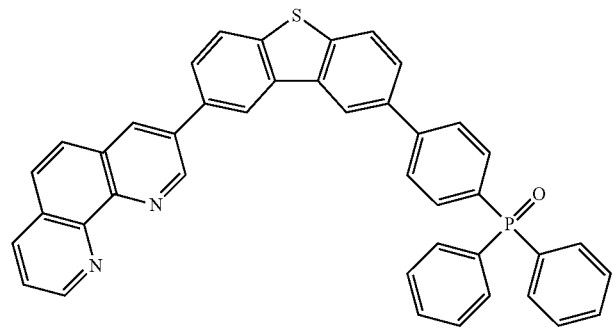
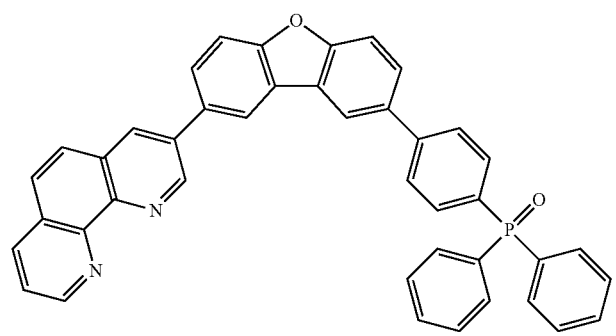
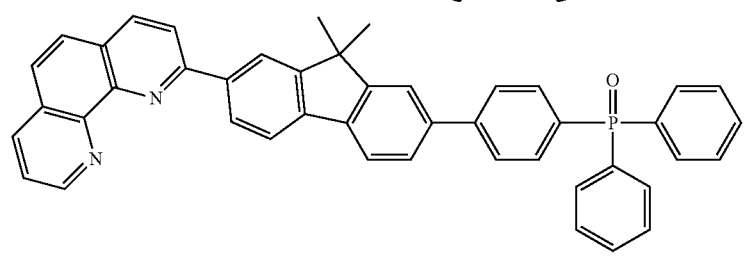

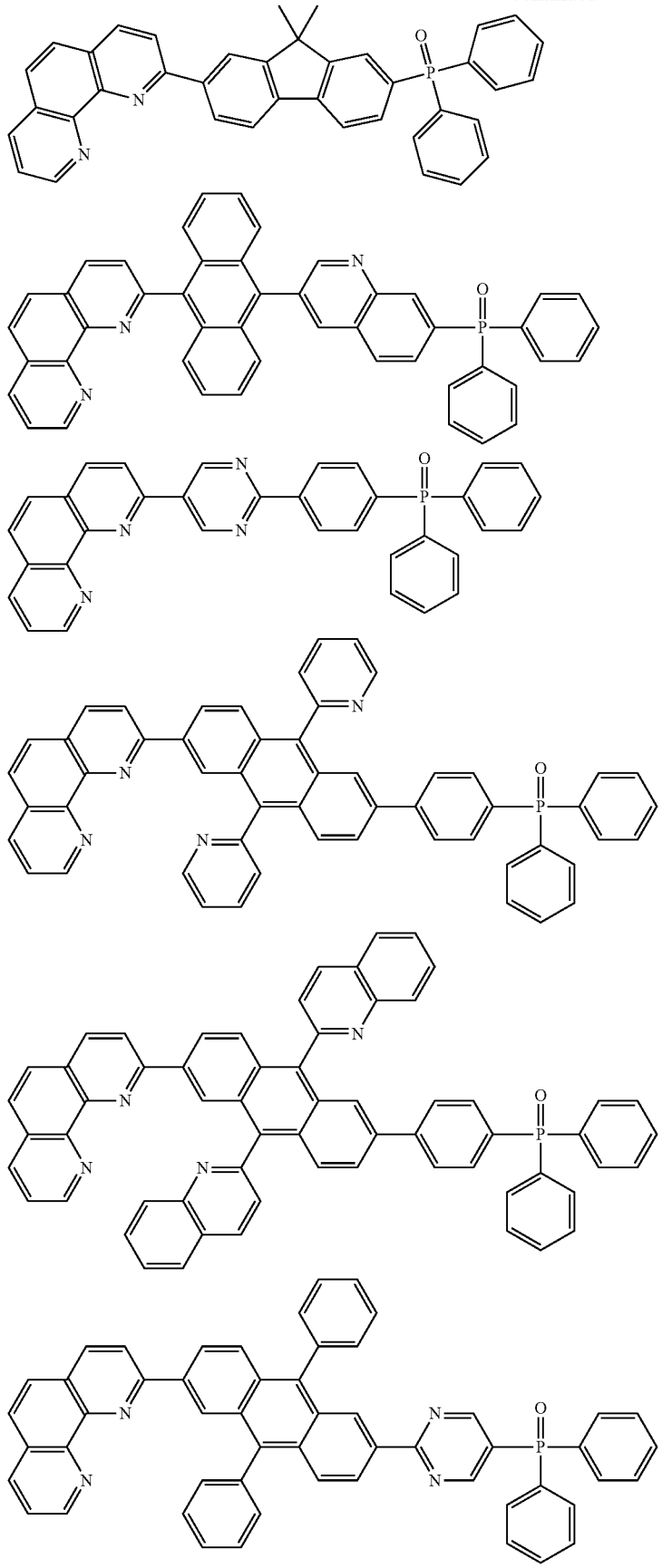

-continued
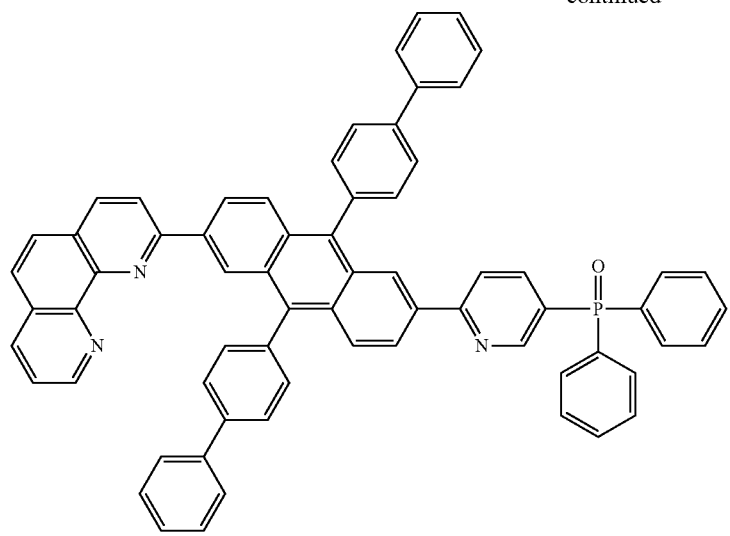
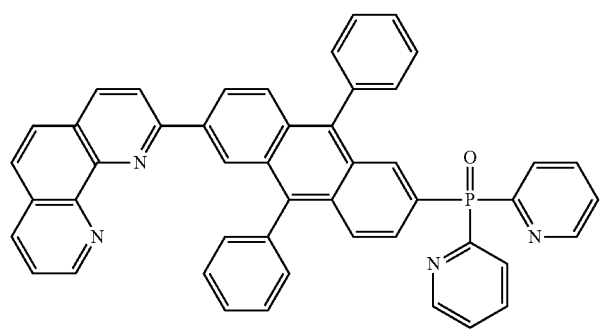
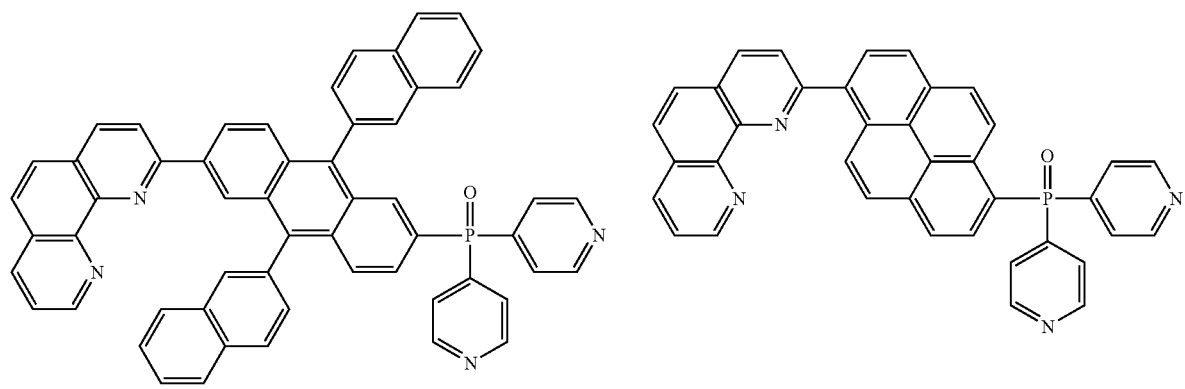
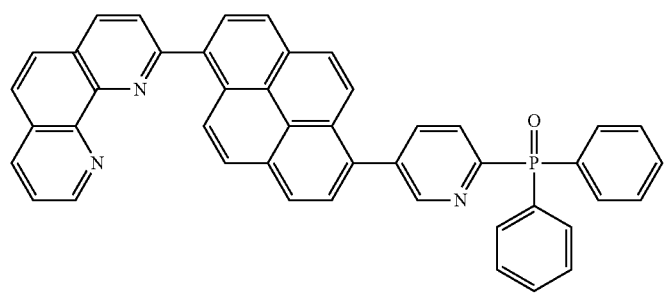

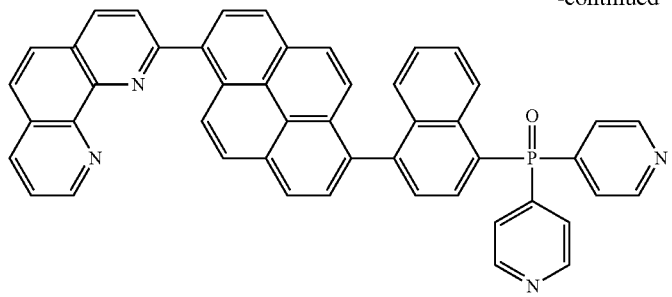
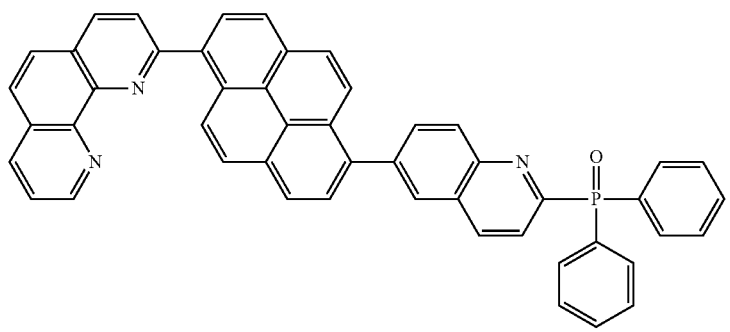
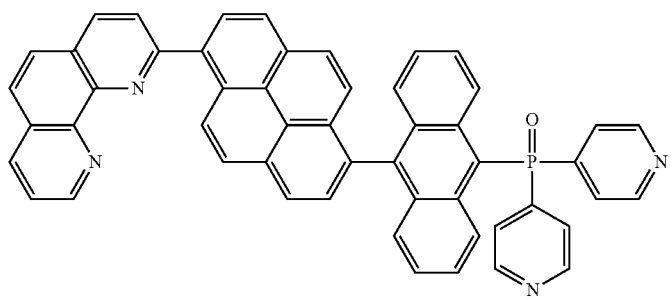
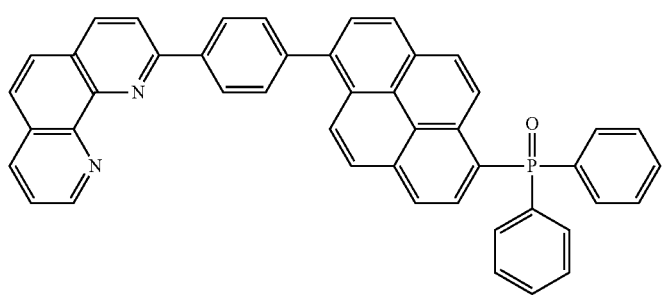
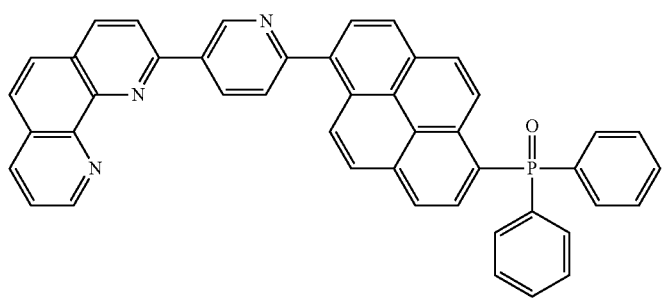

-continued
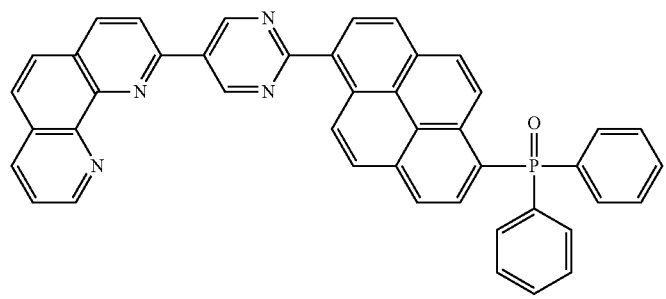
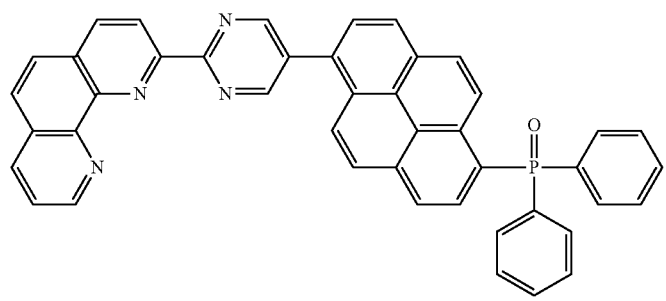
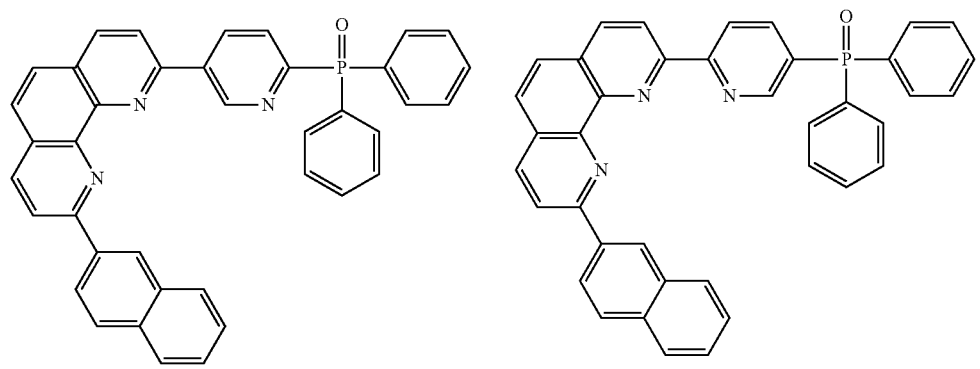
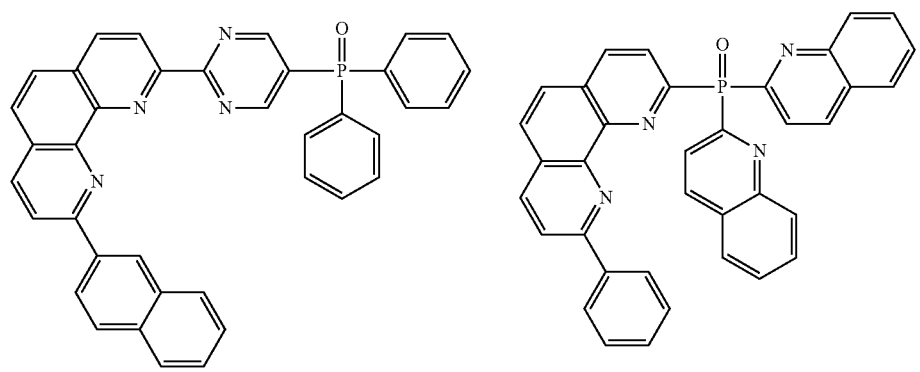
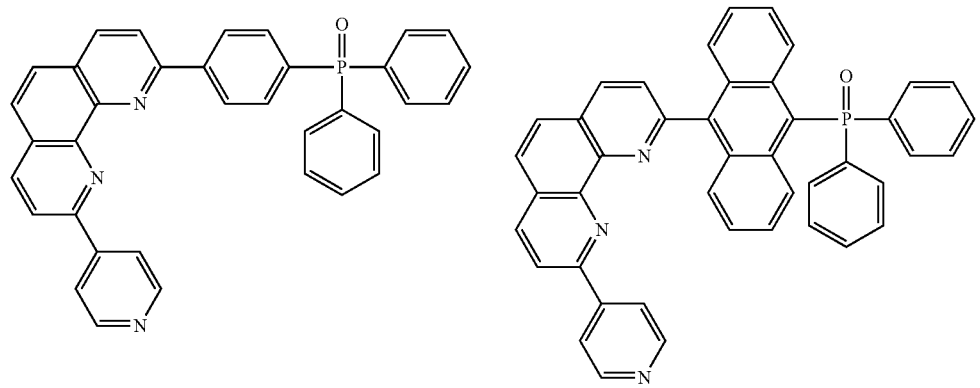

-continued
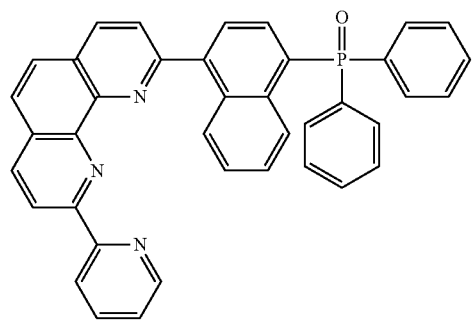
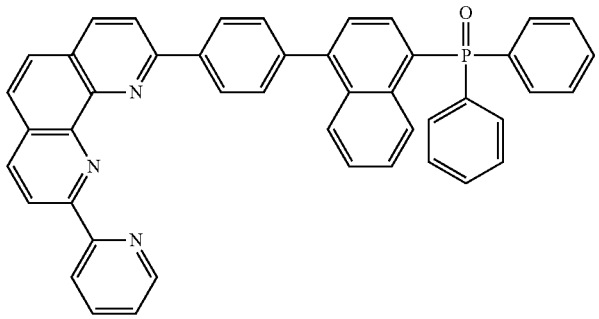
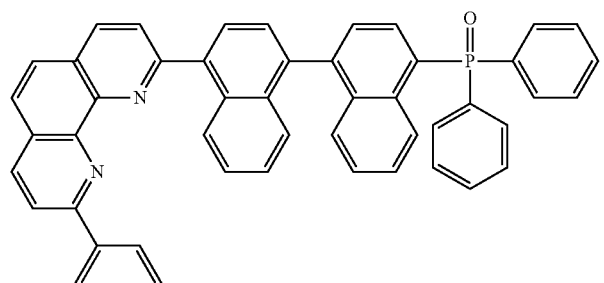
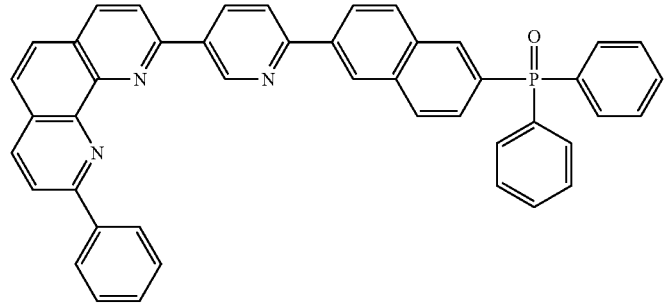
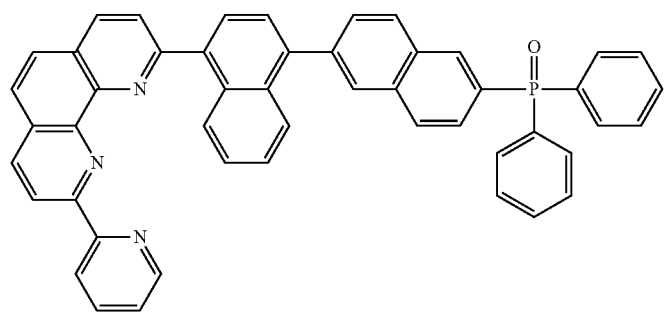
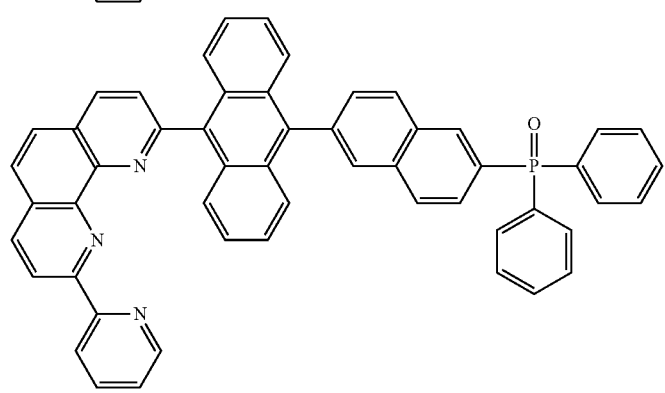

-continued

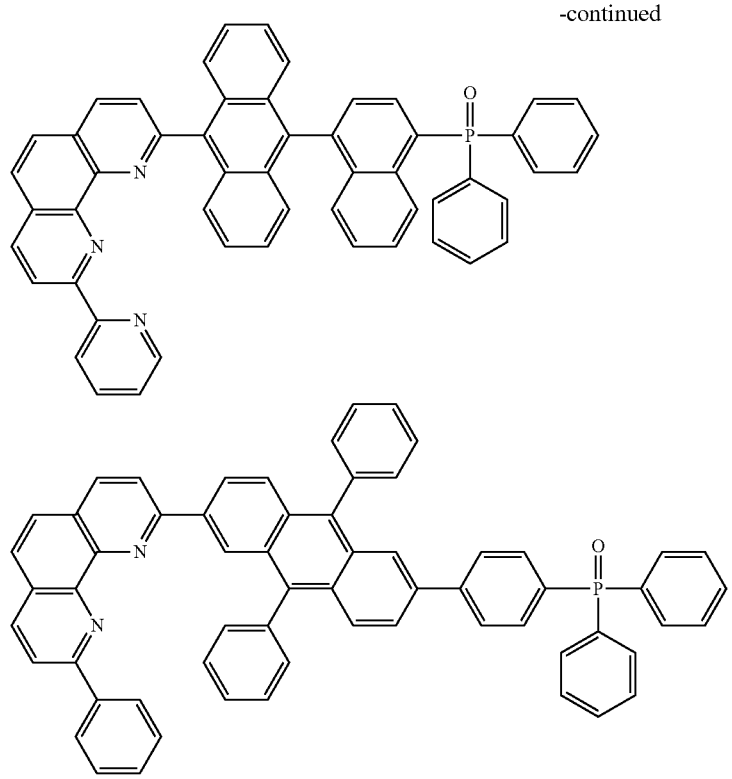

Since the organic compound of the present invention includes the phenanthroline core having two nitrogen atoms, which have a rich electron property, and the phosphine oxide moiety, which has excellent electron transporting property and excellent thermal stability, the electron transporting property of the organic compound of the present invention is improved. In addition, since the phenanthroline core (or moiety) has excellent combination property to the p-type dopant, i.e., the alkali metal, in the ETL or N-type CGL, the carrier in the cathode or the N-type CGL is efficiently transported or injected into the EML or the ETL. For example, when the organic compound is used for the ETL of the organic light emitting diode and the OLED device, the electron is efficiently transferred from the cathode into the EML such that the driving voltage is reduced, and the lifetime and the emitting efficiency are improved.

Moreover, since the organic compound is combined with the alkali metal or the alkali earth metal in the ETL or the N-type CGL, the diffusion of the alkali metal or the alkali earth metal into the EML or the P-type CGL is prevented. Further, since the nitrogen atom of the phenanthroline core in the organic compound is combined or bonded with the alkali metal or the alkali earth metal as a dopant in the ETL or an N-type charge generation layer (CGL) to form a gap state, the electron transporting property of the ETL or the N-type CGL is further improved.

As mentioned above, in the organic compound of the present invention, the phosphine oxide moiety, which has excellent electron transporting property and thermal stability, and the phenanthroline core, which has nitrogen atoms, are connected to each other. Accordingly, the organic compound is used for a layer of the organic light emitting diode requiring the electron transporting property and/or the electron injection property.

FIG. 1 is a schematic cross-sectional view of an organic light emitting diode according to a first embodiment of the present invention.

As shown in FIG. 1, the organic light emitting diode D1 includes a first electrode 180, a second electrode 184, an organic emitting layer 182 (e.g., an organic material layer or an emitting part) between the first and second electrodes 180 and 184. The organic emitting layer 182 includes a hole injection layer (HIL) 210, a hole transporting layer (HTL) 220, an emitting material layer (EML) 230, an electron transporting layer (ETL) 240 and an electron injection layer (EIL) 250 sequentially stacked on the first electrode 180. Namely, the organic light emitting diode D1 of the first embodiment of the present invention includes a single emitting part.

The first electrode 180 is the anode for injecting a hole and includes a high work function conductive material, e.g., indium-tin-oxide (ITO), indium-zinc-oxide (IZO) or zinc oxide (ZnO). The second electrode 184 is the cathode for injecting an electron and includes a low work function conductive material, e.g., aluminum (Al), magnesium (Mg) or Al—Mg alloy.

The HIL 210 is positioned between the first electrode 180 and the HTL 220. An interface property between the first electrode 180 of an inorganic material and the HTL 220 of an organic material is improved by the HIL 210. For example, the HIL 210 may include one of 4,4',4"-tris(3-methylphenylphenylamino)triphenylamine (MTDATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB or NPD), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiophene)polystyrene sulfonate (PEDOT/PSS), 2,3,5,6-tetrafluoro-7,7,8,8-tetracyanoquinodimethane (F4TCNQ) and N-(biphenyl-4-yl)-9,9-dimethyl-N-(4-(9-phenyl-9H-carbazol-3-yl)phenyl)-9H-fluoren-2-amine.

The HIL 210 may have a thickness of about 1 to 150 nm. The hole injection property may be improved with the thickness above 1 nm, and an increase of the driving voltage resulting from an increase of the thickness of the HIL 210 may be prevented with the thickness below 150 nm. The HIL 210 may be omitted.

The HTL 220 is positioned between the HIL 210 and the EML 230. For example, the HTL 220 may include a hole transporting material such as N,N'-diphenyl-N,N'-bis(3-methylphenyl)-1,1'-biphenyl-4,4'-diamine (TPD), MTDATA, TCTA, NPD or 4,4'-bis(N-carbazolyl)-1,1'-biphenyl (CBP). The HIL 220 may have a double-layered structure of different hole transporting materials.

The HTL 220 may have a thickness of about 1 to 150 nm. The hole transporting property may be improved with the thickness above 1 nm, and an increase of the driving voltage resulting from an increase of the thickness of the HTL 220 may be prevented with the thickness below 150 nm.

The EML 230 may include a host and a dopant. For example, when the EML 230 emits the blue light, a fluorescent host, such as anthracene derivative, pyrene derivative or perylene derivative, and a fluorescent dopant are used for the EML 230.

For example, the fluorescent host for the EML 230 may be selected from the group consisting of 4,4'-bis(2,2'-diphenylyinyl)-1,1'-biphenyl (DPVBi), 9,10-di-(2-naphtyl)anthracene (ADN), 2,5,8,11-tetra-t-butylperylene (TBADN), 2-tert-butyl-9,10-di(2-naphthyl)anthracene, 2-methyl-9,10-di(2-naphtyl)anthracene (MADN) and 2,2',2"-(1,3,5-benzinetriyl)-tris(1-phenyl-1-H-benzimidazole) (TBPi).

For example, the fluorescent dopant for the EML 230 may be selected from the group consisting of 4,4'-bis(9-ethyl-3-carbazovinylene)-1,1'-biphenyl (BCzVBi), 2,5,8,11-tetra (tert-butyl)perylene (TBP) and diphenyl-[4-(2-[1,1;4,1]terphenyl-4-yl-vinyl)-phenyl]-amine (BD-1).

When the EML 230 emits the green light or the red light, the EML 230 may include a phosphorescent host, e.g., carbazole derivative, and a phosphorescent dopant, e.g., a metal (iridium) complex. The dopant may have a weight % of about 1 to about 30 with respect to the host.

The ETL 240 is positioned between the EML 230 and the second electrode 184, and the EIL 250 is positioned between the ETL 240 and the second electrode 184.

The ETL 240 includes the organic compound of the present invention. In addition, the ETL 240 may further include a metal, e.g., an alkali metal or an alkali earth metal. The metal as a dopant in the ETL 240 may have a weight % of about 1 to about 30 with respect to the organic compound, but it is not limited thereto. For example, the alkali metal may include Li, Na, K and Cs, and the alkali earth metal may include Mg, Sr, Ba and Ra. But, it is not limited thereto. The ETL 240 may have a single-layered structure or multi-layered structure.

The ETL 240 may have a thickness of about 1 to 150 nm. The electron transporting property may be improved with the thickness above 1 nm, and an increase of the driving voltage resulting from an increase of the thickness of the ETL 240 may be prevented with the thickness below 150 nm.

An electron injection is improved by the EIL 250. The EIL 250 may include an alkali halide material, e.g., LiF, NaF, KF, RbF, CsF, FrF, BeF$_2$, MgF$_2$, CaF$_2$, SrF$_2$, BaF$_2$ or RaF$_2$, or an organic material, e.g., lithium quinolate (Liq), lithium benzoate, sodium stearate, tris-(8-hydroxyquinoline aluminum (Alq3), bis(8-hydroxy-2-methylquinoline)-4(4-phenylphenoxy)aluminum (BAlq), 2-biphenyl-4-yl-5-(4-t-butylphenyl)-1,3,4-oxadiazole (PBD), spiro-PBD or 3-(biphenyl-4-yl)-5-(4-tertbutylphenyl)-4-phenyl-4H-1,2,4-triazole (TAZ), but it is not limited thereto. The EIL 250 may be omitted.

Alternatively, the EIL 250 may include the organic compound of the present invention. In addition, the EIL 250 may further include a metal, e.g., an alkali metal or an alkali earth metal. The metal as a dopant in the EIL 250 may have a weight % of about 1 to about 30 with respect to the organic compound, but it is not limited thereto.

The EIL 250 may have a thickness of about 1 to 50 nm. The electron injection property may be improved with the thickness above 1 nm, and an increase of the driving voltage resulting from an increase of the thickness of the EIL 250 may be prevented with the thickness below 50 nm.

The organic compound of the present invention includes a phenanthroline core, which has a nitrogen atom of a relatively electron rich $sp^2$ hybrid orbital, and a phosphine oxide moiety, which has an excellent electron transporting property and an excellent thermal stability. The electron transporting property of the organic compound of the present invention is improved based on the chemical structure of the organic compound. Accordingly, when the organic compound is used for the ETL of the organic light emitting diode and the OLED device, the driving voltage is reduced, and the lifetime and the emitting efficiency are improved.

On the other hand, the organic compound of the present invention may be applied to a tandem structure organic light emitting diode emitting the white light. The tandem structure white organic light emitting diode may be used for a lighting apparatus, a thin light source, a backlight unit of a liquid crystal display device and a full color display device including a color filter.

In the white organic light emitting diode, properties of color purity and color stability as well as an emitting efficiency and a lifetime are important facts. For example, the white organic light emitting diode may be classified into a single-layered emission structure and a multi-layered emission structure. To provide the long lifetime white organic light emitting diode, the white organic light emitting diode having a stack structure of at least two emitting parts may be used. This structure may be referred to as the tandem structure.

Figure 2:
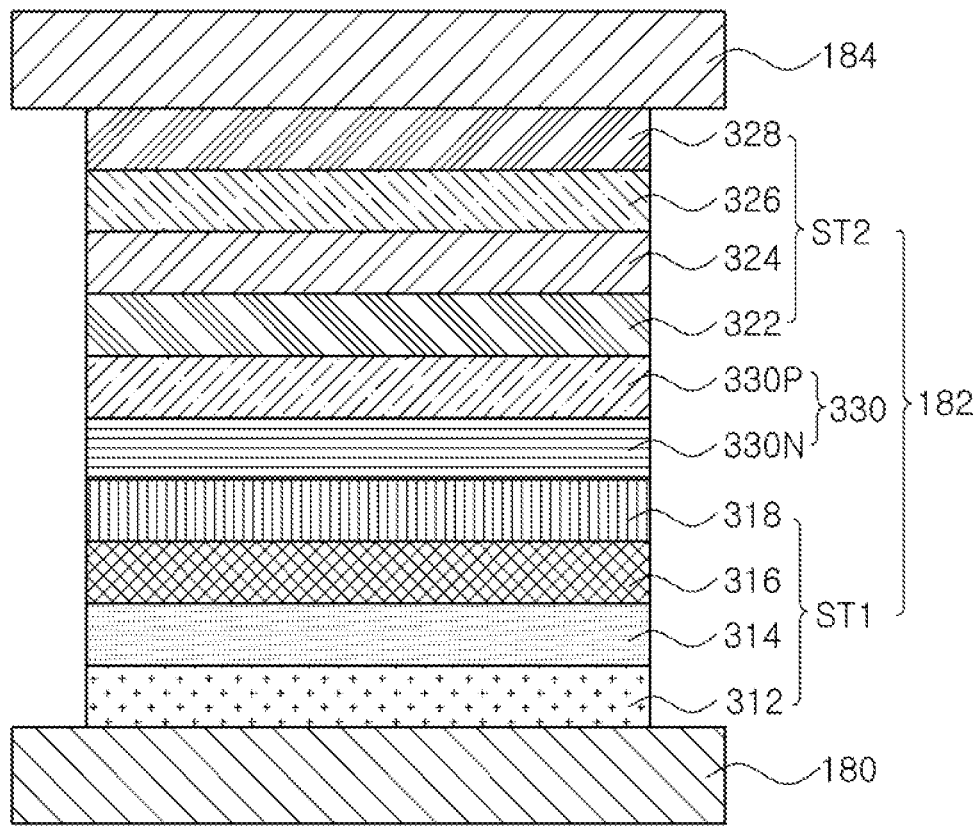
FIG. 2 is a schematic cross-sectional view of an organic light emitting diode according to a second embodiment of the present invention.

FIG. 2 is a schematic cross-sectional view of an organic light emitting diode according to a second embodiment of the present invention.

As shown in FIG. 2, the organic light emitting diode D2, which includes two emitting parts, includes a first electrode 180, a second electrode 184, an organic emitting layer 182 between the first and second electrodes 180 and 184 and including first and second emitting parts ST1 and ST2 and a charge generation layer (CGL) 330.

The first electrode 180 is the anode for injecting a hole and includes a high work function conductive material, e.g., ITO, IZO or ZnO. The second electrode 184 is the cathode for injecting an electron and includes a low work function conductive material, e.g., Al, Mg or Al—Mg alloy.

The CGL 330 is positioned between the first and second emitting parts ST1 and ST2. Namely, the first emitting part ST1, the CGL 330 and the second emitting part ST2 are sequentially stacked on the first electrode 180. In other words, the first emitting part ST1 is positioned between the first electrode 180 and the CGL 330, and the second emitting part ST2 is positioned between the second electrode 184 and the CGL 330.

The first emitting part ST1 may include an HIL 312, a first HTL 314, a first EML 316 and a first ETL 318 sequentially stacked on the first electrode 180. Namely, the HIL 312 and the first HTL 314 are positioned between the first electrode 180 and the first EML 316. The HIL 312 is positioned between the first electrode 180 and the first HTL 314, and the first HTL 314 is positioned between the HIL 312 and the first EML 316. In addition, the first ETL 318 is positioned between the first EML 316 and the CGL 330.

A hole injection from the first electrode 180 into the first EML 316 is improved by the HIL 312. The HIL 312 may include at least one selected from the group consisting of MTDATA, CuPc, TCTA, NPD, HATCN, TDAPB, PEDOT/PSS, F4TCNQ and N-(biphenyl-4-yl)-9,9-dimethyl-N-(4-(9-phenyl-9H-carbazole-3-yl)phenyl)-9H-fluorene-2amine.

The HIL 312 may have a thickness of about 1 to 150 nm. The hole injection property may be improved with the thickness above 1 nm, and an increase of the driving voltage resulting from an increase of the thickness of the HIL 312 may be prevented with the thickness below 150 nm. The HIL 312 may be omitted according to the structure or property of the organic light emitting diode.

A hole transporting is improved by the first HTL 314. The first HTL 314 may include at least one selected from a group consisting of TPD, TCTA, MTDATA, NPD and CBP, but it is not limited thereto. The first HTL 314 may have a single-layered structure or a multi-layered structure.

The first HTL 314 may have a thickness of about 1 to 150 nm. The hole transporting property may be improved with the thickness above 1 nm, and an increase of the driving voltage resulting from an increase of the thickness of the first HTL 314 may be prevented with the thickness below 150 nm.

The first EML 316 may be a blue EML. Alternatively, the first EML 316 may be a red EML, a green EML or a yellow EML. When the first EML 316 is the blue EML, the first EML 316 may be a blue EML, a dark blue EML or a sky blue EML. In addition, the first EML 316 may be a double-layered structure of the blue EML and the red EML, the blue EML and yellow-green EML, or the blue EML and the green EML.

When the first EML 316 is the red EML, the first EML 316 may be a phosphorescent EML including a host, e.g., 4,4'-bis(carbazol-9-yl)biphenyl (CBP), and at least one dopant selected from the group consisting of bis(1-phenylisoquinoline)acetylacetonate iridium (PIQIr(acac), bis(1-phenylquinoline)acetylacetonate iridium(PQIr(acac) and tris(1-phenylquinoline)iridium(PQIr) and octaethylporphyrin platinum (PtOEP), but it is not limited thereto. Alternatively, the first EML 316 may be a fluorescent EML including PBD:Eu(DBM)$_3$(Phen) or perylene. In this instance, the first emitting part ST1 has an emission peak range of about 600 to 650 nm.

When the first EML 316 is the green EML, the first EML 216 may be a phosphorescent EML including a host, e.g., CBP, and a dopant of iridium complex, but it is not limited thereto. Alternatively, the first EML 316 may a fluorescent EML including tris(8-hydroxyquinolinato)aluminum (Alq$_3$). In this instance, the first emitting part ST1 has an emission peak range of about 510 to 570 nm.

When the first EML 316 is the blue EML, the first EML 316 may be a phosphorescent EML including a host, e.g., CBP, and a dopant of iridium complex, but it is not limited thereto. Alternatively, the first EML 316 may a fluorescent EML including spiro-DPVBi, Spiro-CBP, distyryl benzene (DSB), distyryl arene (DSA), PFO-based polymer or PPV-based polymer. As mentioned above, the first EML 316 may be a sky blue EML or deep blue (dark blue) EML. In this instance, the first emitting part ST1 has an emission peak range of about 440 to 480 nm.

On the other hand, to improve the emitting efficiency (red efficiency), the first emitting part ST1 may include two EMLs. For example, the first emitting part ST1 may include the blue EML and the red EML. In this instance, the first emitting part ST1 has an emission peak range of about 440 to 650 nm.

In addition, the first EML 316 may have a single-layered structure of the yellow-green EML or a double-layered structure of the yellow-green EML and the green EML. In this instance, the first EML 316 may include at least one host selected from a group consisting of CBP and bis(2-methyl-8-quinolinolate)-4-(phenylphenolato)aluminium (BAlq) and a phosphorescent yellow-green dopant. The first emitting part ST1 has an emission peak range of about 510 to 590 nm.

When the first emitting part ST1 includes two EMLs of the yellow-green EML and the red EML to improve the emitting efficiency (red efficiency), the first emitting part ST1 has an emission peak range of about 510 to 650 nm.

An electron transporting is improved by the first ETL 318. The first ETL 318 may include an organic compound represented by Formula 1, and a metal, e.g., an alkali metal or an alkali earth metal, may be doped into the organic compound.

The first ETL 318 may have a thickness of about 1 to 150 nm. The electron transporting property may be improved with the thickness above 1 nm, and an increase of the driving voltage resulting from an increase of the thickness of the first ETL 318 may be prevented with the thickness below 150 nm.

The second emitting part ST2 may include a second HTL 322, a second EML 324, a second ETL 326 and an EIL 328. The second HTL 322 is positioned between the CGL 330 and the second EML 324, and the second ETL 326 is positioned between the second EML 324 and the second electrode 184. In addition, the EIL 328 is positioned between the second ETL 326 and the second electrode 184.

The second HTL 322 and the second ETL 326 may be same as or different from the first HTL 314 and the first ETL 318 in the first emitting part ST1, respectively. The EIL 328 may be omitted according to the structure or property of the organic light emitting diode.

The second EML 324 may be red, green, blue or yellow-green EML. For example, when the first EML 316 is the blue EML, the second EML 324 may be yellow-green EML. Alternatively, the first EML 316 may be the yellow-green EML, and the second EML 324 may be the blue EML.

When the second EML 324 is the yellow-green EML, the second EML 324 may have a single-layered structure of the yellow-green EML or a double-layered structure of the yellow-green EML and the green EML.

For example, the single-layered second EML 324 may include at least one host selected from a group consisting of CBP and bis(2-methyl-8-quinolinolate)-4-(phenylphenolato)aluminium (BAlq) and a phosphorescent yellow-green dopant, but it is not limited thereto.

An electron transporting is improved by the second ETL 326. The second ETL 326 may include an organic compound represented by Formula 1, and a metal, e.g., an alkali metal or an alkali earth metal, may be doped into the organic compound.

The second ETL 326 may have a thickness of about 1 to 150 nm. The electron transporting property may be improved with the thickness above 1 nm, and an increase of the driving voltage resulting from an increase of the thickness of the second ETL 326 may be prevented with the thickness below 150 nm.

An electron injection is improved by the EIL 328. The EIL 328 may include an alkali halide material, e.g., LiF, NaF, KF, RbF, CsF, FrF, BeF$_2$, MgF$_2$, CaF$_2$, SrF$_2$, BaF$_2$ or RaF$_2$, or an organic material, e.g., lithium quinolate (Liq), lithium benzoate, sodium stearate, tris-(8-hydroxyquinoline aluminum (Alq3), bis(8-hydroxy-2-methylquinoline)-4(4-phenylphenoxy)aluminum (BAlq), 2-biphenyl-4-yl-5-(4-t-butylphenyl)-1,3,4-oxadiazole (PBD), spiro-PBD or 3-(biphenyl-4-yl)-5-(4-tertbutylphenyl)-4-phenyl-4H-1,2,4-triazole (TAZ), but it is not limited thereto. The EIL 328 may be omitted.

Alternatively, the EIL 328 may include the organic compound of the present invention. In addition, the EIL 328 may further include a metal, e.g., an alkali metal or an alkali earth metal. The metal as a dopant in the EIL 328 may have a weight % of about 1 to about 30 with respect to the organic compound, but it is not limited thereto.

The EIL 328 may have a thickness of about 1 to 50 nm. The electron injection property may be improved with the thickness above 1 nm, and an increase of the driving voltage resulting from an increase of the thickness of the EIL 328 may be prevented with the thickness below 50 nm.

In the tandem structure organic light emitting diode D2, to increase the current efficiency generating from each of the EMLs 316 and 324 and efficiently distribute the charge, the CGL 330 is positioned between the first emitting part ST1 and the second emitting part ST2. Namely, the first and second emitting parts ST1 and ST2 are connected by the CGL 330. The CGL 330 may be a P—N junction type CGL including an N-type CGL 330N and a P-type CGL 330P.

The N-type CGL 330N is positioned between the first ETL 318 and the second HTL 322, and the P-type CGL 330P is positioned between the N-type CGL 330N and the second HTL 322. The CGL 330 generates a charge or separates a charge into a hole and an electron such that the hole and the electron are provided into the first and second emitting parts ST1 and ST2.

The N-type CGL 330N provides the electron into the first ETL 318 of the first emitting part ST1, and the first ETL 318 provide the electron into the first EML 316 of the first emitting part ST1. On the other hand, the P-type CGL 330P provide the hole into the second HTL 322 of the second emitting part ST2, and the second HTL 322 provide the hole into the second EML 324 of the second emitting part ST2.

The P-type CGL may include an organic material and a dopant, e.g., a metal or a p-type dopant. For example, the metal as the dopant may be selected from the group consisting of Al, Cu, Fe, Pb, Zn, Au, Pt, W, In, Mo, Ni, Ti and their alloy. In addition, the generally known materials may be used as the p-type dopant and the organic material. For example, the p-type dopant may be selected from the group consisting of F$_4$-TCNQ, iodine, FeCl$_3$, FeF$_3$ and SbCl$_5$, and the organic material may be selected from the group consisting of NPB, TPD, N,N,N',N'-tetranaphthalenyl-benzidine (TNB) and HAT-CN.

In the tandem structure organic light emitting diode, when the electrons are transported from the N-type CGL 330N into the first ETL 318, the driving voltage is increased because of a lowest unoccupied molecular orbital (LUMO) energy level difference between each of the first ETL 318 and the N-type CGL 330N.

To overcome the above problem, at least one of the first ETL 318 and the N-type CGL 330N includes an organic compound represented in Formula 1 (or Formula 2). In addition, each of the first ETL 318 and the N-type CGL 330N may further include alkali metal or alkali earth metal as a dopant.

By doping the alkali metal or the alkali earth metal into the first ETL 318 and/or the N-type CGL 330N, the electron transporting/injection property may be further improved. For example, when the alkali metal or the alkali earth metal is doped into the N-type CGL 330N, the organic compound is combined or bonded with the alkali metal or the alkali earth metal in the N-type CGL 330 to form a gap state. As a result, the energy difference between the N-type CGL 330N and the P-type CGL 330P is decreased such that an electron transporting/injection property from the N-type CGL 330N into the first ETL 318 is improved. The alkali metal or the alkali earth metal may have a weight % of about 1 to 30 with respect to the organic compound, but it is not limited thereto. Instead of the alkali metal or the alkali earth metal, an alkali halide material, e.g., LiF, NaF, KF, RbF, CsF, FrF, BeF$_2$, MgF$_2$, CaF$_2$, SrF$_2$, BaF$_2$ or RaF$_2$, may be doped.

Since the organic compound of the present invention includes the phenanthroline core, which has the nitrogen atom of a relatively electron rich sp$^2$ hybrid orbital, and the phosphine oxide moiety, which has excellent electron transporting property and excellent thermal stability, the electron transporting property of the organic compound of the present invention is improved. Accordingly, the charge generated in the N-type CGL is efficiently transported into the first ETL 318.

In addition, since the nitrogen atom of the phenanthroline core in the organic compound is combined or bonded with the alkali metal or the alkali earth metal as a dopant in the N-type CGL to form a gap state, the electron transporting property of the N-type CGL into the first ETL is further improved. Moreover, since the organic compound is combined with the alkali metal or the alkali earth metal in the N-type CGL, the diffusion of the alkali metal or the alkali earth metal into the P-type CGL is prevented. Accordingly, when the organic compound is used for the N-type CGL in a tandem structure light emitting diode or OLED device, the electron is efficiently transferred from the N-type CGL into the first ETL, the driving voltage is reduced, and the lifetime and the emitting efficiency are improved.

Figure 3:
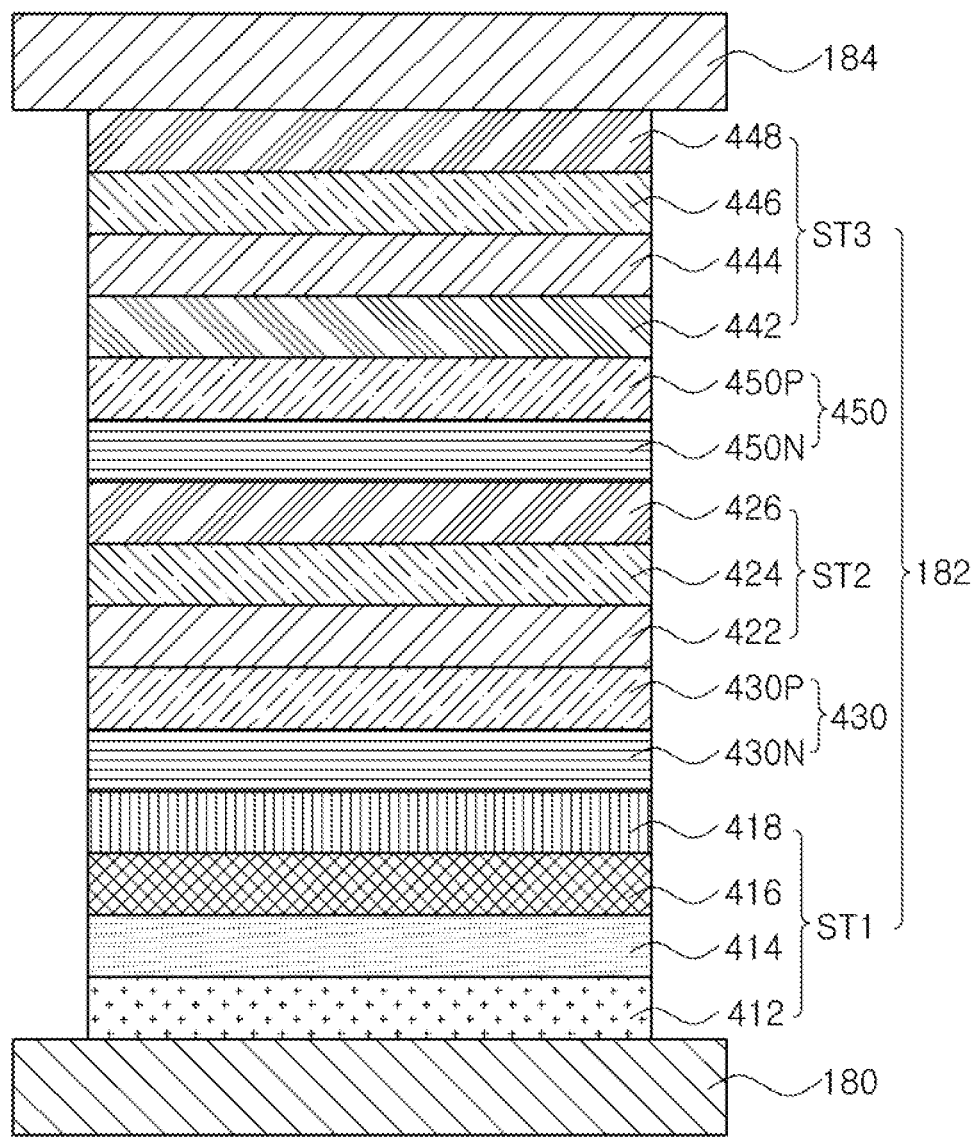
FIG. 3 is a schematic cross-sectional view of an organic light emitting diode according to a third embodiment of the present invention.

FIG. 3 is a schematic cross-sectional view of an organic light emitting diode according to a third embodiment of the present invention.

Referring to FIG. 3, an organic light emitting diode D3 includes a first electrode 180, a second electrode 184, an organic emitting layer 182 between the first and second electrodes 180 and 184 and including first to third emitting parts ST1, ST2 and ST3 and first and second CGLs 430 and 450. Alternatively, four or more emitting parts and three or more CGLs may be disposed between the first and second electrodes 180 and 184.

As mentioned above, the first electrode 180 is the anode for injecting a hole and includes a high work function conductive material, e.g., ITO, IZO or ZnO. The second electrode 184 is the cathode for injecting an electron and includes a low work function conductive material, e.g., Al, Mg or Al—Mg alloy.

The first and second CGLs 430 and 450 are positioned between the first and second emitting parts ST1 and ST2 and the second and third emitting parts ST2 and ST3, respectively. Namely, the first emitting part ST1, the first CGL 430, the second emitting part ST2, the second CGL 450 and the third emitting part ST3 are sequentially stacked on the first electrode 180. In other words, the first emitting part ST1 is positioned between the first electrode 180 and the first CGL 430, and the second emitting part ST2 is positioned between the First and Second CGLs 430 and 450. In addition, the third emitting part ST3 is positioned between the second electrode 184 and the second CGL 450.

The first emitting part ST1 may include an HIL 412, a first HTL 414, a first EML 416 and a first ETL 418 sequentially stacked on the first electrode 180. Namely, the HIL 412 and the first HTL 414 are positioned between the first electrode 180 and the first EML 416, and the HIL 412 is positioned between the first electrode 180 and the first HTL 414. In addition, the first ETL 418 is positioned between the first EML 416 and the first CGL 430.

The HIL 412, the first HTL 414, the first EML 416 and the first ETL 418 may have substantially the same property and structure as those in FIG. 2. For example, the first EML 416 may be a blue EML such that the first emitting part ST1 may have an emission peak range of about 440 to 480 nm.

The second emitting part ST2 may include a second HTL 422, a second EML 424 and a second ETL 426. The second HTL 422 is positioned between the first CGL 430 and the second EML 424, and the second ETL 426 is positioned between the second EML 424 and the second CGL 450.

The second HTL 422, second EML 424 and the second ETL 426 may have substantially the same property and structure as those in FIG. 2. For example, the second EML 424 may be a yellow-green EML such that the second emitting part ST2 may have an emission peak range of about 510 to 590 nm.

The third emitting part ST3 may include a third HTL 442, a third EML 444, a third ETL 446 and an EIL 448. The third HTL 442 is positioned between the second CGL 450 and the third EML 444, and the third ETL 446 is positioned between the third EML 444 and the second electrode 184. In addition, the EIL 448 is positioned between the third ETL 446 and the second electrode 184.

The third HTL 442, the third ETL 446 and the EIL 448 may have substantially the same property and structure as the second HTL 422, the second ETL 426 and the EIL 428 in FIG. 2.

The third EML 444 may have substantially the same property as the first EML 416 or the second EML 424. For example, the third EML 444 may be a blue EML such that the third emitting part ST3 may have an emission peak range of about 440 to 480 nm.

The first CGL 430 is positioned between the first emitting part ST1 and the second emitting part ST2, and the second CGL 450 is positioned between the second emitting part ST2 and the third emitting part ST3. Each of the first and second CGLs 430 and 450 may be a P—N junction type CGL. The first CGL 430 includes an N-type CGL 430N and a P-type CGL 430P, and the second CGL 450 includes an N-type CGL 450N and a P-type CGL 450P.

In the first CGL 430, the N-type CGL 430N is positioned between the first ETL 418 and the second HTL 422, and the P-type CGL 430P is positioned between the N-type CGL 430N and the second HTL 422.

In the second CGL 450, the N-type CGL 450N is positioned between the second ETL 426 and the third HTL 442, and the P-type CGL 450P is positioned between the N-type CGL 450N and the third HTL 442.

Each of the first and second CGLs 430 and 450 generates a charge or separates a charge into a hole and an electron such that the hole and the electron are provided into the first to third emitting parts ST1 to ST3.

Namely, in the first CGL 430, the N-type CGL 430N provides the electron into the first ETL 418 of the first emitting part ST1, and the P-type CGL 430P provide the hole into the second HTL 422 of the second emitting part ST2. In addition, in the second CGL 450, the N-type CGL 450N provides the electron into the second ETL 426 of the second emitting part ST2, and the P-type CGL 450P provide the hole into the third HTL 442 of the third emitting part ST3.

Each of the P-type CGLs 430P and 450P may include an organic material and a dopant, e.g., a metal or a p-type dopant. For example, the metal as the dopant may be selected from the group consisting of Al, Cu, Fe, Pb, Zn, Au, Pt, W, In, Mo, Ni, Ti and their alloy. In addition, the generally known materials may be used as the p-type dopant and the organic material. For example, the p-type dopant may be selected from the group consisting of $F_4$-TCNQ, iodine, $FeCl_3$, $FeF_3$ and $SbCl_5$, and the organic material may be selected from the group consisting of NPB, TPD, N,N, N',N'-tetranaphthalenyl-benzidine (TNB) and HAT-CN.

When the electrons are transported from the N-type CGLs 430N and 450N into the first and second ETLs 418 and 426, the driving voltage is increased because of a lowest unoccupied molecular orbital (LUMO) energy level difference between each of the first and second ETLs 418 and 426 and each of the N-type CGLs 430N and 450N.

To overcome the above problem, at least one of the first and second ETLs 418 and 426 and the N-type CGLs 430N and 450N includes an organic compound represented in Formula 1 (or Formula 2). In addition, each of the first and second ETLs 418 and 426 and the N-type CGLs 430N and 450N may further include alkali metal or alkali earth metal as a dopant. The alkali metal or the alkali earth metal may have a weight % of about 1 to 30 with respect to the organic compound, but it is not limited thereto. Instead of the alkali metal or the alkali earth metal, an alkali halide material, e.g., LiF, NaF, KF, RbF, CsF, FrF, $BeF_2$, $MgF_2$, $CaF_2$, $SrF_2$, $BaF_2$ or $RaF_2$, may be doped.

The organic compound of the present invention preferably includes a phenanthroline core, which has a nitrogen atom of a relatively electron rich $sp^2$ hybrid orbital, and a phosphine oxide moiety, which has an excellent electron transporting property and an excellent thermal stability. The electron transporting property of the organic compound of the present invention is improved based on the chemical structure of the organic compound. Accordingly, the charge generated in the N-type CGLs is efficiently transported into the ETLs.

In addition, since the nitrogen atom of the phenanthroline core in the organic compound is combined or bonded with the alkali metal or the alkali earth metal as a dopant in the N-type CGLs to form a gap state, the electron transporting property of the N-type CGLs into the ETLs is further improved. Moreover, since the organic compound is combined with the alkali metal or the alkali earth metal in the N-type CGLs, the diffusion of the alkali metal or the alkali earth metal into the P-type CGLs is prevented. Accordingly, when the organic compound is used for the N-type CGLs in a tandem structure light emitting diode or OLED device, the electron is efficiently transferred from the N-type CGLs into the ETLs, the driving voltage is reduced, and the lifetime and the emitting efficiency are improved.

Figure 4:
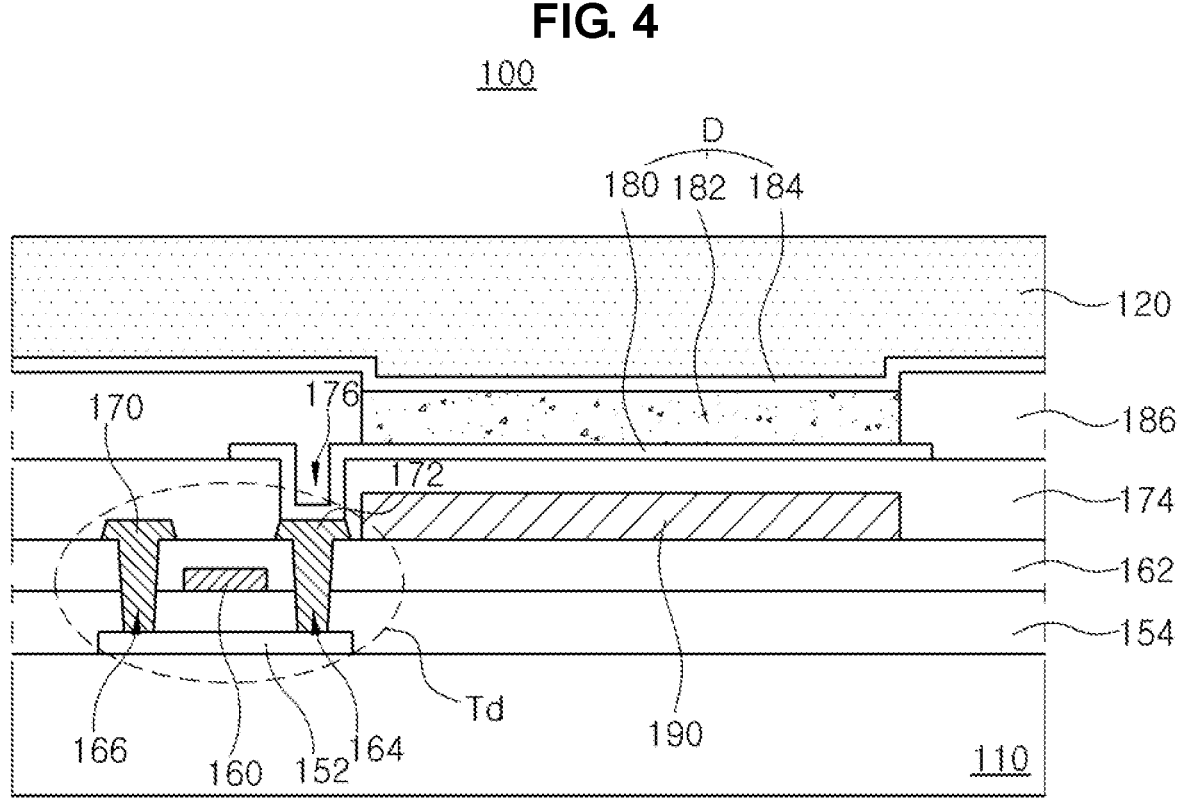
FIG. 4 is a schematic cross-sectional view of an OLED device according to an embodiment of the present invention.
Figure 5A:
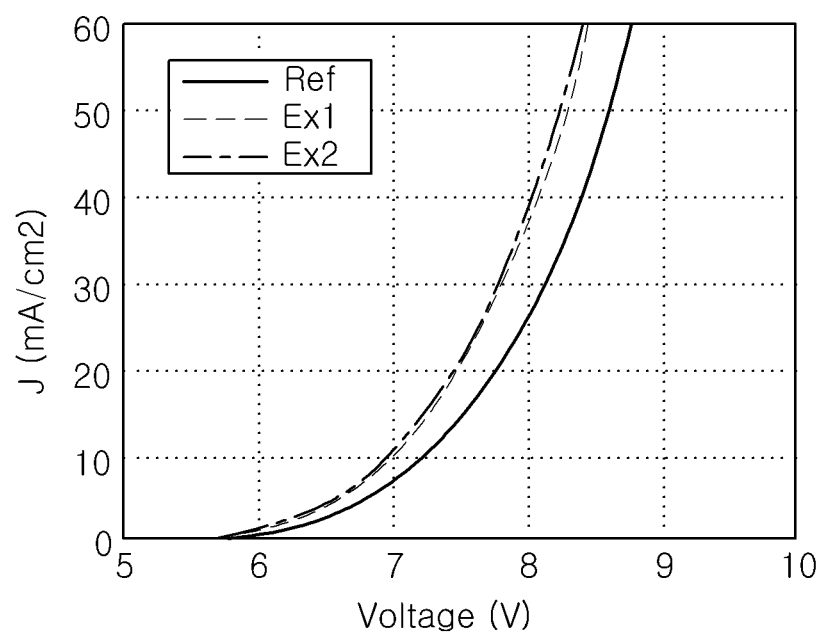
FIGS. 5A to 5D are graphs showing emitting properties of an organic light emitting diode including an organic compound in an N-type CGL according to an embodiment of the present invention.
Figure 5B:
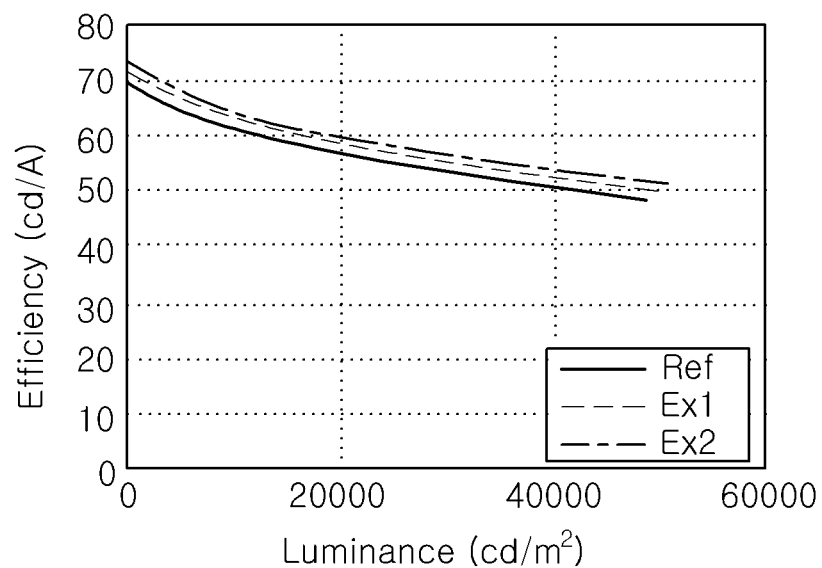
Figure 5C:
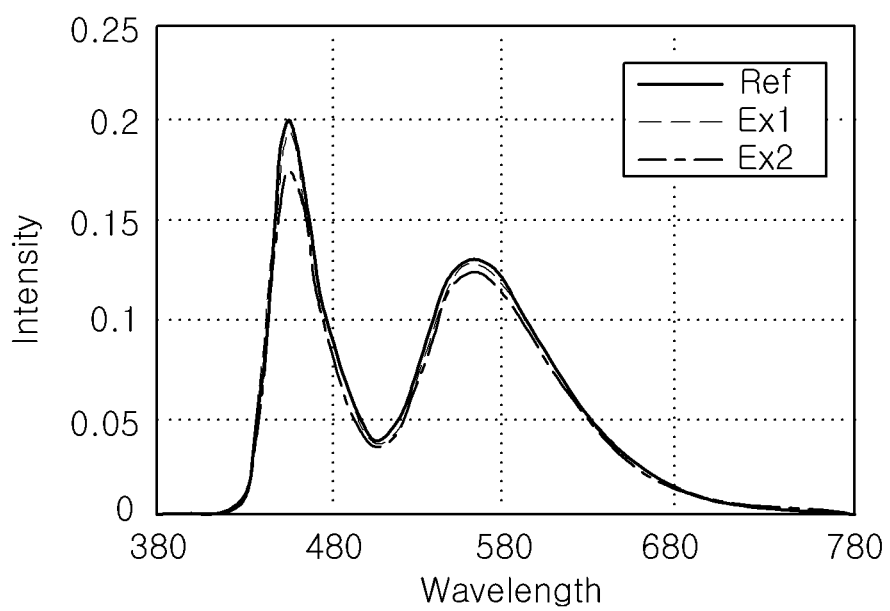
Figure 5D:
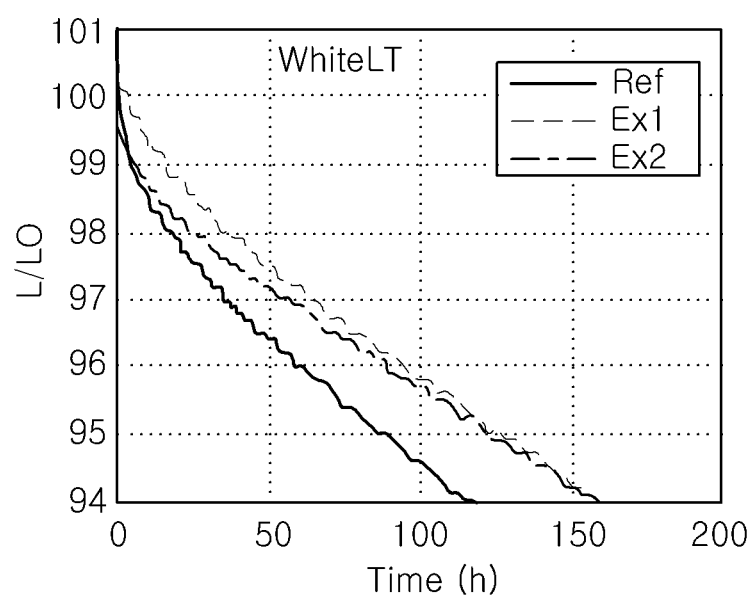

FIG. 4 is a schematic cross-sectional view of an OLED device according to an embodiment of the present invention. All the components of the OLED device as well as the organic light emitting diode according to all embodiments of the present invention are operatively coupled and coupled.

As shown in FIG. 4, an OLED device 100 includes a substrate 110, an organic light emitting diode D over the substrate 110, an encapsulation film 120 covering the organic light emitting diode D.

A driving thin film transistor (TFT) Td is disposed on the substrate 110, and the organic light emitting diode D is connected to the driving TFT Td.

Further, a gate line and a data line are disposed on or over the substrate 110 and cross each other to define a pixel region. In addition, a power line, which is parallel to and spaced apart from the gate line or the data line, a switching TFT, which is electrically connected to the gate line and the data line, and a storage capacitor, which is connected to the power line and an electrode of the switching TFT may be formed on or over the substrate 110.

The driving TFT Td is connected to the switching TFT and includes a semiconductor layer 152, a gate electrode 160, a source electrode 170 and a drain electrode 172.

The semiconductor layer 152 is formed on the substrate 110. The semiconductor layer 152 may be formed of an oxide semiconductor material or a poly-silicon.

When the semiconductor layer 152 includes the oxide semiconductor material, a light-shielding pattern may be formed under the semiconductor layer 152. The light to the semiconductor layer 152 is shielded or blocked by the light-shielding pattern such that thermal degradation of the semiconductor layer 152 can be prevented. On the other hand, when the semiconductor layer 152 includes polycrystalline silicon, impurities may be doped into both sides of the semiconductor layer 152.

A gate insulating layer 154 is formed on the semiconductor layer 152. The gate insulating layer 154 may be formed of an inorganic insulating material such as silicon oxide or silicon nitride.

The gate electrode 160, which is formed of a conductive material, e.g., metal, is formed on the gate insulating layer 154 to correspond to a center of the semiconductor layer 152. The gate electrode 160 is connected to the switching TFT.

An interlayer insulating layer 162, which is formed of an insulating material, is formed on an entire surface of the substrate 110 including the gate electrode 160. The interlayer insulating layer 162 may be formed of an inorganic insulating material, e.g., silicon oxide or silicon nitride, or an organic insulating material, e.g., benzocyclobutene or photo-acryl.

The interlayer insulating layer 162 includes first and second contact holes 164 and 166 exposing both sides of the semiconductor layer 152. The first and second contact holes 164 and 166 are positioned at both sides of the gate electrode 160 to be spaced apart from the gate electrode 160.

The source electrode 170 and the drain electrode 172, which are formed of a conductive material, e.g., metal, are formed on the interlayer insulating layer 162. The source electrode 170 and the drain electrode 172 are spaced apart from each other with respect to the gate electrode 160 and respectively contact both sides of the semiconductor layer 152 through the first and second contact holes 164 and 166. The source electrode 170 is connected to the power line.

In the driving TFT Td, the gate electrode 160, the source electrode 170 and the drain electrode 172 are positioned over the semiconductor layer 152. Namely, the driving TFT Td has a coplanar structure.

Alternatively, in the driving TFT Td, the gate electrode may be positioned under the semiconductor layer, and the source and drain electrodes may be positioned over the semiconductor layer such that the driving TFT Td may have an inverted staggered structure. In this instance, the semiconductor layer may include amorphous silicon.

The switching TFT may have substantially the same structure as the driving TFT Td.

The OLED device 100 may further include a color filter 190. For example, the color filter 190 absorbs a part of the red, green and blue light. A red color filter pattern, a green color filer pattern and a blue color filter pattern may be disposed in each pixel region. Due to the color filter pattern 190, the OLED device 100 provides a full-color image.

In FIG. 4, the color filter 190 is positioned between the organic light emitting diode D and the interlayer insulating layer 162 (or the substrate 110). Namely, the OLED device 100 is the bottom-emission type. Alternatively, in the top-emission type OLED device, the color filter 190 may be positioned on or over the organic light emitting diode D, e.g., over the second electrode 184. For example, the color filter 190 may have a thickness of about 2 to 5 micrometers. The color filter 190 may be used with the tandem structure white organic light emitting diode D in FIG. 2 or FIG. 3.

A passivation layer 174, which includes a drain contact hole 176 exposing the drain electrode 172 of the driving TFT Td, is formed to cover the driving TFT Td and the color filter 190.

A first electrode 180, which is connected to the drain electrode 172 of the driving TFT Td through the drain contact hole 176, is separately formed on the passivation layer 174 in each pixel region.

The first electrode 180 may be an anode and may be formed of a conductive material having a relatively high work function. For example, the first electrode 180 may be formed of a transparent conductive material, such as ITO, IZO or ZnO.

When the OLED device 100 of the present invention is a top-emission type, a reflection electrode or a reflection layer may be formed under the first electrode 180. For example, the reflection electrode or the reflection layer may be formed of aluminum (Al), silver (Ag), nickel (Ni) or aluminum-palladium-copper (APC) alloy.

A bank layer 186, which covers edges of the first electrode 180, is formed on the passivation layer 174. The bank 186 exposes a center of the first electrode 180 in the pixel region.

An organic emitting layer 182 is formed on the first electrode 180. As explained below, the organic emitting layer includes a single emitting part or at least two emitting parts (the tandem structure).

A second electrode 184 is formed over the substrate 110 including the emitting layer 182. The second electrode 184 is positioned at an entire surface of the display area. The second electrode 184 may be a cathode and may be formed of a conductive material having a relatively low work function. For example, the second electrode 184 may be formed of Al, Mg or Al—Mg alloy.

The first electrode 180, the emitting layer 182 and the second electrode 184 constitute the organic light emitting diode D.

The encapsulation film 120 is formed on the organic light emitting diode D to prevent penetration of moisture into the organic light emitting diode D. For example, the encapsulation film 120 may have a triple-layered structure of a first inorganic layer, an organic layer and a second inorganic layer. However, it is not limited thereto.

The organic compound of the present invention includes a phenanthroline core, which has a nitrogen atom of a relatively electron rich $sp^2$ hybrid orbital, and a phosphine oxide moiety, which has an excellent electron transporting property and an excellent thermal stability. The electron transporting/injection property of the organic compound of the present invention is improved based on the chemical structure of the organic compound. Accordingly, when the ETL includes the organic compound, the electron is efficiently transported or injected into the EML. As a result, in the organic light emitting diode and/or the OLED device, the driving voltage is reduced, and the lifetime and the emitting efficiency are improved.

In addition, since the nitrogen atom of the phenanthroline core in the organic compound is combined or bonded with the alkali metal or the alkali earth metal as a dopant in the N-type CGL to form a gap state, the electron transporting property of the N-type CGL into the ETL is further improved. Moreover, since the organic compound is combined with the alkali metal or the alkali earth metal in the N-type CGL, the diffusion of the alkali metal or the alkali earth metal into the P-type CGL is prevented. Accordingly, when the organic compound is used for the N-type CGL in a tandem structure light emitting diode or OLED device, the electron is efficiently transferred from the N-type CGL into the first ETL, the driving voltage is reduced, and the lifetime and the emitting efficiency are improved.

Synthesis

1. Synthesis of 2-(10-(4-(diphenylphosphine oxide) phenyl)anthracen-9-yl)-1,10-phenanthroline

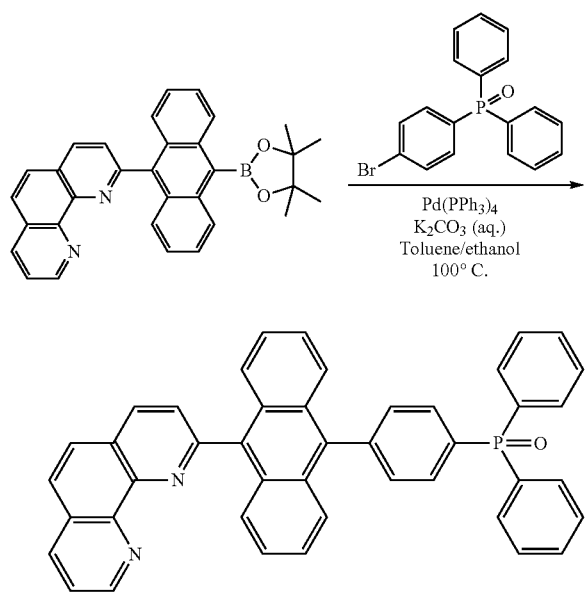

Under nitrogen conditions, (4-bromophenyl)diphenylphosphine oxide (10 g, 28.0 mmol), 2-(10-(4,4,5,5-tetramethyl-1,3,2-dioxaborolan-2-yl)anthracen-9-yl)-1,10-phenanthroline (16.2 g, 33.6 mmol), tetrakistriphenylphosphine palladium (0) (1.72 g, 1,49 mmol), 4M potassium carbonate aqueous solution (15 mL), toluene (200 mL) and ethanol (20 mL) were refluxed and stirred for 12 hrs. After completion of the reaction, the distilled water (50 mL) was added and stirred for 3 hrs. The mixture was filtered under reduced pressure and separated by column chromatography using methylene chloride (MC) and hexane as an eluent. The resultant was crystallized using MC such that the compound of 2-(10-(4-(diphenylphosphine oxide)phenyl)anthracen-9-yl)-1,10-phenanthroline (10 g, yield 70%) was obtained.

2. Synthesis of 2-(1-(4-(diphenylphosphine oxide) phenyl)naphthalene-4-yl)-1,10-phenanthroline

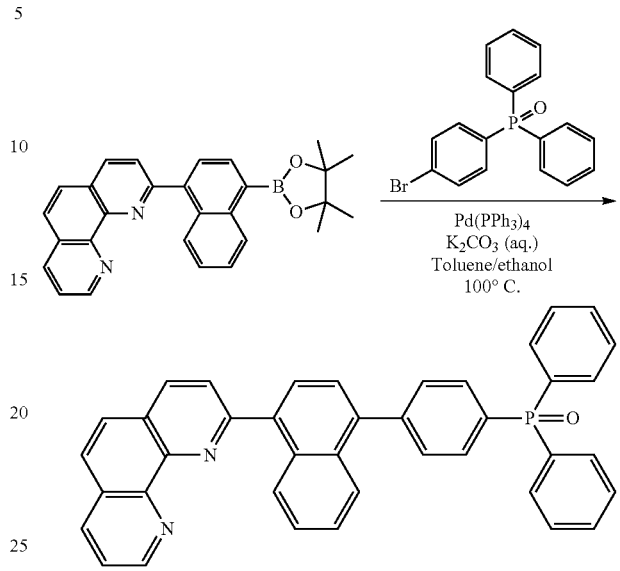

Under nitrogen conditions, (4-bromophenyl)diphenylphosphine oxide (10 g, 28.0 mmol), 2-(1-(4,4,5,5-tetramethyl-1,3,2-dioxaborolan-2-yl)naphthalene-4-yl)-1,10-phenanthroline (14.5 g, 33.6 mmol), tetrakistriphenylphosphine palladium (0) (1.72 g, 1,49 mmol), 4M potassium carbonate aqueous solution (15 mL), toluene (200 mL) and ethanol (20 mL) were refluxed and stirred for 12 hrs. After completion of the reaction, the distilled water (50 mL) was added and stirred for 3 hrs. The mixture was filtered under reduced pressure and separated by column chromatography using methylene chloride (MC) and hexane as an eluent. The resultant was crystallized using MC such that the compound of 2-(1-(4-(diphenylphosphine oxide)phenyl)naphthalene-4-yl)-1,10-phenanthroline (10 g, yield 60%) was obtained.

Organic Light Emitting Diode

1. EXAMPLE 1 (EX1)

An ITO layer was deposited and patterned on a substrate and washed to form the anode (2 mm*2 mm). The substrate was loaded in a vacuum chamber having a base pressure of $5$~$7*10^{-8}$, and layers were sequentially deposited as below.

(1) the HTL (amine-based material, 1200 nm), (2) the blue EML (anthracene-based host and pyrene-based dopant, 250 nm), (3) ETL (pyridine-based material, 120 nm), (4) P-type CGL (250 nm), (5) N-type CGL (2-(10-(4-(diphenylphosphine oxide)phenyl)anthracen-9-yl)-1,10-phenanthroline and Li (2 wt %), 180 nm), (6) HTL (amine-based material, 440 nm), (7) yellow-green EML (carbazole-based host and iridium-based dopant, 300 nm), (8) ETL (imidazole-based material, 400 nm), (9) EIL (LiF) and (10) anode (Al).

2. EXAMPLE 2 (EX2)

Instead of the compound of 2-(10-(4-(diphenylphosphine oxide)phenyl)anthracen-9-yl)-1,10-phenanthroline, the compound of 2-(1-(4-(diphenylphosphine oxide)phenyl)naphthalen-4-yl)-1,10-phenanthroline was used at the N-type CGL.

3. COMPARATIVE EXAMPLE (REF)

Instead of the compound of 2-(10-(4-(diphenylphosphine oxide)phenyl)anthracen-9-yl)-1,10-phenanthroline, the compound of Bphen was used at the N-type CGL.

The driving voltage, the emitting efficiency (cd/A), the external quantum efficiency (EQE), the color coordinate and the lifetime (T95 W) of the organic light emitting diodes of "Comparative Example" and "Example 1" and "Example 2" are measured and listed in Table 1. The current density, the emitting efficiency, the intensity and the lifetime are shown in FIGS. 5A to 5D.

TABLE 1

|     | Volt [V] | Cd/A | EQE [%] | CIEx  | CIEy  | T95 W  |
|-----|----------|------|---------|-------|-------|--------|
| Ref | 7.3      | 63.3 | 26.3    | 0.324 | 0.338 | 85.52  |
| Ex1 | 7.0      | 65.2 | 27.5    | 0.319 | 0.329 | 122.08 |
| Ex2 | 7.0      | 66.5 | 28.0    | 0.318 | 0.328 | 122.07 |

As shown in Table 1 and FIGS. 5A to 5D, in comparison to "Comparative Example", the driving voltage is decreased, and the emitting efficiency and the external quantum efficiency are improved. In addition, the lifetime is remarkably increased (about 42.7%).

The organic compound of the present invention preferably includes the phenanthroline core, which has a nitrogen atom of a relatively electron rich $sp^2$ hybrid orbital, and a phosphine oxide moiety, which has an excellent electron transporting property and an excellent thermal stability. The electron transporting property of the organic compound of the present invention is improved based on the chemical structure of the organic compound. Accordingly, when the organic compound is used for the ETL and/or the N-type CGL of the organic light emitting diode and the OLED device, the driving voltage is reduced, and the lifetime and the emitting efficiency are improved.

In addition, since the nitrogen atom of the phenanthroline core in the organic compound is combined or bonded with the alkali metal or the alkali earth metal as a dopant in the ETL or an N-type charge generation layer (CGL) to form a gap state, the electron transporting property of the ETL or the N-type CGL is further improved. Moreover, since the organic compound is combined with the alkali metal or the alkali earth metal in the ETL or the N-type CGL, the diffusion of the alkali metal or the alkali earth metal into the EML or the P-type CGL is prevented. Accordingly, when the organic compound is used for the N-type CGL in a tandem structure light emitting diode or OLED device, the electron is efficiently transferred from the N-type CGL into the ETL, the driving voltage is reduced, and the lifetime and the emitting efficiency are improved.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. An organic light emitting diode, comprising:
a first electrode and a second electrode facing each other;
a first emitting part between the first electrode and the second electrode and including a first emitting material layer and a first electron transporting layer;
a second emitting part between the first emitting part and the second electrode and including a second emitting material layer and a second electron transporting layer; and
a first charge generation layer between the first emitting part and the second emitting part,
wherein at least one of the first electron transporting layer, the second electron transporting layer and the first charge generation layer includes an organic compound represented by a following Formula:

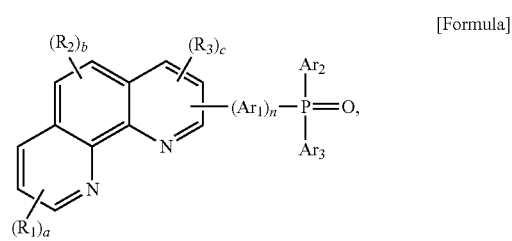

[Formula]

wherein each of $R_1$ to $R_3$ is independently selected from the group consisting of hydrogen, deuterium, tritium, substituted $C_1$-$C_{20}$ alkyl, non-substituted $C_1$-$C_{20}$ alkyl, substituted $C_1$-$C_{20}$ alkoxy, non-substituted $C_1$-$C_{20}$ alkoxy, substituted $C_5$-$C_{30}$ cycloalkyl, non-substituted $C_5$-$C_{30}$ cycloalkyl, substituted $C_4$-$C_{30}$ heterocycloalkyl, non-substituted $C_4$-$C_{30}$ heterocycloalkyl, substituted $C_5$-$C_{30}$ aryl, non-substituted $C_5$-$C_{30}$ aryl, substituted $C_4$-$C_{30}$ heteroaryl, non-substituted $C_4$-$C_{30}$ heteroaryl, substituted $C_5$-$C_{30}$ oxyaryl, non-substituted $C_5$-$C_{30}$ oxyaryl, substituted $C_4$-$C_{30}$ hetero-oxyaryl, and non-substituted $C_4$-$C_{30}$ hetero-oxyaryl,
wherein a is 2 or 3, b is 1 or 2, c is 2 or 3, and the summation of a, b and c is 7,
wherein $Ar_1$ is selected from the group consisting of substituted $C_1$-$C_{20}$ alkylene, non-substituted $C_1$-$C_{20}$ alkylene, substituted $C_5$-$C_{30}$ cycloalkylene, non-substituted $C_5$-$C_{30}$ cycloalkylene, substituted $C_4$-$C_{30}$ heterocycloalkylene, non-substituted $C_4$-$C_{30}$ heterocycloalkylene, substituted $C_5$-$C_{30}$ arylene, non-substituted $C_5$-$C_{30}$ arylene, substituted $C_4$-$C_{30}$ heteroarylene, and non-substituted $C_4$-$C_{30}$ heteroarylene,
wherein each of $Ar_2$ and $Ar_3$ is independently selected from the group consisting of hydrogen, deuterium, tritium, halogen, nitrile, substituted $C_5$-$C_{30}$ aryl, non-substituted $C_5$-$C_{30}$ aryl, substituted $C_4$-$C_{30}$ heteroaryl, non-substituted $C_4$-$C_{30}$ heteroaryl, substituted $C_5$-$C_{30}$ oxyaryl, non-substituted $C_5$-$C_{30}$ oxyaryl, substituted $C_4$-$C_{30}$ hetero-oxyaryl, and non-substituted $C_4$-$C_{30}$ hetero-oxyaryl, and
wherein n is 0, 1 or 2.

2. The organic light emitting diode according to claim 1, wherein the first charge generation layer includes a P-type charge generation layer and an N-type charge generation layer between the P-type charge generation layer and the first electron transporting layer, and
wherein the organic compound is included in the N-type charge generation layer, and the N-type charge generation layer further includes an alkali metal or an alkali earth metal.

3. The organic light emitting diode according to claim 1, further comprising:
a third emitting part between the second emitting part and the second electrode and including a third emitting material layer and a third electron transporting layer; and
a second charge generation layer between the second emitting part and the third emitting part,
wherein at least one of the third electron transporting layer and the second charge generation layer includes the organic compound.

4. The organic light emitting diode according to claim 1, wherein the organic compound is selected from:
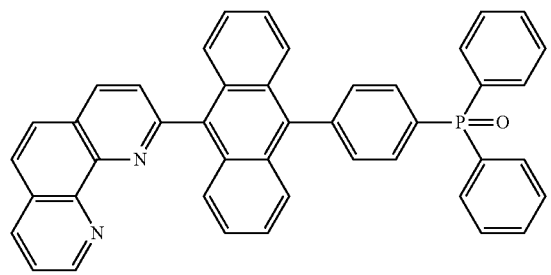
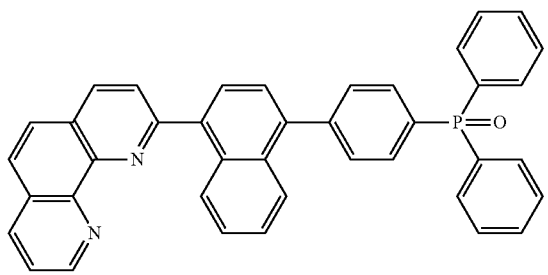
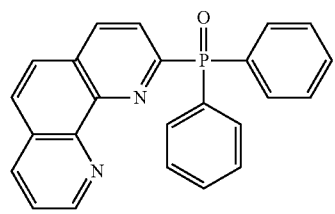
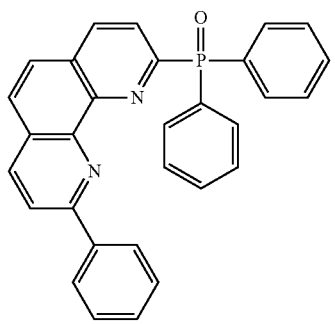
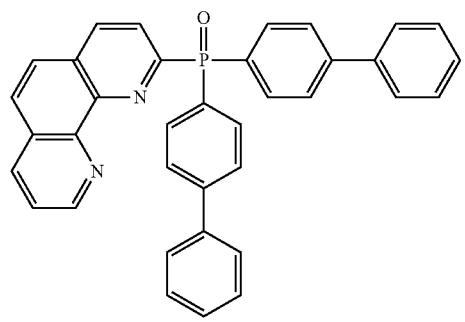
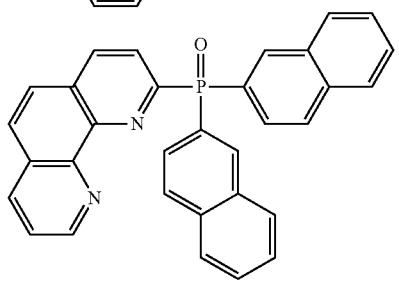
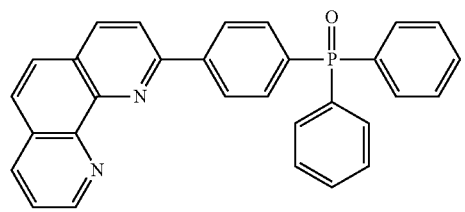
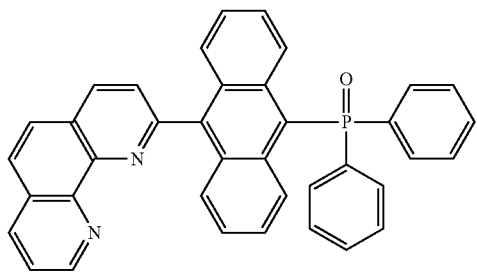
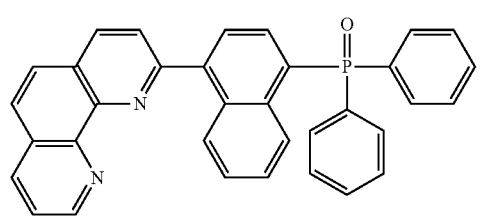
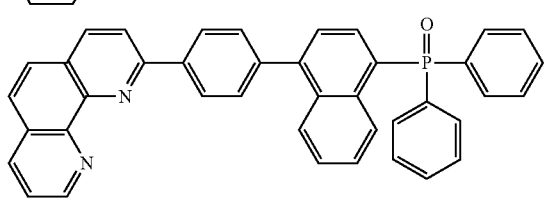
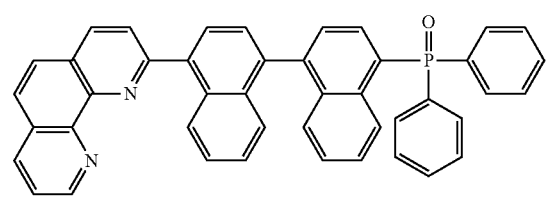
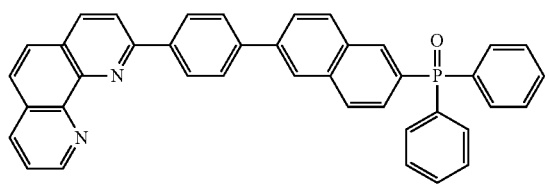

51
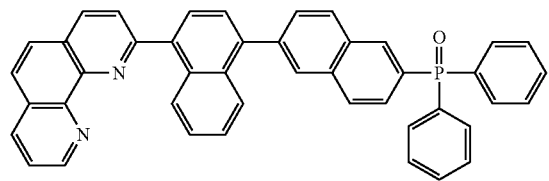
52
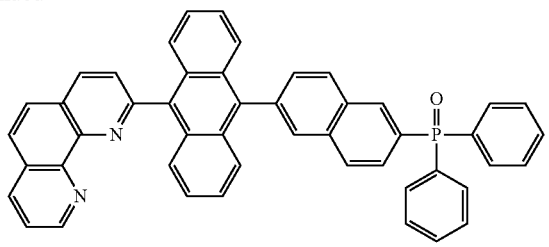
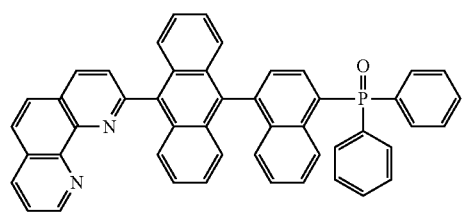
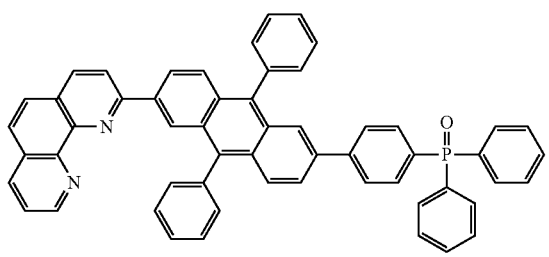
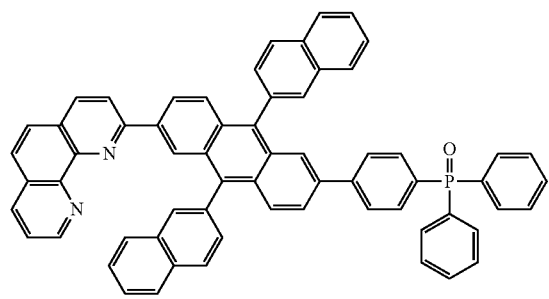
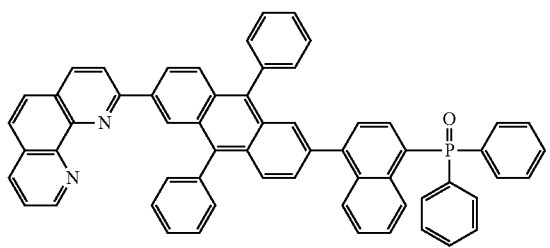
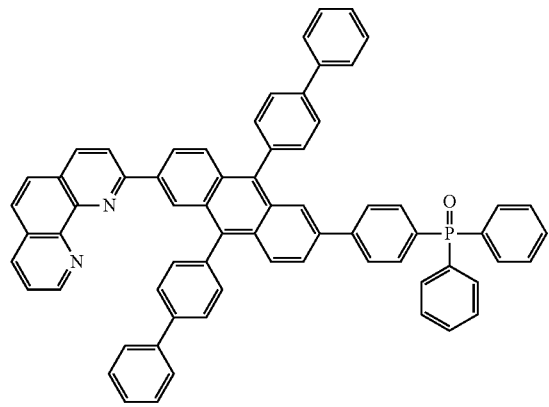
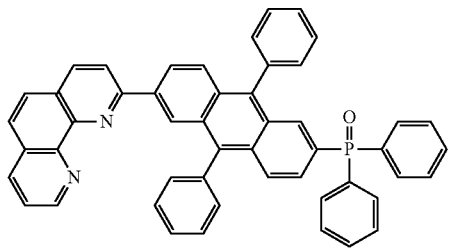
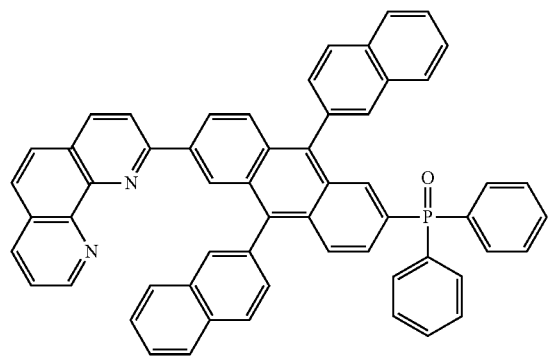
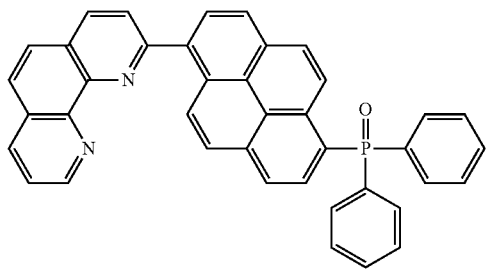

-continued
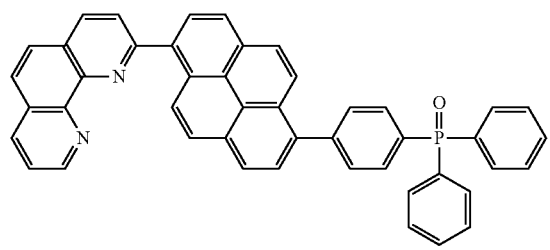
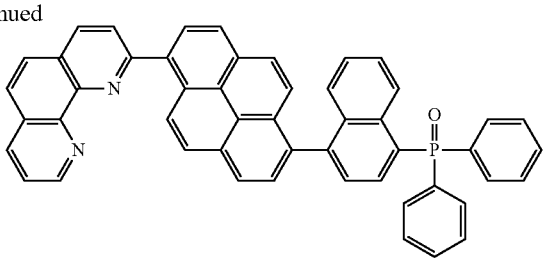
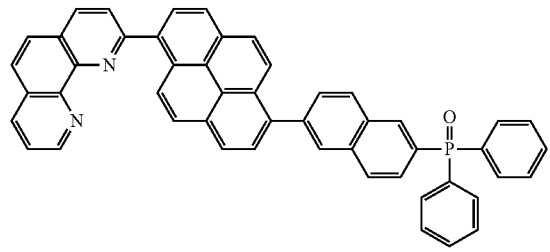
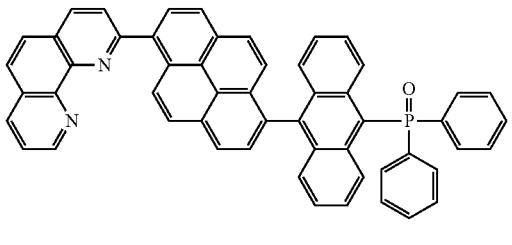
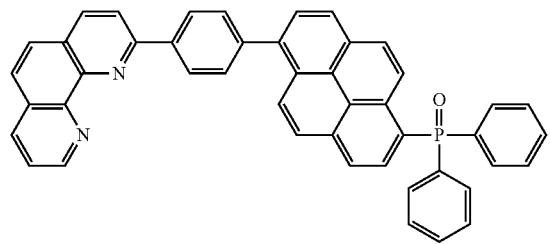
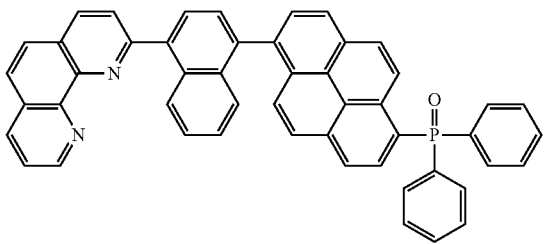
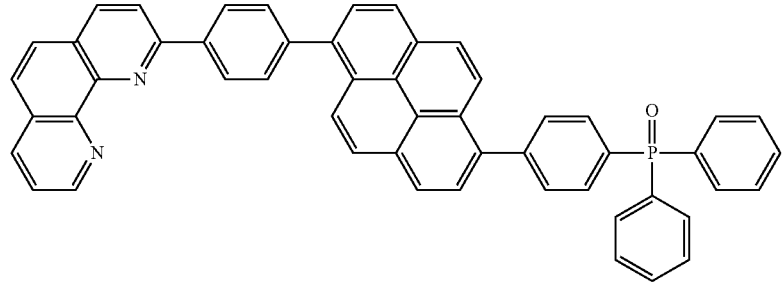
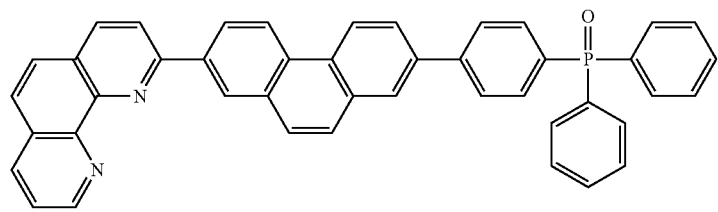
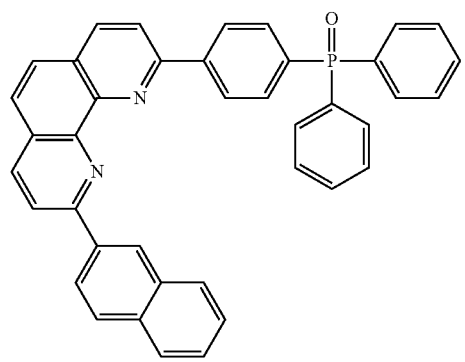
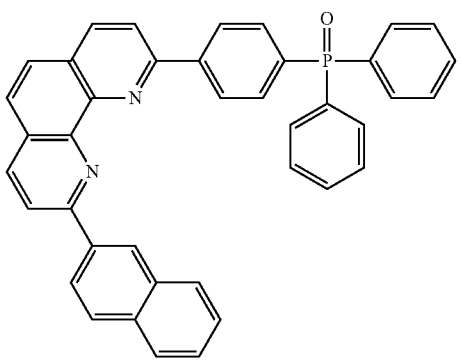

55
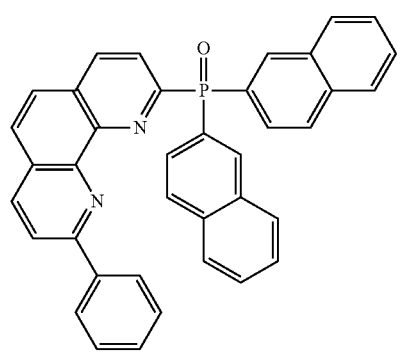
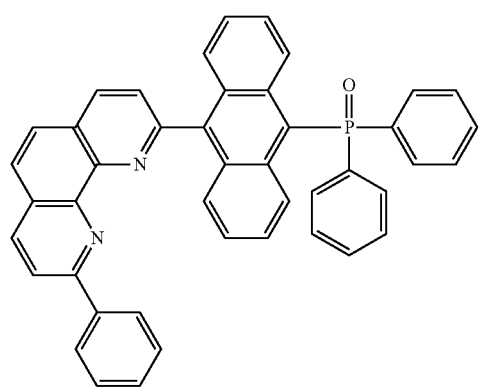
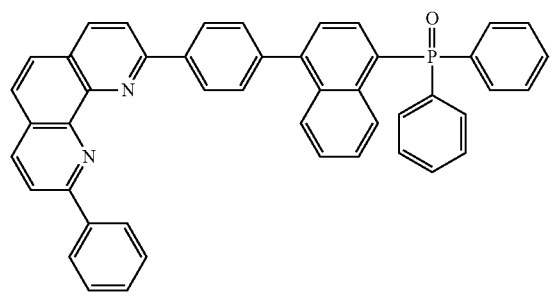
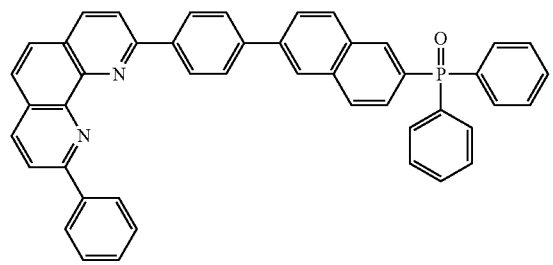
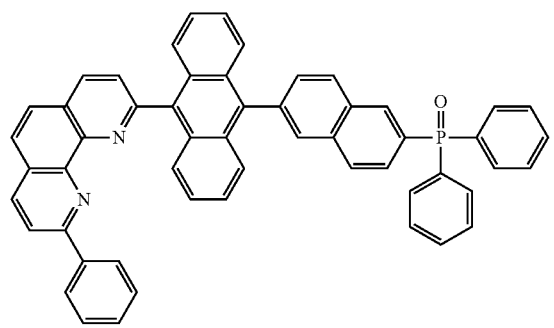
56
-continued
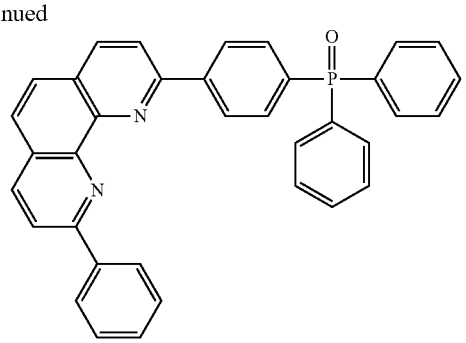
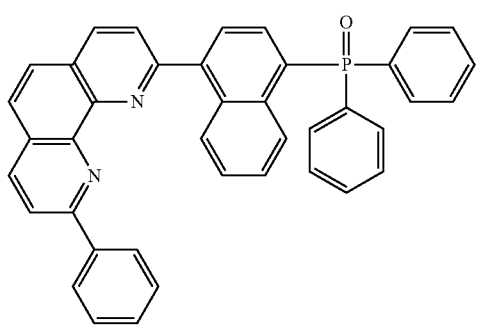
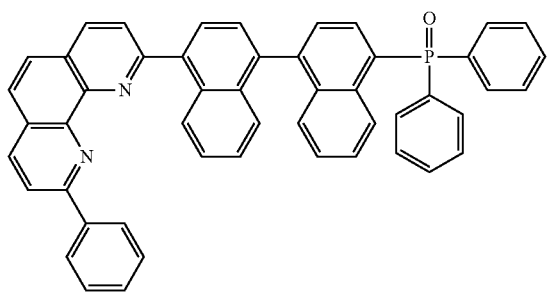
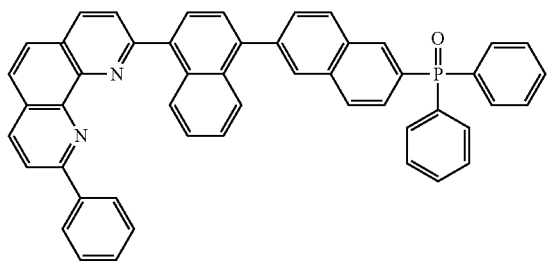
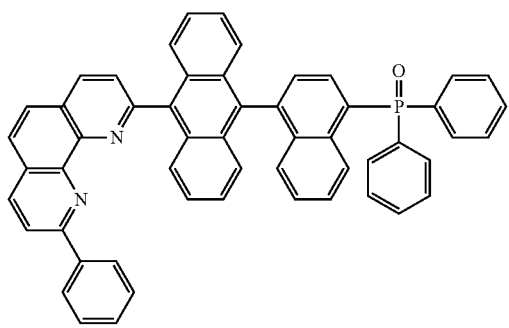

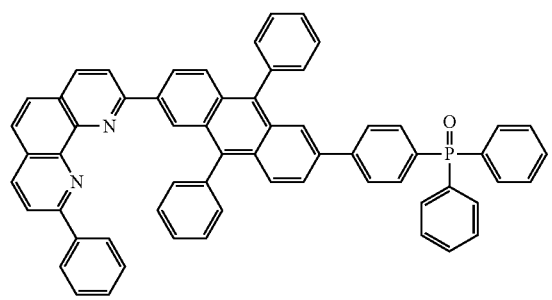
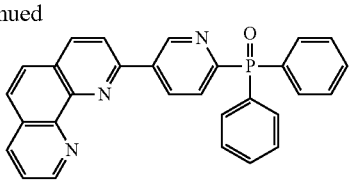
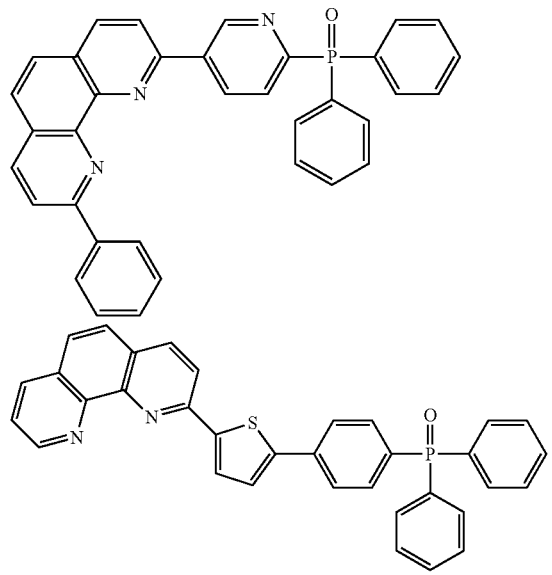
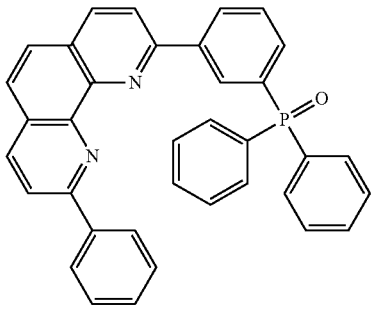
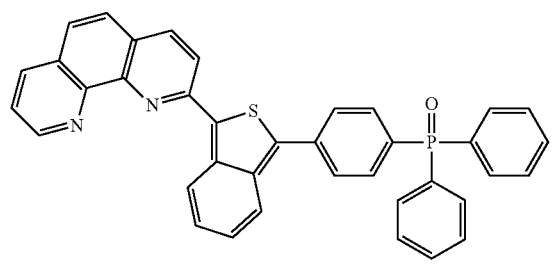
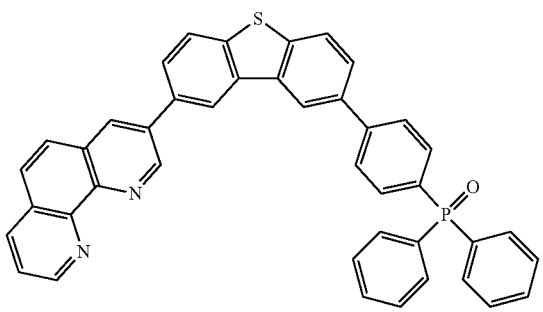
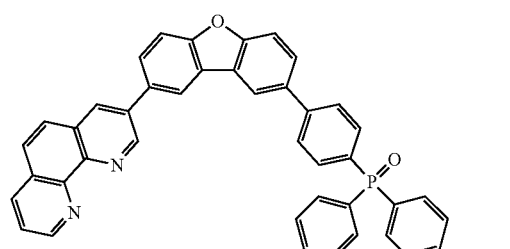
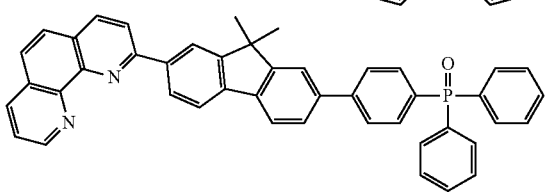
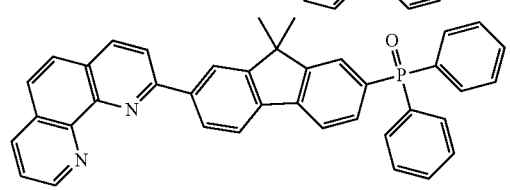
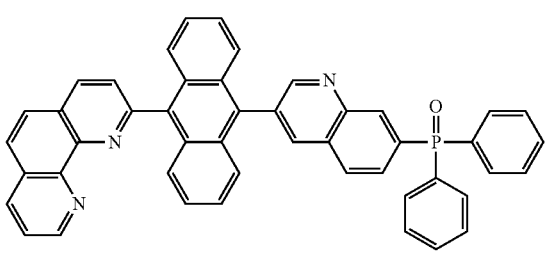

59
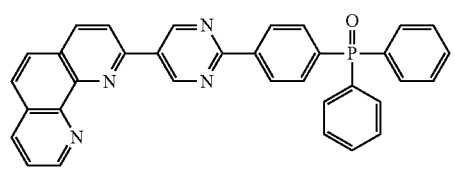
60
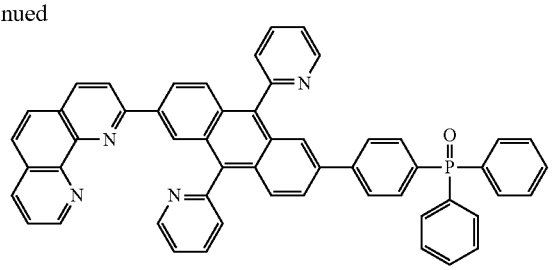
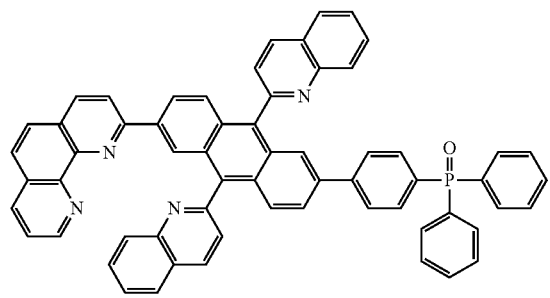
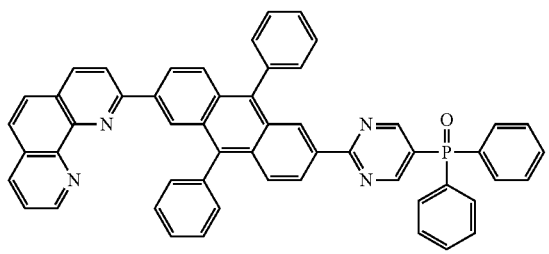
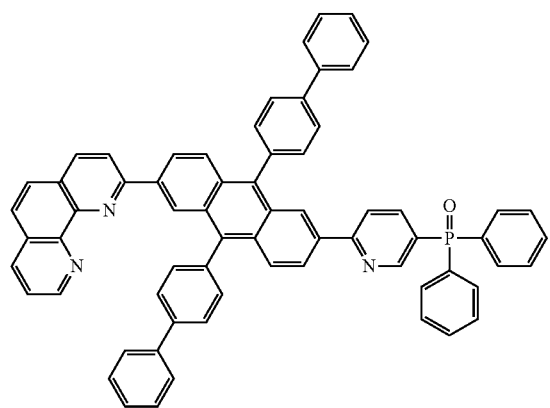
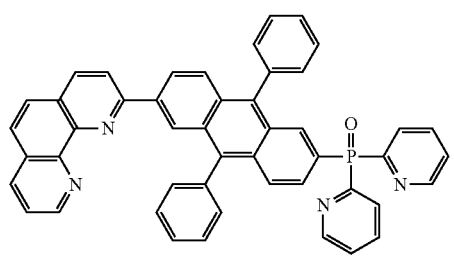
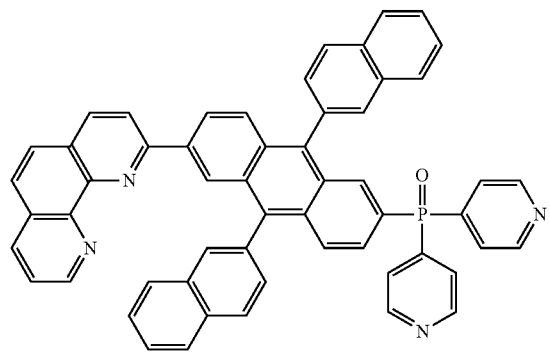
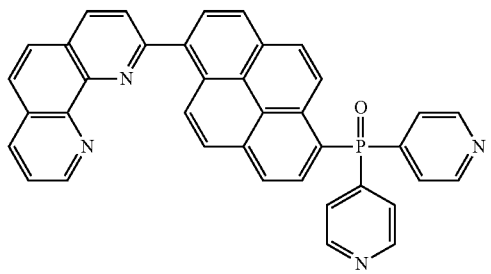
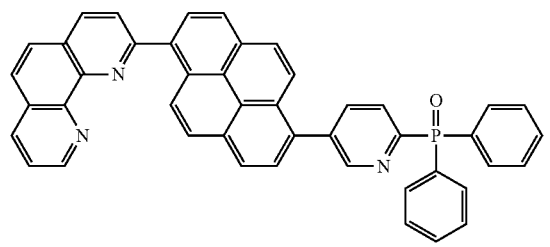
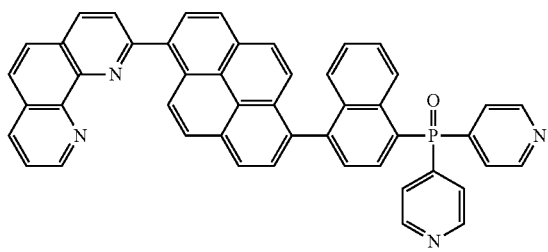

61
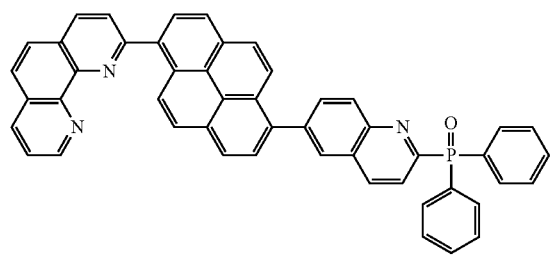
-continued
62
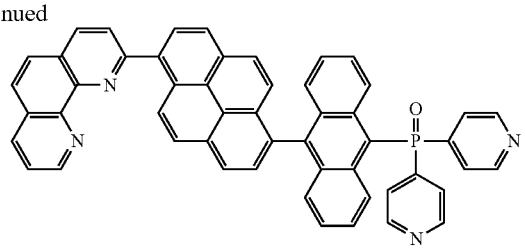
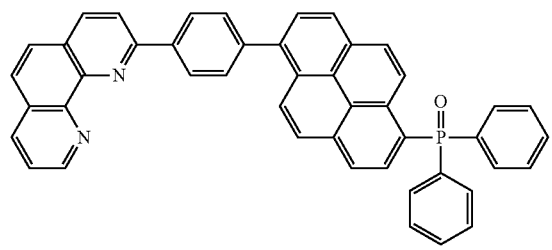
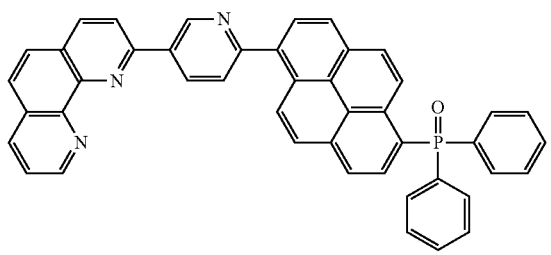
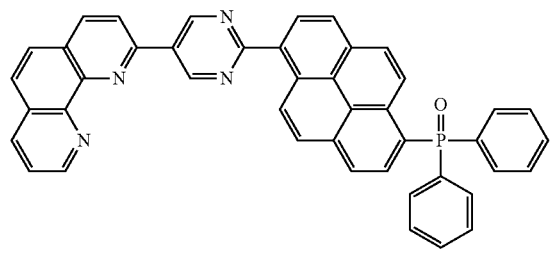
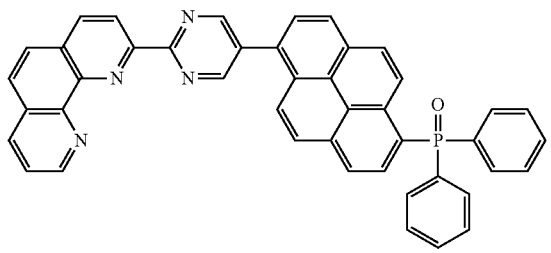
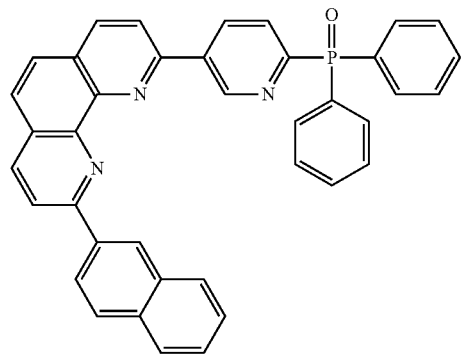
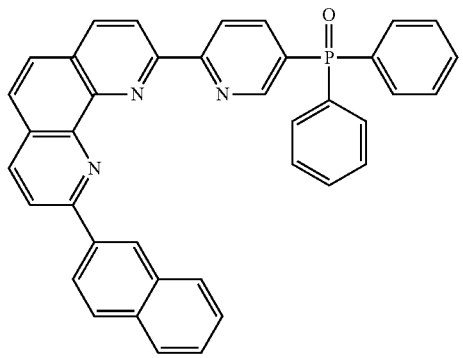
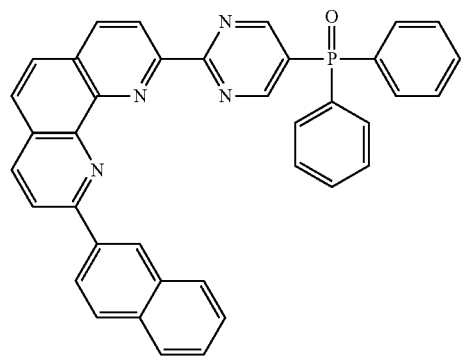
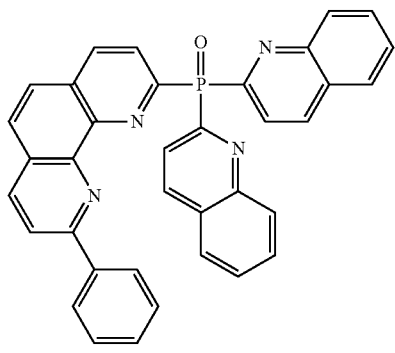

63
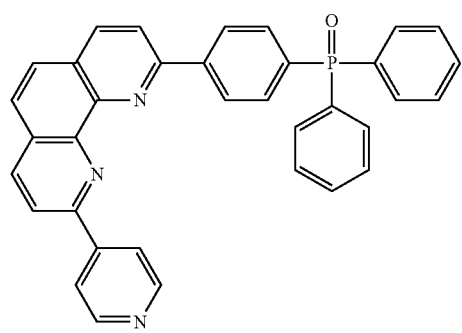
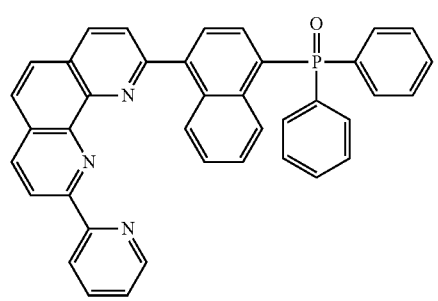
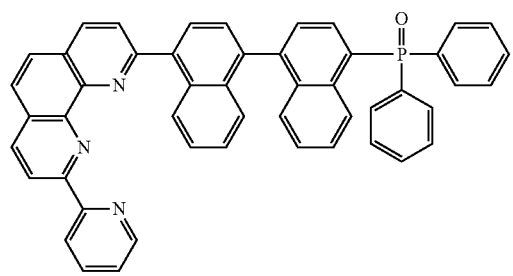
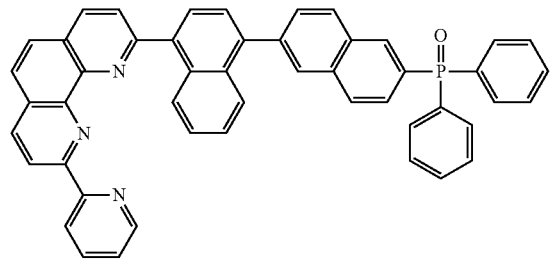
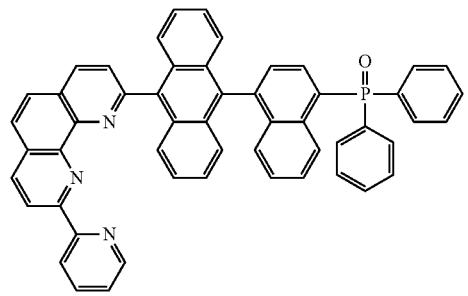
64
-continued
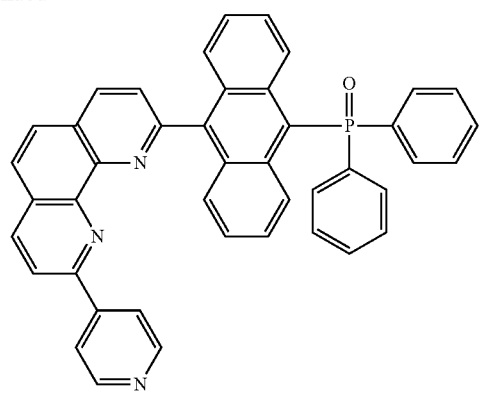
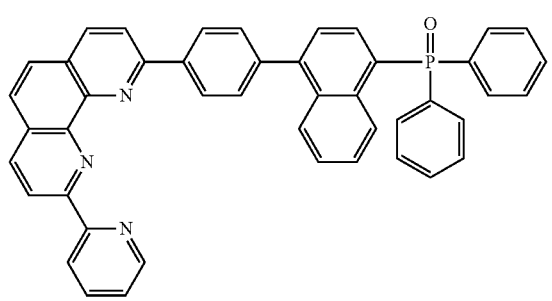
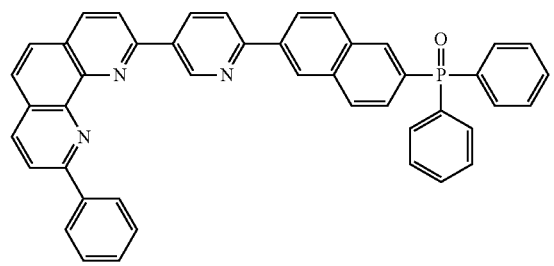
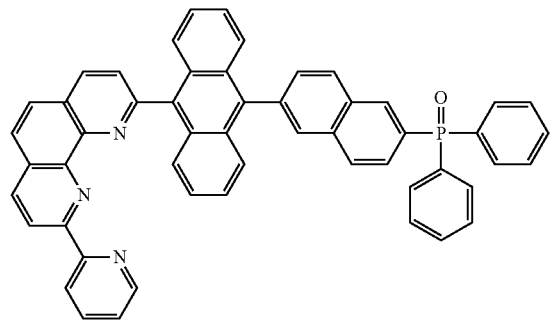
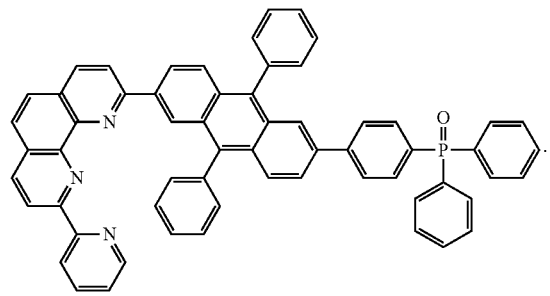

5. An organic light emitting display device, comprising:
a substrate;
the organic light emitting diode of claim 1; and
a thin film transistor between the substrate and the organic light emitting diode and connected to the organic light emitting diode.

6. The organic light emitting display device according to claim 5, wherein the first charge generation layer includes a P-type charge generation layer and an N-type charge generation layer between the P-type charge generation layer and the first electron transporting layer, and
wherein the organic compound is included in the N-type charge generation layer, and the N-type charge generation layer further includes an alkali metal or an alkali earth metal.

7. The organic light emitting display device according to claim 5, further comprising:

a third emitting part between the second emitting part and the second electrode and including a third emitting material layer and a third electron transporting layer; and
a second charge generation layer between the second emitting part and the third emitting part,
wherein at least one of the third electron transporting layer and the second charge generation layer includes the organic compound.

8. The organic light emitting display device according to claim 5, further comprising a color filter between the substrate and the organic light emitting diode or over the second electrode.

9. The organic light emitting display device according to claim 5, wherein the organic compound is selected from:

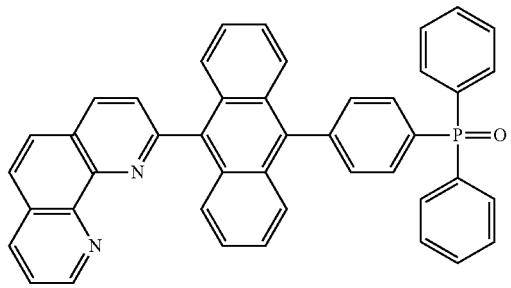

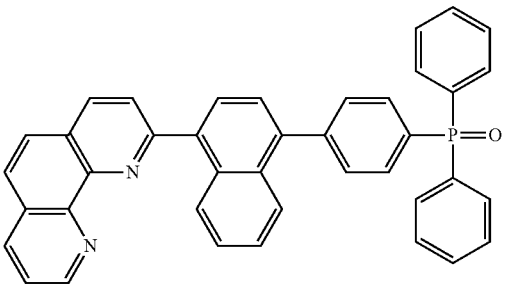

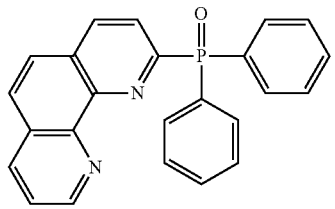

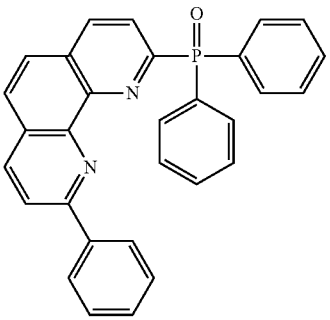

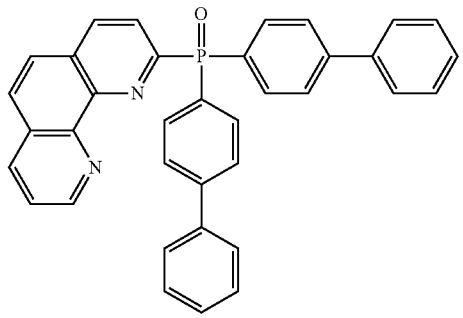

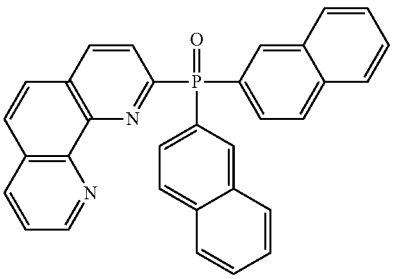

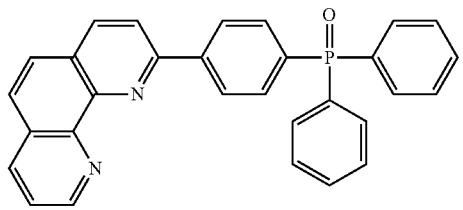

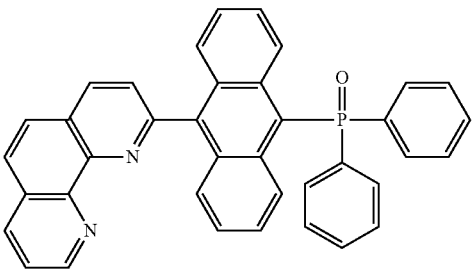

67
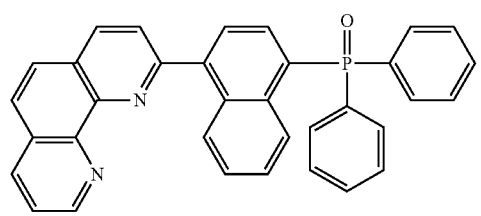
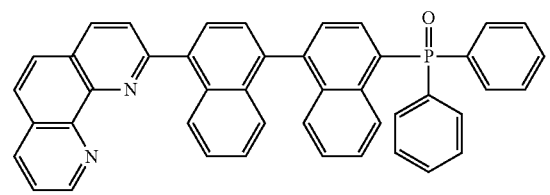
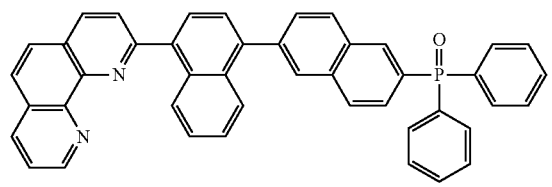
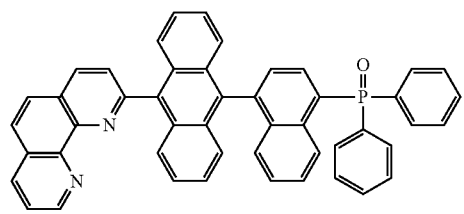
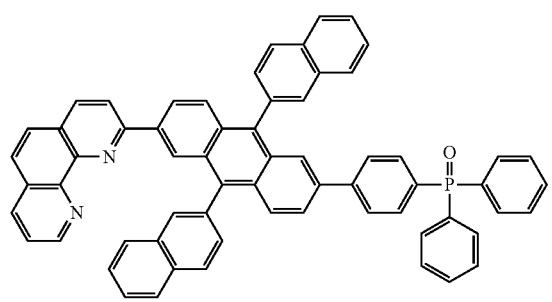
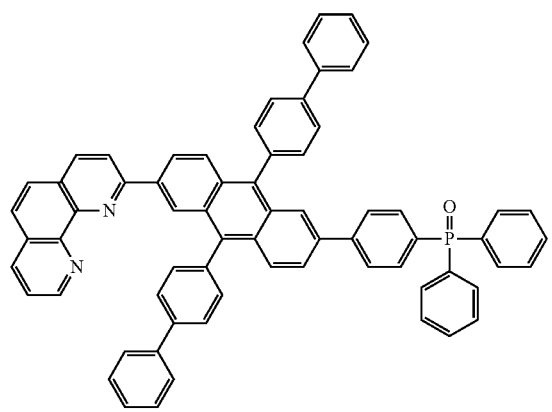
68
-continued
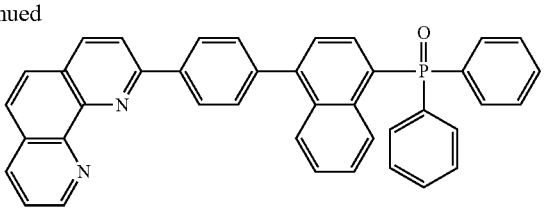
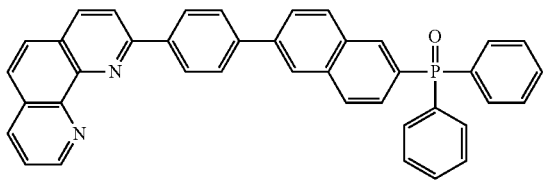
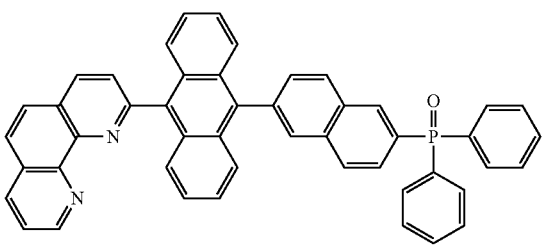
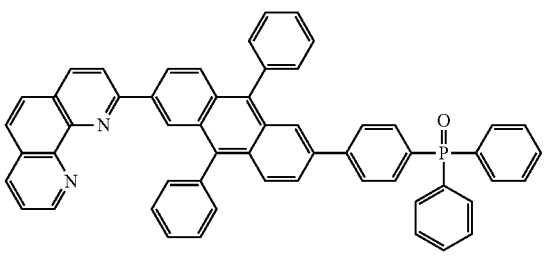
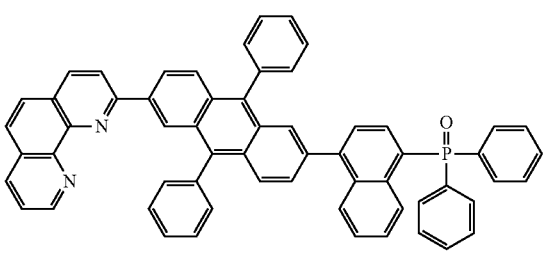
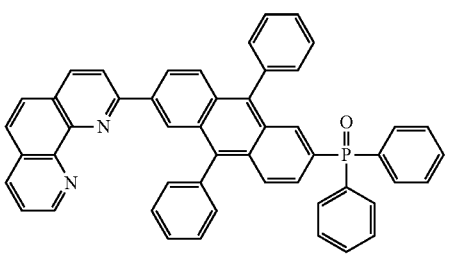

-continued
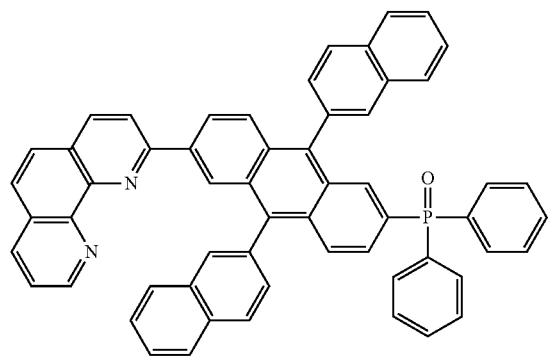
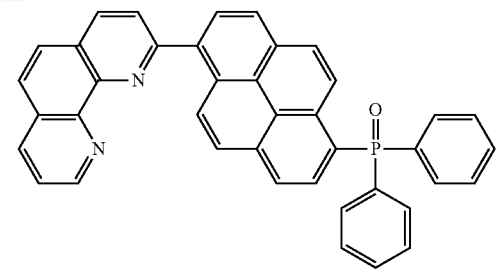
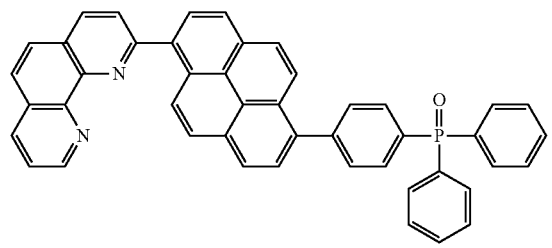
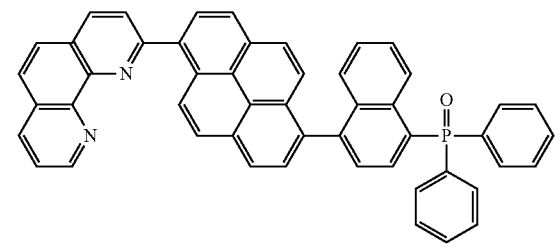
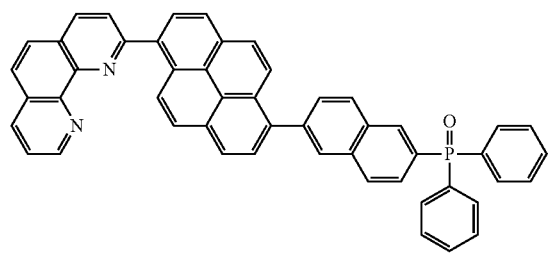
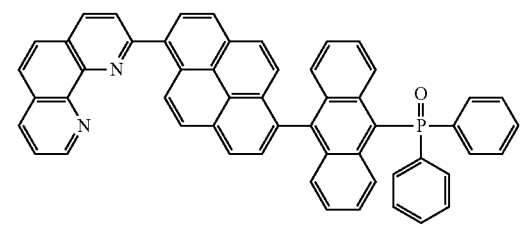
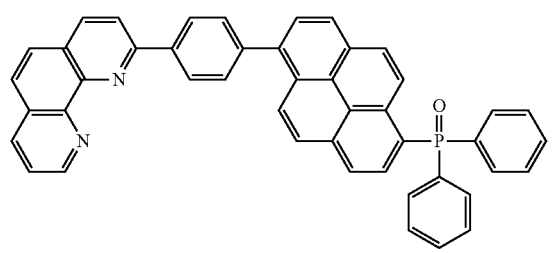
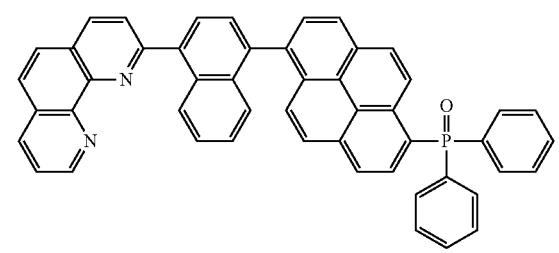
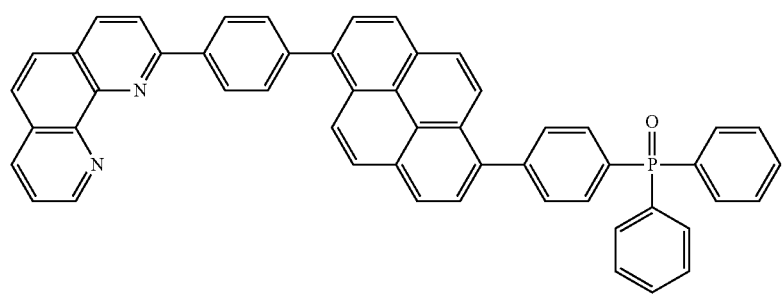
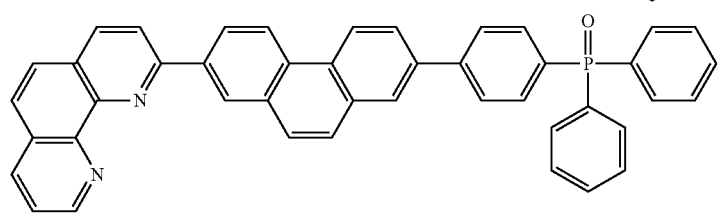

71 72
-continued
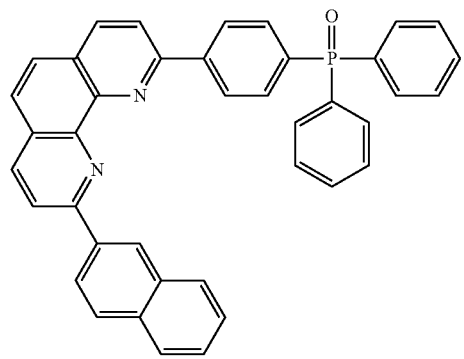
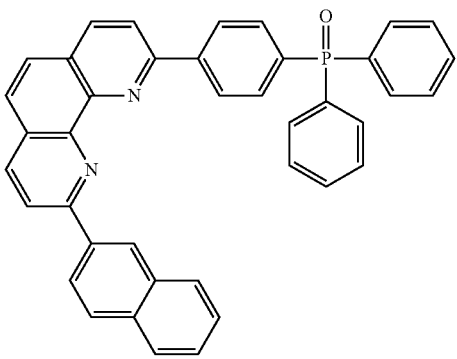
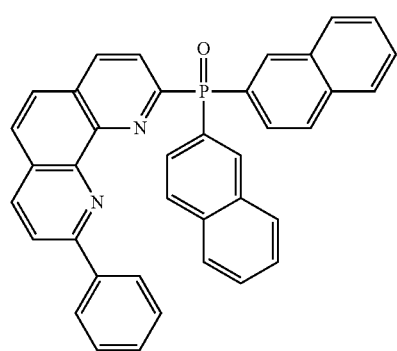
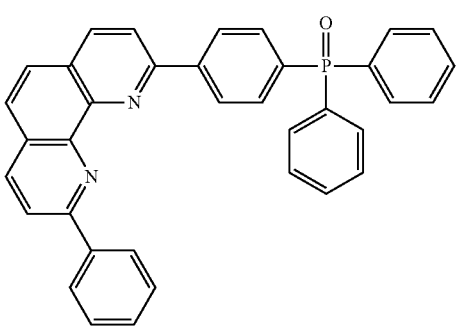
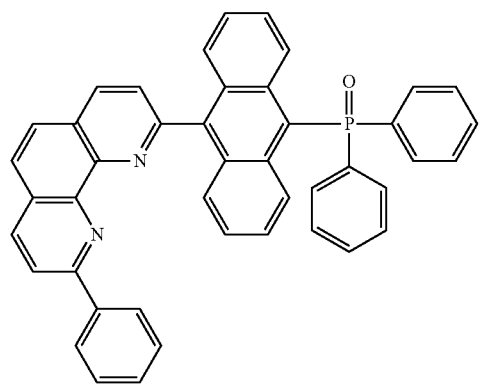
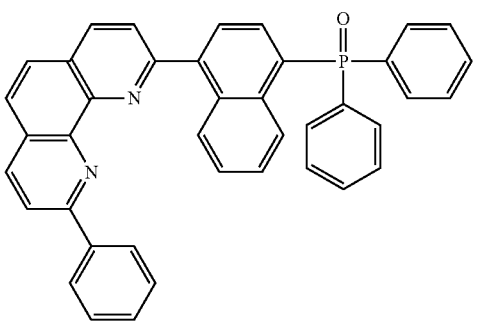
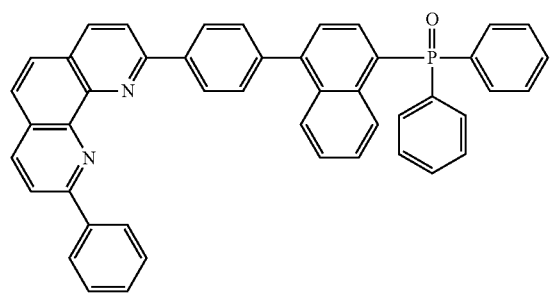
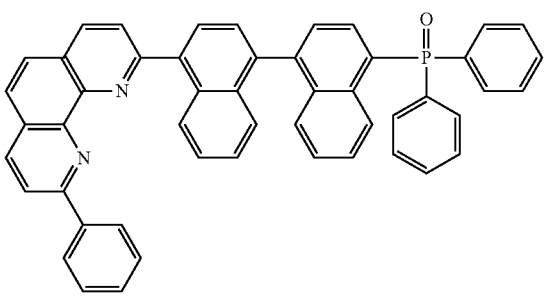
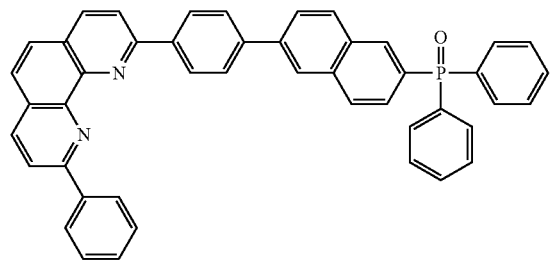
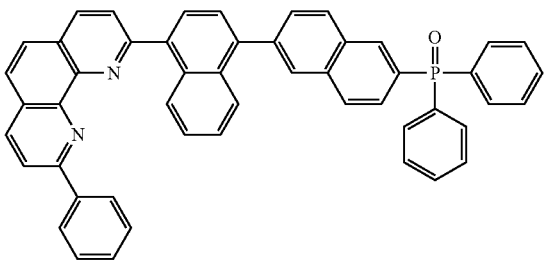

73 74
-continued
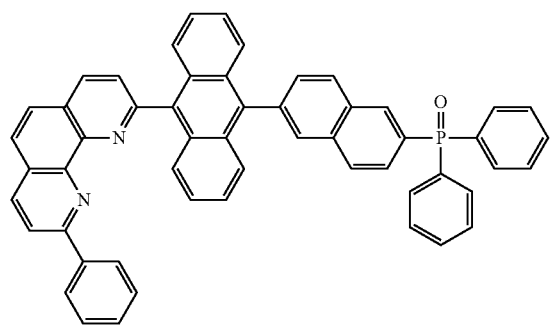
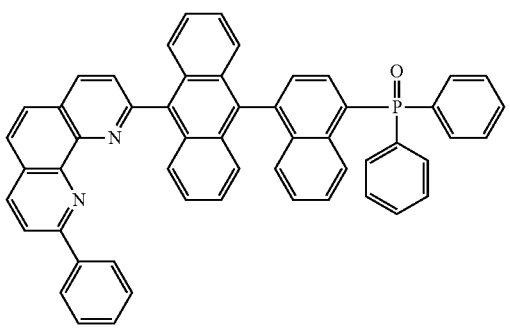
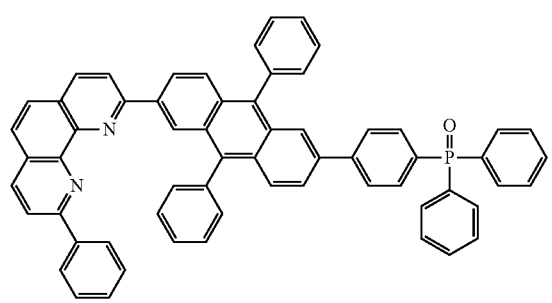
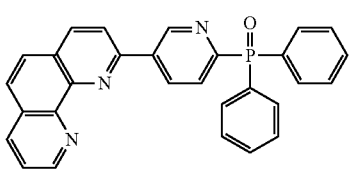
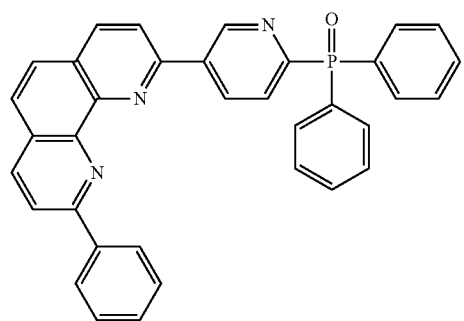
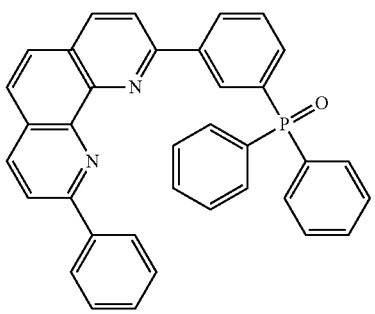
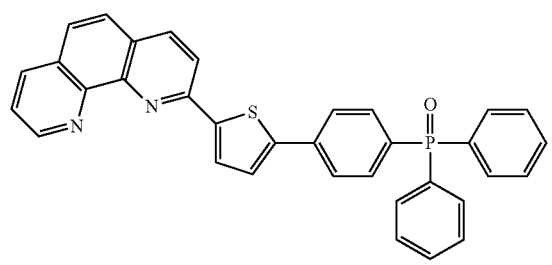
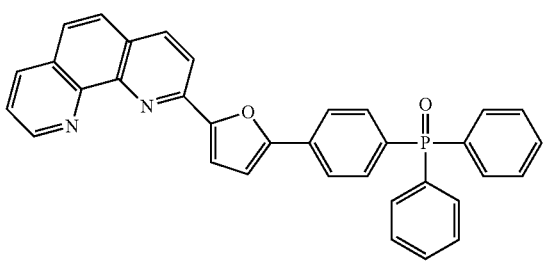
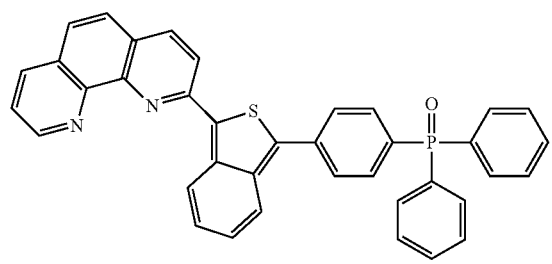
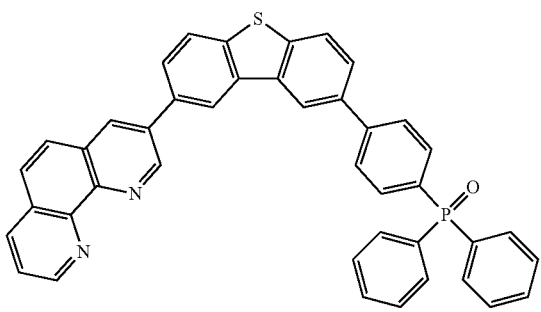

75 76
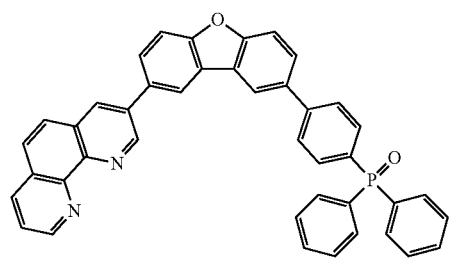
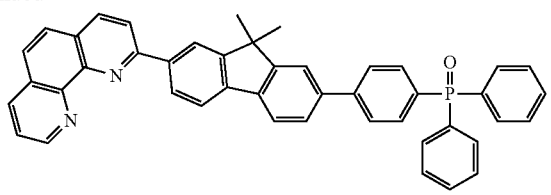
-continued
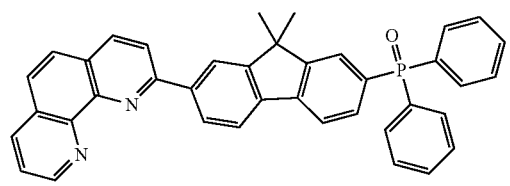
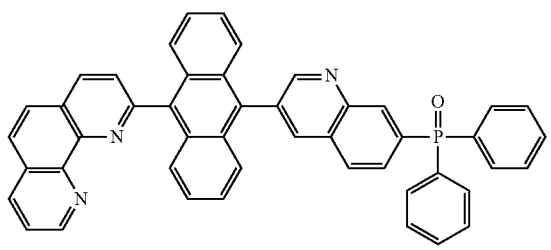
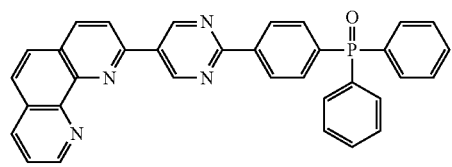
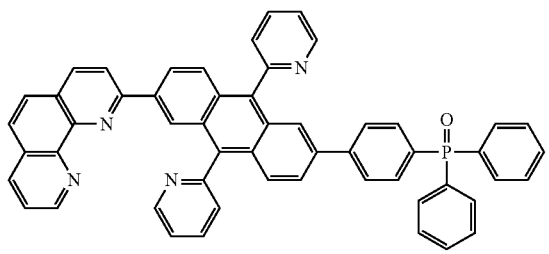
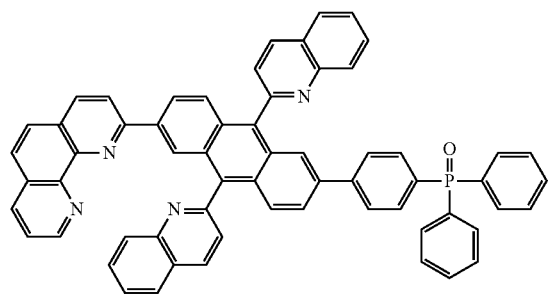
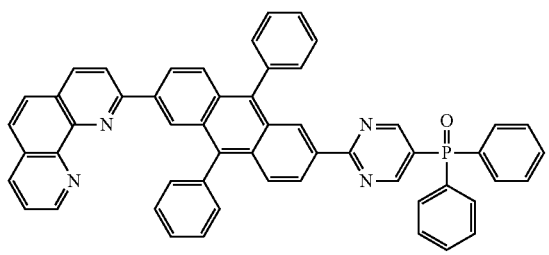
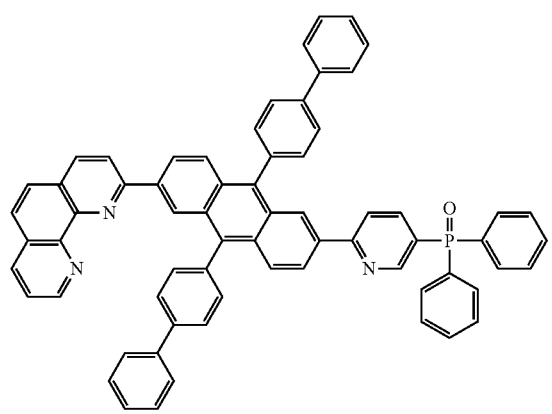
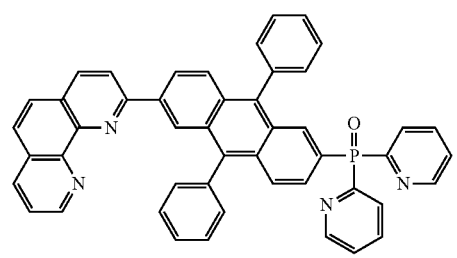

-continued
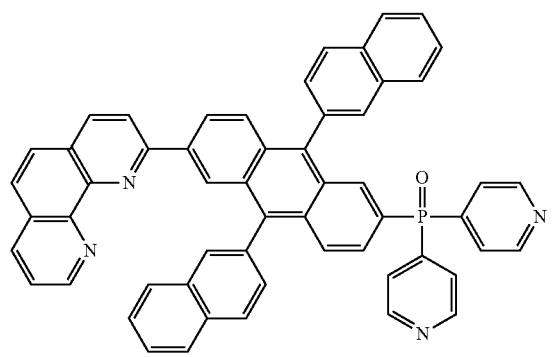
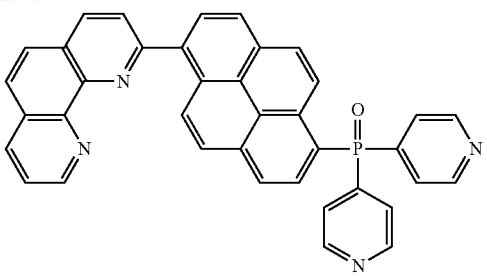
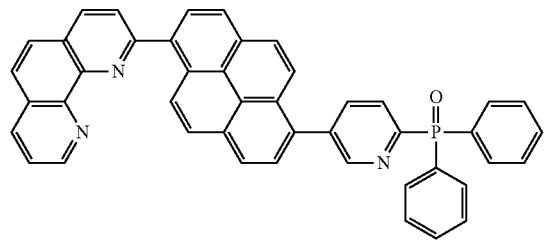
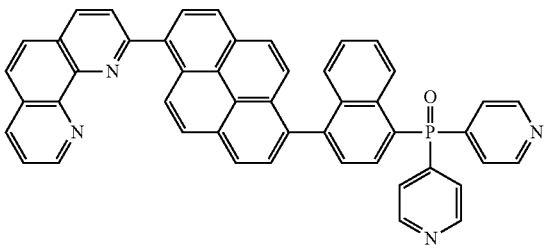
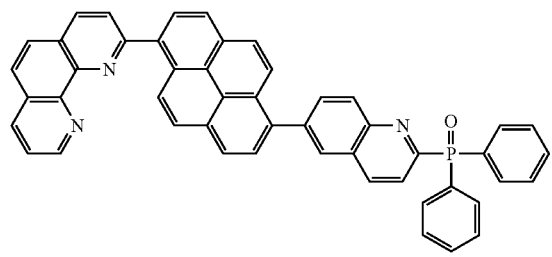
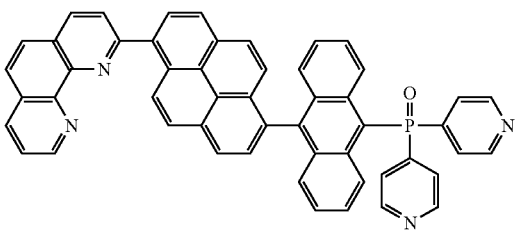
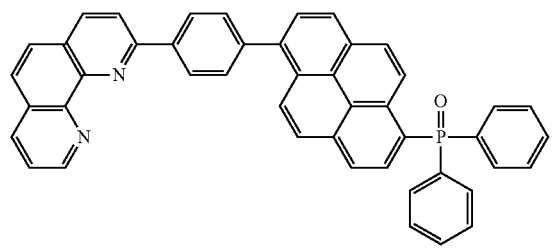
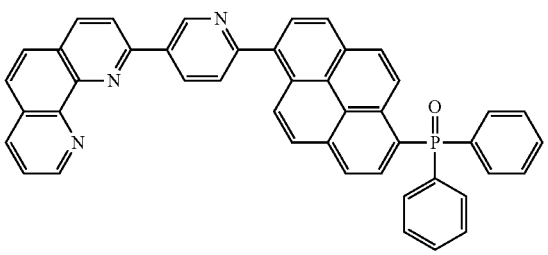
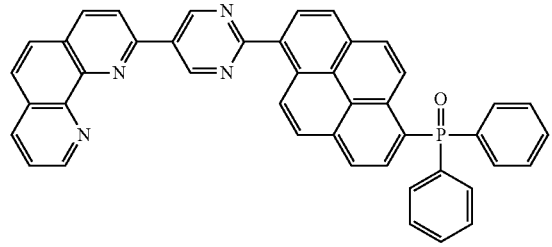
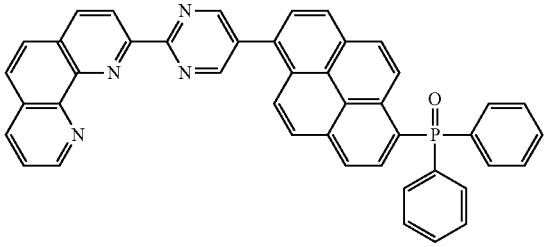
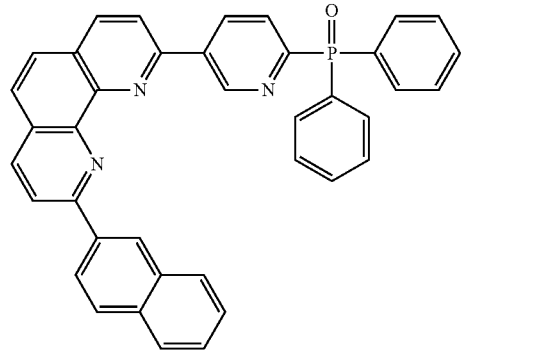
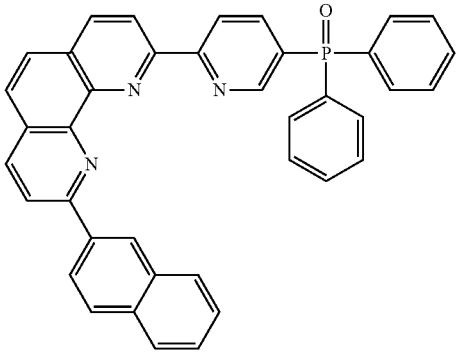

-continued
79
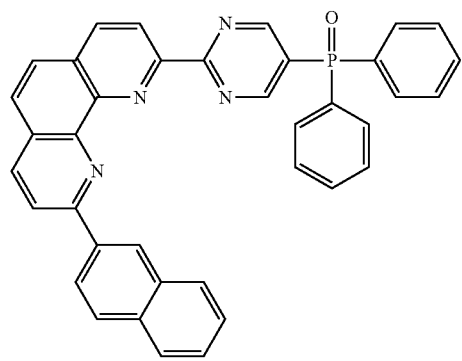
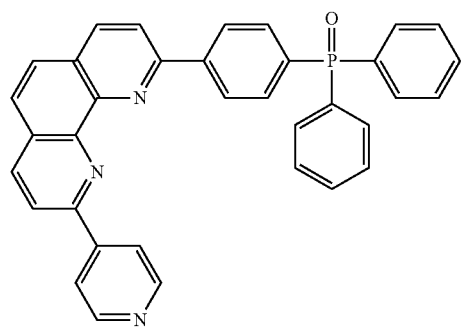
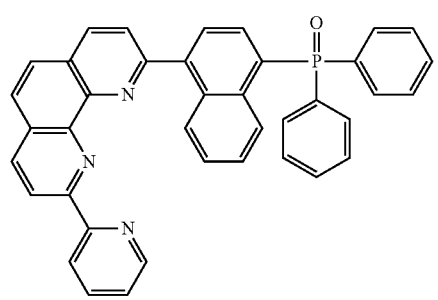
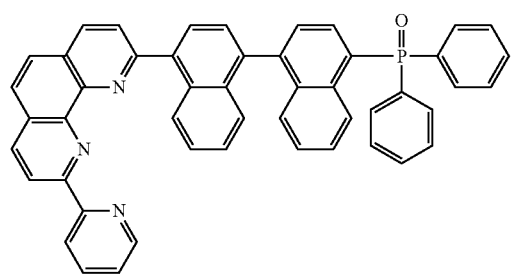
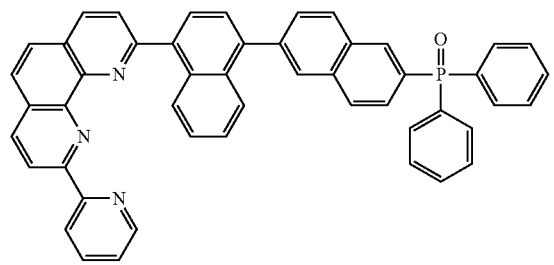
80
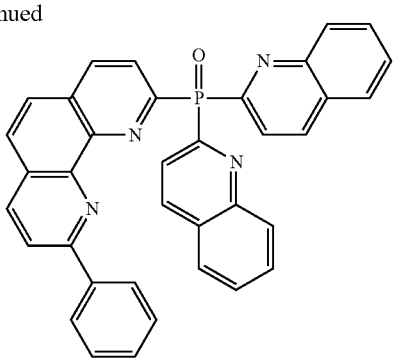
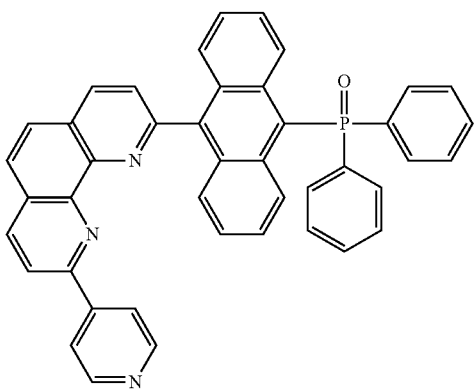
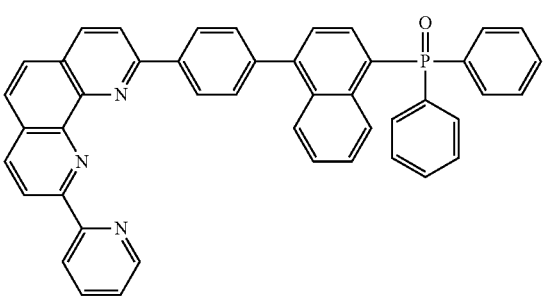
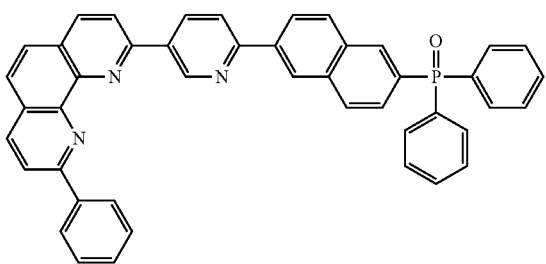
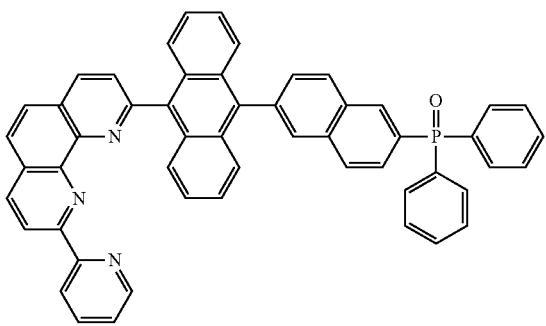

-continued

81

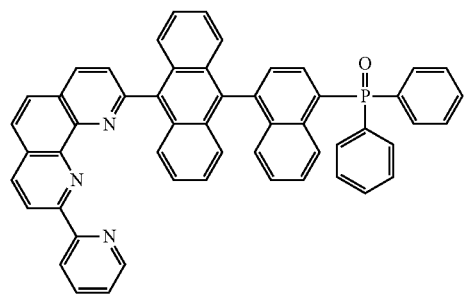

82

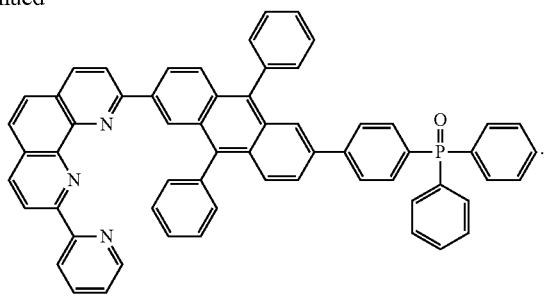

10. The organic light emitting diode according to claim 1, wherein $Ar_1$ is selected from the group consisting of substituted $C_5$-$C_{30}$ arylene, non-substituted $C_5$-$C_{30}$ arylene, substituted $C_4$-$C_{30}$ heteroarylene, and non-substituted $C_4$-$C_{30}$ heteroarylene, and wherein each of $R_1$ to $R_3$ is independently selected from the group consisting of substituted $C_5$-$C_{30}$ aryl, non-substituted $C_5$-$C_{30}$ aryl, substituted $C_4$-$C_{30}$ heteroaryl, and non-substituted $C_4$-$C_{30}$ heteroaryl.

11. The organic light emitting diode according to claim 1, wherein the first charge generation layer includes a P-type charge generation layer and an N-type charge generation layer between the P-type charge generation layer and the first electron transporting layer, and wherein the N-type charge generation layer includes the organic compound.

12. The organic light emitting display device according to claim 5, wherein the first charge generation layer includes a P-type charge generation layer and an N-type charge generation layer between the P-type charge generation layer and the first electron transporting layer, and wherein the IN-type charge generation layer includes the organic compound.

13. The organic light emitting display device according to claim 5, wherein $Ar_1$ is selected from the group consisting of substituted $C_5$-$C_{30}$ arylene, non-substituted $C_5$-$C_3$ arylene, substituted $C_4$-$C_{30}$ heteroarylene, and non-substituted $C_4$-$C_{30}$ heteroarylene, and wherein each of $R_1$ to $R_3$ is independently selected from the group consisting of substituted $C_5$-$C_{30}$ aryl, non-substituted $C_5$-$C_{30}$ aryl, substituted $C_4$-$C_{30}$ heteroaryl, and non-substituted $C_4$-$C_{30}$ heteroaryl.

* * * * *